(12) United States Patent
McNutt et al.

(10) Patent No.: US 11,495,355 B2
(45) Date of Patent: Nov. 8, 2022

(54) METHOD, SYSTEM AND COMPUTER-READABLE MEDIA FOR TREATMENT PLAN RISK ANALYSIS

(71) Applicant: The Johns Hopkins University, Baltimore, MD (US)

(72) Inventors: Todd McNutt, Severna Park, MD (US); Joseph Moore, Owings Mills, MD (US); Scott Robertson, Red Lion, PA (US); Fumbeya Marungo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 448 days.

(21) Appl. No.: 15/311,420

(22) PCT Filed: May 15, 2015

(86) PCT No.: PCT/US2015/031202
§ 371 (c)(1),
(2) Date: Nov. 15, 2016

(87) PCT Pub. No.: WO2015/176011
PCT Pub. Date: Nov. 19, 2015

(65) Prior Publication Data
US 2017/0083682 A1 Mar. 23, 2017

Related U.S. Application Data

(60) Provisional application No. 62/088,052, filed on Dec. 5, 2014, provisional application No. 62/022,429, filed
(Continued)

(51) Int. Cl.
*A61N 5/10* (2006.01)
*G16H 50/30* (2018.01)
(Continued)

(52) U.S. Cl.
CPC .......... *G16H 50/30* (2018.01); *A61N 5/1031* (2013.01); *A61N 5/1038* (2013.01); *G16H 50/70* (2018.01);
(Continued)

(58) Field of Classification Search
CPC .... G16H 50/20; G16H 20/40; G06F 19/3481; A61N 2005/1041; G06Q 50/22–24
See application file for complete search history.

(56) References Cited

U.S. PATENT DOCUMENTS 9,943,702 B2 * 4/2018 Kumar ................ G06F 19/3481
2008/0214933 A1 * 9/2008 Von Busch .......... A61B 5/0059
600/431
(Continued)

FOREIGN PATENT DOCUMENTS

| CN | 101247852 B | * | 12/2011 | .......... A61N 5/1031 |
|---|---|---|---|---|
| JP | 2009-515233 A | | 4/2009 | |
| WO | WO-2009072618 A1 | | 6/2009 | |

OTHER PUBLICATIONS

F. Mirzazadeh, "Using SNP Data to Predict Radiation Toxicity for Prostate Cancer Patients" in University of Alberta, Edmonton, 2010. (Year: 2010).*
(Continued)

*Primary Examiner* — Joseph D Burgess
(74) *Attorney, Agent, or Firm* — Venable LLP; Henry J. Daley; Aziz H. Poonawalla

(57) ABSTRACT

A method, system and computer readable medium of: providing feature data of at least one organ at risk or target volume of said patient from a database of non-transitory data stored on a data storage device of prior patients data; generating, using a data processor, a distribution of dose points of the at least one organ at risk or target volume of said patient based on said feature data; calculating, using the data processor, at least one of (i) a probability of toxicity for
(Continued)

the at least one organ at risk or (ii) a probability of treatment failure for the at least one target volume, based on said distribution of dose points; assessing, using the data processor, a dosimetric-outcome relationship based on the calculated probability; and automatically formulating, using the data processor, a treatment plan using the dosimetric-outcome relationship to minimize the at least one treatment-related risk.

16 Claims, 34 Drawing Sheets

Related U.S. Application Data on Jul. 9, 2014, provisional application No. 61/993,621, filed on May 15, 2014.

(51) Int. Cl.
*G16H 50/70* (2018.01)
*G16H 50/50* (2018.01)
*G16H 20/40* (2018.01)

(52) U.S. Cl.
CPC ...... *A61N 2005/1041* (2013.01); *G16H 20/40* (2018.01); *G16H 50/50* (2018.01)

(56) References Cited

U.S. PATENT DOCUMENTS

| | | | | |
|---|---|---|---|---|
| 2011/0130614 | A1* | 6/2011 | Schulz | G16H 30/40 600/1 |
| 2011/0153547 | A1* | 6/2011 | McNutt | G06N 5/02 706/54 |
| 2011/0274338 | A1* | 11/2011 | Park | A61B 5/4331 382/133 |
| 2012/0014507 | A1* | 1/2012 | Wu | A61N 5/10 378/65 |
| 2012/0136194 | A1* | 5/2012 | Zhang | A61N 5/103 600/1 |
| 2012/0207359 | A1* | 8/2012 | Konukoglu | G06K 9/6277 382/128 |
| 2013/0142310 | A1* | 6/2013 | Fahimian | A61N 5/103 378/65 |
| 2013/0289332 | A1* | 10/2013 | Purdie | A61N 5/1039 600/1 |
| 2013/0324784 | A1* | 12/2013 | Fredriksson | A61N 5/1031 600/1 |
| 2014/0235923 | A1* | 8/2014 | McNutt | A61N 5/1031 600/1 |
| 2014/0244309 | A1* | 8/2014 | Francois | G16H 10/60 705/3 |
| 2014/0275709 | A1* | 9/2014 | Khorrami | A61N 5/1031 600/1 |
| 2014/0350322 | A1* | 11/2014 | Schulte | A61N 5/1077 600/1 |
| 2015/0095043 | A1* | 4/2015 | Cordero Marcos | A61N 5/1031 705/2 |
| 2015/0251017 | A1* | 9/2015 | De Crevoisier | A61N 5/1071 250/252.1 |

OTHER PUBLICATIONS

Bentzen et al., "Quantitative analyses of normal tissue effects in the clinic (QUANTEC): An introduction to the scientific issues," Int. J. Radiat. Oncol. Biol. Phys. 76, S3-S9 (2010).

Buettner et al., "Novel approaches to improve the therapeutic index of head and neck radiotherapy: An analysis of data from the PARSPORT randomised phase III trial," Radiotherapy and Oncology 103:82-87 (2012).

Burman et al., "Fitting of Normal Tissue Tolerance Data to an Analytic Function", International Journal of Radiation Oncology* Biology* Physics, 21(1), 1991, pp. 123-135.

Cattell, "Scalable Sql and Nosql Data Stores", ACM SIGMOD Record, 39(4): 12-27 (2011).

Cios et al., "Uniqueness of Medical Data Mining," Artificial intelligence in medicine, 26(1): 1-24 (2002).

Dhar, "Data Science and Prediction," Communications of the ACM, 56(12): 64-73 (2013).

Emami et al., "Tolerance of Normal Tissue to Therapeutic Irradiation," International Journal of Radiation Oncology* Bioloqy* Physics, 21(1): 109-122 (1991).

Fayyad et al., "From Data Mining to Knowledge Discovery in Databases," AI magazine, 17(3): 37-54 (1996).

Intensity Modulated Radiation Therapy Collaborative Working Group, "Intensity-Modulated Radiotherapy: Current Status and Issues of Interest", International Journal of Radiation Oncology* Bioloqy* Physics, 51(4), 2001, pp. 880-914.

Kumar et al., "Radiation Dose to the Floor of Mouth Muscles Predicts Swallowing Complications Following Chemoradiation in Oropharyngeal Squamus Cell Carcinoma," Oral Oncology 50: 65-70 (2014).

Kutcher et al., "Calculation of Complication Probability Factors for Non-Uniform Normal Tissue Irradiation: The Effective Volume Method Gerald," I. J. Radiation Oncology * Biology * Physics 16(6): 1623-1630 (1989).

Kutcher et al., "Histogram Reduction Method for Calculating Complication Probabilities for Three-Dimensional Treatment Planning Evaluations", International Journal of Radiation Oncology* Biology* Physics, 21(1): 137-146 (1991).

Marks et al., "Use of Normal Tissue Complication Probability Models in the Clinic," International Journal of Radiation Oncology* Biology* Physics, 76(3): S10-S19 (2010).

Redmond et al., "Association between Radiation Dose to Neuronal Progenitor Cell Niches and Temporal Lobes and Performance on Neuropsychological Testing in Children: a Prospective Study," Neuro-Oncology 15(3): 360-369 (2013).

Wu et al., "Data-Driven Approach to Generating Achievable Dose-Volume Histogram Objectives in Intensity-Modulated Radiotherapy Planning", International Journal of Radiation Oncology* Biology* Physics, 79(4): 1241-1247 (2011).

International Search Report in International Application No. PCT/US2015/031202, dated Aug. 17, 2015.

Trotti et ai., "CTCAE v3.0: development of a comprehensive grading system for the adverse effects of cancer treatment", Semin. Radiat. Oncol., (2003), vol. 13, No. 3, pp. 176-181.

List et al., "The performance status scale for head and neck cancer patients and the functional assessment of cancer therapy-head and neck scale: A study of utility and validity", Cancer, (1996), vol. 77, No. 11, pp. 2294-2301.

Chen et al., "The development and validation of a dysphagia-specific quality-of-life questionnaire for patients with head and neck cancer: The M. D. Anderson dysphagia inventory", Arch. Otolaryngol. Neck Surg., (2001), vol. 127, No. 7, pp. :870-876.

Yang et al., "Browser based platform in maintaining clinical activities—use of the iPads in head and neck clinics", J. Phys. Conf. Ser., (2014), vol. 489, No. 1, 012095.

Schmarzo, Big Data: Understanding How Data Powers Big Business. 1st edition. Indianapolis, IN: Wiley; 2013. [BOOK].

Wu et al., "Patient geometry-driven information retrieval for IMRT treatment plan quality control", Med. Phys., (2009), vol. 36, No. 12, pp. 5497-5505.

Ries et al., SEER Cancer Statistics Review, 1975-2005. National Cancer Institute; 2008. [BOOK].

DeHart et al., "Emergency department applications of digital dictation and natural language processing", J. Ambulatory Care Manage, (1992), vol. 15, No. 4, pp. 18-23.

Hazlehurst et al., "MediClass: A system for detecting and classifying encounter-based clinical events in any electronic medical record", J. Am. Med. Inform. Assoc., (2005), vol. 12, No. 5, pp. 517-529.

(56) References Cited

OTHER PUBLICATIONS

Das et al.,"Intensity-modulated radiation therapy dose prescription, recording, and delivery: patterns of variability among institutions and treatment planning systems", J. Natl. Cancer Inst., (2008), vol. 100, No. 5, pp. 300-307.
Mell et al., "Intensity-modulated radiation therapy use in the U.S", Cancer, (2005), vol. 104, No. 6, pp. 1296-1303.
Jalali, "Particle therapy in clinical practice: is there enough evidence to justify the current surge in interest?", J. Cancer Res. Ther., (2008), vol. 4, No. 2, pp. 54-56.
Pijls-Johannesma et al., "Cost-effectiveness of particle therapy: current evidence and future needs", Radiother. Oncol. J. Eur. Soc, Ther. Radiol. Oncol., (2008), vol. 89, No. 2, pp. 127-134.
Jackson, "Summarizing our knowledge of normal tissue tolerances: the progress and future directions of QUANTEC", Med. Phys., (2008), vol. 35, p. 2863.
Marks, "A clinician's view of QUANTEC", Med. Phys., (2008), vol. 35, No. 6.
Potosky et al., "Five-year outcomes after prostatectomy or radiotherapy for prostate cancer: the prostate cancer outcomes study", J. Natl. Cancer Inst., (2004), vol. 96, No. 18, pp. 1358-1367.
McDade et ai, "A national propensity-adjusted analysis of adjuvant radiotherapy in the treatment of resected pancreatic adenocarcinoma", Cancer, (2010), vol. 116, No. 13, pp. 3257-3266.
Lin et al., "Propensity score-based comparison of long-term outcomes with 3-dimensional conformal radiotherapy vs intensity-modulated radiotherapy for esophageal cancer", Int. J. Radiat. Oncol. Biol. Phys., (2012), vol. 84, No. 5, pp. 1078-1085.
Robertson et al., "A data-mining algorithm for large scale analysis of dose-outcome relationships in a database of irradiated head-and-neck (HN) cancer patients", Med. Phys, (2014), vol. 41, No. 6, p. 410.
Robertson et al., "A data-mining framework for large scale analysis of dose-outcome relationships in a database of irradiated head and neck (HN) cancer patients", Med. Phys., (Jul. 2015), vol. 42, Iss. 7, pp. 4329-4337; https://doi.org/10.1118/1.4922686.
Dawson et al., "Use of principal component analysis to evaluate the partial organ tolerance of normal tissues to radiation", Int. J. Radiat. Oncol. Biol. Phys., (2005), vol. 62, No. 3, pp. 829-837.
El Naqa et al., "Multivariable modeling of radiotherapy outcomes, including dose-volume and clinical factors", Int. J. Radiat. Oncol. Biol. Phys., (2006), vol. 64, No. 4, pp. 1275-1286.
Söhn et al., "incidence of late rectal bleeding in high-dose conformal radiotherapy of prostate cancer using equivalent uniform dose-based and dose-volumne-based normal tissue complication probability models", Int. J. Radiat. Oncol. Biol. Phys., (2007), vol. 67, No. 4, pp. 1066-1073.
Ebert et al., "Derivation and representation of dose-volume response from large clinical trial data sets: an example from the RADAR prostate radiotherapy trial", J. Phys. Conf. Ser., (2014), vol. 489, No. 1, 012090.
Deasy et al., "Radiotherapy dose-volume effects on salivary gland function", Int. J. Radiat. Oncol. Biol. Phys., (2010), vol. 76, pp. S58-S63.
Konings et al., "Volume effects and region-dependent radiosensitivity of the parotid gland", Int. J. Radiat. Oncol. Biol. Phys., (2005), vol. 62, No. 4, pp. 1090-1095.
Buettner et al., "Modeling late rectal toxicities based on a parameterized representation of the 3D dose distribution", Phys. Med. Biol., (2011), vol. 56, No. 7, p. 2103.
Vinogradskiy et ai., "A novel method to incorporate the spatial location of the lung dose distribution into predictive radiation pneumonitis modeling", Int. J. Radiat. Oncol. Biol. Phys., (2012), vol. 82, No. 4, pp. 1549-1555.
Marungo et al., "Creating a data science platform for developing complication risk models for personalized treatment planning in radiation oncology", In: Hawaii International Conference on System Sciences.vol. 48 (in press).
Marungo et al., "Machine learning based risk modeling of voice dysfunction and xerostomia using spatial dose distribution in intensity-modulated radiation therapy", J. Am. Med. Inform. Assoc.
Lyman, "Complication probability as assessed from dose-volume histograms", Radiat. Res., (1985), vol. 104, pp. S13-S19.
Breiman, "Random forests", Mach. Learn., (2001), vol. 45, No. 1, pp. 5-32.
Breiman, "Bagging predictors", Mach. Learn., (1996), vol. 24, No. 2, pp. 123-140.
Matsuo et al., "Anatomy and physiology of feeding and swallowing: Normal and abnormal", Phys. Med. Rehabil. Clin. N. Am., (2008), vol. 19, pp. 691-707.
Acosta et al., "Voxel-based population analysis for correlating local dose and rectal toxicity in prostate cancer radiotherapy", Phys. Med. Biol., (2013), vol. 58, No. 8, p. 2581.
Lyman, "Complication Probability as Assessed from Dose-Volume Histograms", Radiation Research, (1985), vol. 104, No. 2s, pp. S13-S19.
Friedman, "A National Learning Health System", in (Editor, ied. weds.1): Book A National Learning Health System, 2013.
Rubin et al., "Direction for Clinical Radiation Pathology. The Tolerance Dose.", in (Editor, 'ed.weds.1): Book Direction for Clinical Radiation Pathology. The Tolerance Dose., Univ. of Rochester, NY, 1972.
Schmarzo, "Big Data: Understanding How Data Powers Big Business," John Wiley & Sons, 2013 [BOOK].
Dean et al., "Mapreduce: Simplified Data Processing on Large Clusters", Communications of the ACM, (2008), 51(1), pp. 107-113.
Marungo et al., "Creating a Data Science Platform for Developing Complication Risk Models for Personalized Treatment Planning in Radiation Oncology", 48th Hawaii International Conference on System Sciences (HICSS). Kauai, HI USA: IEEE; 2015.
Niemierko et al., "Reporting and analyzing dose distributions: a concept of equivalent uniform dose", Medical physics, (1997), vol. 24, No. 1, pp. 103-110.
Konings et al., "Volume effects and region-dependent radiosensitivity of the parotid gland", International Journal of Radiation Oncology* Biology* Physics. (2005), vol. 62, No. 4, pp. 1090-5.
Konings et al., "Secondary radiation damage as the main cause for unexpected volume effects: A histopathologic study of the parotid gland", International Journal of Radiation Oncology* Biology* Physics, (2006), vol. 64, No. 1, pp. 98-105.
Van Luijk et al., "Bath and shower effects in the rat parotid gland explain increased relative risk of parotid gland dysfunction after intensity-modulated radiotherapy", International Journal of Radiation Oncology* Biology* Physics, (2009), vol. 74, No. 4, pp. 1002-5.
Dornfeld et al., "Radiation doses to structures within and adjacent to the larynx are correlated with long-term diet-and speech-related quality of life", international Journal of Radiation Oncology* Biology* Physics, (2007), vol. 68, No. 3, pp. 750-7.
Dawson et al., "Use of principal component analysis to evaluate the partial organ tolerance of normal tissues to radiation", International Journal of Radiation Oncology* Biology* Physics, (2005), vol. 62, No. 3, pp. 829-37.
Domingos, "A few useful things to know about machine learning", Communications of the ACM, (2012), vol. 55, No. 10, pp. 78-87.
Kohavi, "A study of cross-validation and bootstrap for accuracy estimation and model selection", IJCAI, (1995), p. 1137-1145.
Fayyad et al., "Mufti-interval discretization of continuous-valued attributes for classification learning", (1993), http://hdl.handle.net/2014/35171.
Hand et al., "Idiot's Bayes—not so stupid after all?", International statistical review, (2001), vol. 69, No. 3, pp. 385-398.
Breiman, "Bagging predictors", Machine learning, (1996), vol. 24, No. 2, pp. 123-140.
Breiman, "Random forests", Machine learning, (2001), vol. 45, No. 1, pp. 5-32.
Hall et al., "The WEKA data mining software: an update", ACM SIGKDD Explorations Newsletter, (2009), vol. 11, No. 1, pp. 10-18.

(56) References Cited

OTHER PUBLICATIONS

Rancati et ai., "Radiation dose-volume effects in the larynx and pharynx", International Journal of Radiation Oncology* Biology* Physics, (2010), vol. 76, No. 3, pp. S64-S69.
Dorr et al., "Linking the human response to unplanned radiation and treatment to the nonhuman primate response to controlled radiation and treatment", Health Phys., (2014), vol. 106, No. 1, pp. 129-134.
MacVittie et al., "The prolonged gastrointestinal syndrome in rhesus macaques: The relationship between gastrointestinal, hematopoietic, and delayed multi-organ sequelae following acute, potentially lethal, partial-body irradiation", Health Phys., (2012), vol. 103, No. 4, pp. 427-453.
Wassenaar et al., "Disparities in the clinical trial participation of adult cancer patients", J. Clin. Oncol., (2008), vol. 26, p. 9524.
Vickers, "Do we want more cancer patients on clinical trials? if so, what are the barriers to greater accrual", Trials, (2008), vol. 9, p. 31.
Abernethy et al., "Rapid-learning system for cancer care", J. Clin. Oncol., (2010), vol. 28, No. 27, pp. 4268-4274.
NCCN Clinical Practice Guidelines in Oncology. National Comprehensive Cancer Network, http://www.nccn.org/professionals/physician_gls/f_guidelines.asp. Accessed Oct. 24, 2014.
ASTRO Clinical Practice Guidelines. American Society for Radiation Oncology. https://www.astro.org/Ciinical-Practice/Guidelines/Index.aspx. Accessed Oct. 24, 2014.
ASCO Guidelines. American Society of Clinical Oncology, http://www.asco.org/quality-guidelines/guidelines. Accessed Oct. 24, 2014.
Lambin et al., "Predicting outcomes in radiation oncology: Multifactorial decision support systems", Nat. Rev. Clin. Oncol., (2013), vol. 10, No. 1, pp. 27-40.
Mortensen et al., "Aspiration pneumonia in patients treated with radiotherapy for head and neck cancer", Acta Oncol., (2012), vol. 52, No. 2, pp. 270-276.
Gómez-Millán et al., "Competing causes of death in patients with locoregionally advanced head and neck cancer treated with concomitant boost radiation plus concurrent weekly cisplatin", Clin. Transl. Oncol., (2013), vol. 15, No. 4, pp. 321-326.
Ferlito et al., "Causes of death of patients with laryngeal cancer", Eur. Arch. Otorhinolaryngol., (2014), vol. 271, No. 3, pp. 425-434.
Quon et al., "Swallow function in patients with oropharyngeal squamous ceil carcinomas treated with radiation therapy dose de-escalation", Int. J. Radiat. Oncol. Biol. Phys., (2013), vol. 87, No. 2, pp. S141-S142.
Quon et al., "Effective pain management of mucositis with prophylactic gabapentin in the irradiated head and neck cancer patient is associated with functional benefits", Int. J. Radiat. Oncol. Biol. Phys., (2014), vol. 90, No. 1, pp. S559-S560.
Starmer et al., "Effect of gabapentin on swallowing during and after chemoradiation for oropharyngeal squamous cell cancer", Dysphagia, (2014), vol. 29, No. 3, pp. 396-402.
Nutting et al., "Parotid-sparing intensity modulated versus conventional radiotherapy in head and neck cancer (PARSPORT): a phase 3 muiticentre randomised controlled trial", Lancet Oncol., (2011), vol. 12, No. 2, pp. 127-136.
Gupta et al., "Three-dimensional conformal radiotherapy (3D-CRT) versus intensity modulated radiation therapy (IMRT) in squamous cell carcinoma of the head and neck: A randomized controlled trial", Radiother. Oncol., (2012), vol. 104, No. 3, pp. 343-348.
Pauloski et al., "Comparison of swallowing function after intensity-modulated radiation therapy and conventional radiotherapy for head and neck cancer", Head Neck, (2014), pp. 1-8.
Tan et al., "Quality of life in nasopharyngeal cancer (NPC) patients: study of salivary flow recovery pattern on xerostomia improvement for intensity modulated radiation therapy (IMRT) versus volumetric modulated arc therapy (VMAT)", Int. J. Radiat. Oncol. Biol. Phys., (2014), vol. 90, No. 1, pp. S525.
Adams et al., "Objective and subjective changes in voice quality after radiotherapy for early (T1 or T2, N0) laryngeal cancer: A pilot prospective cohort study", Head Neck, (2013), vol. 35, No. 3, pp. 376-380.
Tuomi et al., "Effects of voice rehabilitation after radiation therapy for iaryngeai cancer: a randomized controlled study", Int. J. Radiat. Oncol. Biol. Phys., (2014), vol. 89, No. 5, pp. 964-972.
McQuestion et al., "The changed meaning of food: Physical, social and emotional loss for patients having received radiation treatment for head and neck cancer", Eur. J. Oncol. Nurs., (2011), vol. 15, No. 2, pp. 145-151.
Nguyen et ai., "Mechanisms of taste bud cell loss after head and neck irradiation", J. Neurosci., (2012), vol. 32, No. 10, pp. 3474-3484.
Marks et al., "Guest editor's introduction to QUANTEC: A users guide", Int. J. Radiat. Oncol. Biol. Phys., (2010), vol. 76, pp. S1-S2.
Bentzen et al., "Quantitative analyses of normal tissue effects in the clinic (QUANTEC): An introduction to the scientific issues", Int. J. Radiat. Oncol. Biol. Phys., (2010), vol. 76, pp. S3-S9.
Deasy et al., "Improving normal tissue complication probability models: The need to adopt a "data-pooling" culture", Int. J. Radiat. Oncol. Biol. Phys., (2010), vol. 76, pp. S151-S154.
Moore et al., "Vision 20/20: Automation and advanced computing in clinical radiation oncology", Med. Phys., (2014), vol. 41, No. 1, 010901.
Kawamoto, "improving clinical practice using clinical decision support systems: a systematic review of trials to identify features crltical'to success", BMJ, (2005), vol. 330, No. 7494, p. 765-0.
Brown et al., "Protocol for a randomized controlled trial of early prophylactic feeding via gastrostomy versus standard care in high risk patients with head and neck cancer", BMC Nurs., (2014), vol. 13, No. 1, p. 17.
Langius et al., "More than 10% weight loss in head and neck cancer patients during radiotherapy is independently associated with deterioration in quality of life", Nutr. Cancer, (2013), vol. 65, No. 1, pp. 76-83.
Langius et al., "Critical weight loss is a major prognostic indicator for disease-specific survival in patients with head and neck cancer receiving radiotherapy", Br. J. Cancer, (2013), vol. 109, No. 5, pp. 1093-1099.

* cited by examiner

| Outcome | Outcome Threshold (Grade) | Organ at Risk | Total Patients | Patients with Outcome, N (%) | Normalized Volume Threshold, $V_t$ | Percent Increase in Probability (% per Gy) | Dose for 50% Probability of Outcome (Gy) | p-value |
|---|---|---|---|---|---|---|---|---|
| Dysphagia | ≥2 | Larynx | 162 | 64 (40%) | 0.05 | 10.9 | 69.1 | <0.001 |
|  | ≥1 | Pharyngeal Constrictors | 149 | 68 (46%) | 0.05 | 11.4 | 70.4 | <0.001 |
| Esophagitis | ≥2 | Esophagus | 231 | 82 (35%) | 0.05 | 5.3 | 60.2 | <0.001 |
|  |  | Larynx | 93 | 37 (40%) | 0.05 | 6.5 | 68.5 | <0.001 |
| Mucositis |  | Mandible | 358 | 201 (56%) | 0.85 | 6.1 | 19.8 | <0.001 |
|  | ≥3 | Oral Mucosa | 276 | 148 (54%) | 0.90 | 4.5 | 21.8 | <0.001 |
|  |  | Combined Parotids | 344 | 206 (60%) | 0.90 | 5.4 | 4.5 | <0.001 |
| Nausea |  | Brainstem | 376 | 156 (41%) | 0.05 | 5.2 | 42.9 | <0.001 |
|  |  | Spinal Cord | 386 | 158 (41%) | 0.20 | 7.9 | 36.5 | <0.001 |
|  | ≥2 | Mandible | 359 | 152 (42%) | 0.95 | 7.0 | 21.8 | <0.001 |
|  |  | Combined Parotids | 345 | 148 (43%) | 0.95 | 10.0 | 13.4 | <0.001 |
| Voice Changes | ≥1 | Larynx | 104 | 52 (50%) | 0.25 | 9.1 | 57.0 | <0.001 |
|  |  | Inferior Pharyngeal Constrictor | 150 | 75 (50%) | 0.25 | 8.7 | 51.8 | <0.001 |
|  |  | Superior Pharyngeal Constrictor | 102 | 52 (51%) | 0.8 | 6.9 | 49.9 | <0.001 |
| Weight Loss | ≥1 | Mandible | 340 | 181 (53%) | 0.9 | 7.2 | 19.8 | <0.001 |
|  |  | Combined Parotids | 329 | 179 (54%) | 0.9 | 8.7 | 9.6 | <0.001 |
| Xerostomia | ≥2 | Mandible | 250 | 127 (51%) | 0.95 | 8.3 | 17.9 | <0.001 |
|  |  | Oral Mucosa | 190 | 113 (59%) | 0.95 | 6.8 | 16.0 | <0.001 |
|  |  | Combined Parotids | 244 | 128 (52%) | 0.95 | 17.9 | 9.6 | <0.001 |

FIG. 2

| Site | Standard Planning | | | Automatic Planning | | |
|---|---|---|---|---|---|---|
| | Count | Exceeds | Exceeds% | Count | Exceeds | Exceeds% |
| Proximal Duodenum - D1cc | 18 | 1 | 6% | 17 | 0 | 0% |
| Proximal Duodenum - D3cc | 17 | 3 | 18% | 16 | 0 | 0% |
| Proximal Duodenum - D9cc | 17 | 6 | 35% | 16 | 1 | 6% |
| Proximal Stomach - D1cc | 20 | 0 | 0% | 17 | 0 | 0% |
| Proximal Stomach - D3cc | 20 | 1 | 5% | 17 | 0 | 0% |
| Proximal Stomach - D9cc | 20 | 1 | 5% | 16 | 0 | 0% |
| Core-D1cc | 22 | 3 | 14% | 20 | 1 | 5% |

FIG. 6

| | N(+) | N(−) | BNB | BLR | NB | LR | RF | KLB |
|---|---|---|---|---|---|---|---|---|
| Xerostomia | 275 | 89 | 0.743 | 0.737 | 0.734 | 0.731 | 0.683 | 0.700 |
| Voice Dysfunction | 8 | 91 | 0.915 | 0.905 | 0.900 | 0.896 | 0.724 | 0.596 |

FIG. 32

METHOD, SYSTEM AND COMPUTER-READABLE MEDIA FOR TREATMENT PLAN RISK ANALYSIS

CROSS REFERENCE TO RELATED APPLICATIONS

This application claims priority to U.S. Provisional Patent Application Nos. 61/993,621, filed May 15, 2014; 62/022,429, filed Jul. 9, 2014; and 62/088,052, filed Dec. 5, 2014, which are hereby incorporated herein by reference in their entirety.

TECHNICAL FIELD

The invention relates to treatment plan risk analysis and to systems, methods and computer readable media thereof.

BACKGROUND

The relationship between radiation dose and treatment related toxicities is complex due to the 3-dimensional (3D) nature of the dose distribution and the complex function of the anatomy of the patient involved. For decades we have studied the impact of radiation related toxicities to whole organs identified by radiation oncologists during the treatment planning. The results have molded the practice of radiation oncology and are critical to the understanding of our medicine. To this point it has been impractical to refine the analysis to the finer substructure of the anatomy or to understand the impact of dosing multiple structures. 'Big Data' and improved methods of refining dosimetric analysis offer an opportunity to better understand how radiation impacts the function of normal anatomy and provide information to further reduce treatment related toxicities.

SUMMARY

A computer-implemented method of minimizing at least one treatment-related risk in a patient, the method including: providing feature data of at least one organ at risk or target volume of said patient from a database of non-transitory data stored on a data storage device of prior patients data; generating, using a data processor, a distribution of dose points of the at least one organ at risk or target volume of said patient based on said feature data; calculating, using the data processor, at least one of (i) a probability of toxicity for the at least one organ at risk or (ii) a probability of treatment failure for the at least one target volume, based on said distribution of dose points; assessing, using the data processor, a dosimetric-outcome relationship based on the calculated probability; and automatically formulating, using the data processor, a treatment plan using the dosimetric-outcome relationship to minimize the at least one treatment-related risk.

A computer system for minimizing at least one treatment-related risk in a patient, the computer system including: a memory having computer-executable instructions; and a processor that is coupled to said memory and that is configured to execute the computer-executable instructions to perform: providing feature data of at least one organ at risk or target volume of said patient from a database of non-transitory data stored on a data storage device of prior patients data; generating, using a data processor, a distribution of dose points of the at least one organ at risk or target volume of said patient based on said feature data; calculating, using the data processor, at least one of (i) a probability of toxicity for the at least one organ at risk or (ii) a probability of treatment failure for the at least one target volume, based on said distribution of dose points; assessing, using the data processor, a dosimetric-outcome relationship based on the calculated probability; and automatically formulating, using the data processor, a treatment plan using the dosimetric-outcome relationship to minimize the at least one treatment-related risk.

A non-transitory computer-readable storage medium for minimizing at least one treatment-related risk in a patient, the computer-readable medium storing computer-executable instructions that, when executed by at least one processor, cause a computer to perform: providing feature data of at least one organ at risk or target volume of said patient from a database of non-transitory data stored on a data storage device of prior patients data; generating, using a data processor, a distribution of dose points of the at least one organ at risk or target volume of said patient based on said feature data; calculating, using the data processor, at least one of (i) a probability of toxicity for the at least one organ at risk or (ii) a probability of treatment failure for the at least one target volume, based on said distribution of dose points; assessing, using the data processor, a dosimetric-outcome relationship based on the calculated probability; and automatically formulating, using the data processor, a treatment plan using the dosimetric-outcome relationship to minimize the at least one treatment-related risk.

Additional features, advantages, and embodiments of the invention are set forth or apparent from consideration of the following detailed description, drawings and claims. Moreover, it is to be understood that both the foregoing summary of the invention and the following detailed description are examples and are intended to provide further explanation without limiting the scope of the invention as claimed.

BRIEF DESCRIPTION OF THE DRAWINGS

FIG. 2 shows notable dose-toxicity relationships, according to an embodiment of the invention.

FIG. 6 shows results of automatic planning, according to an embodiment of the invention.

FIG. 32 shows area under the curve (AUC) for machine learning algorithms from FIG. 31, according to an embodiment of the invention.

DETAILED DESCRIPTION

Figure 1:
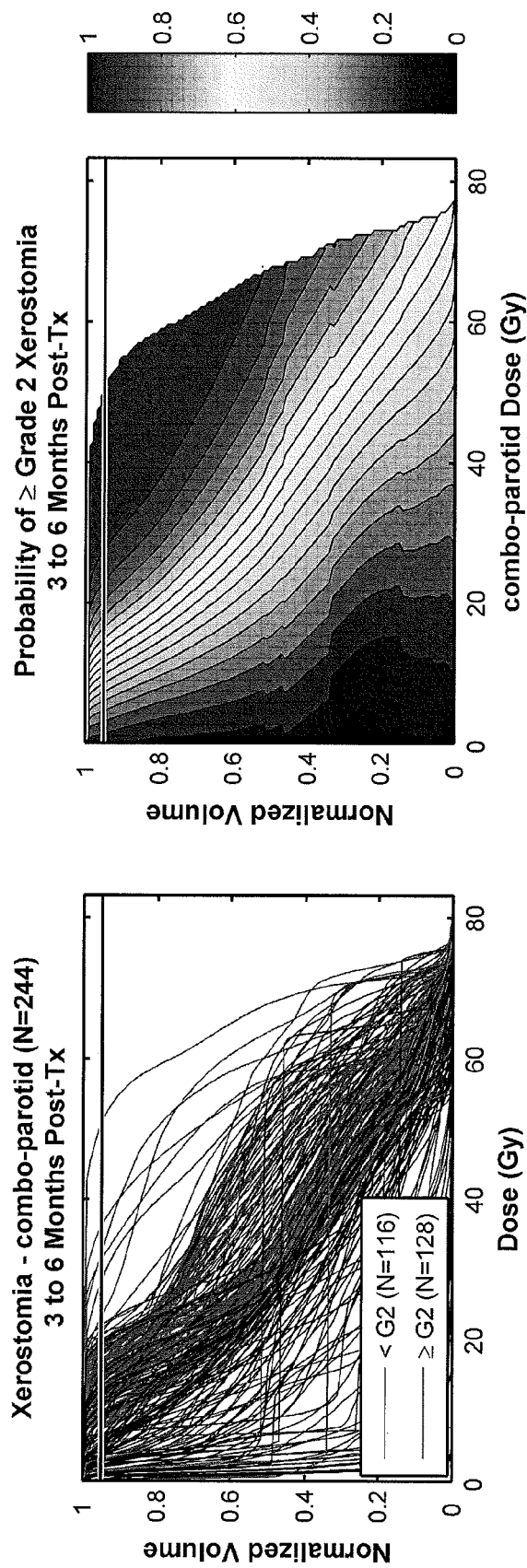
FIG. 1 reflects DVH curves for the combined parotids (left) and corresponding probability surface for grade 2 or greater xerostomia, according to an embodiment of the invention.
Figure 3:
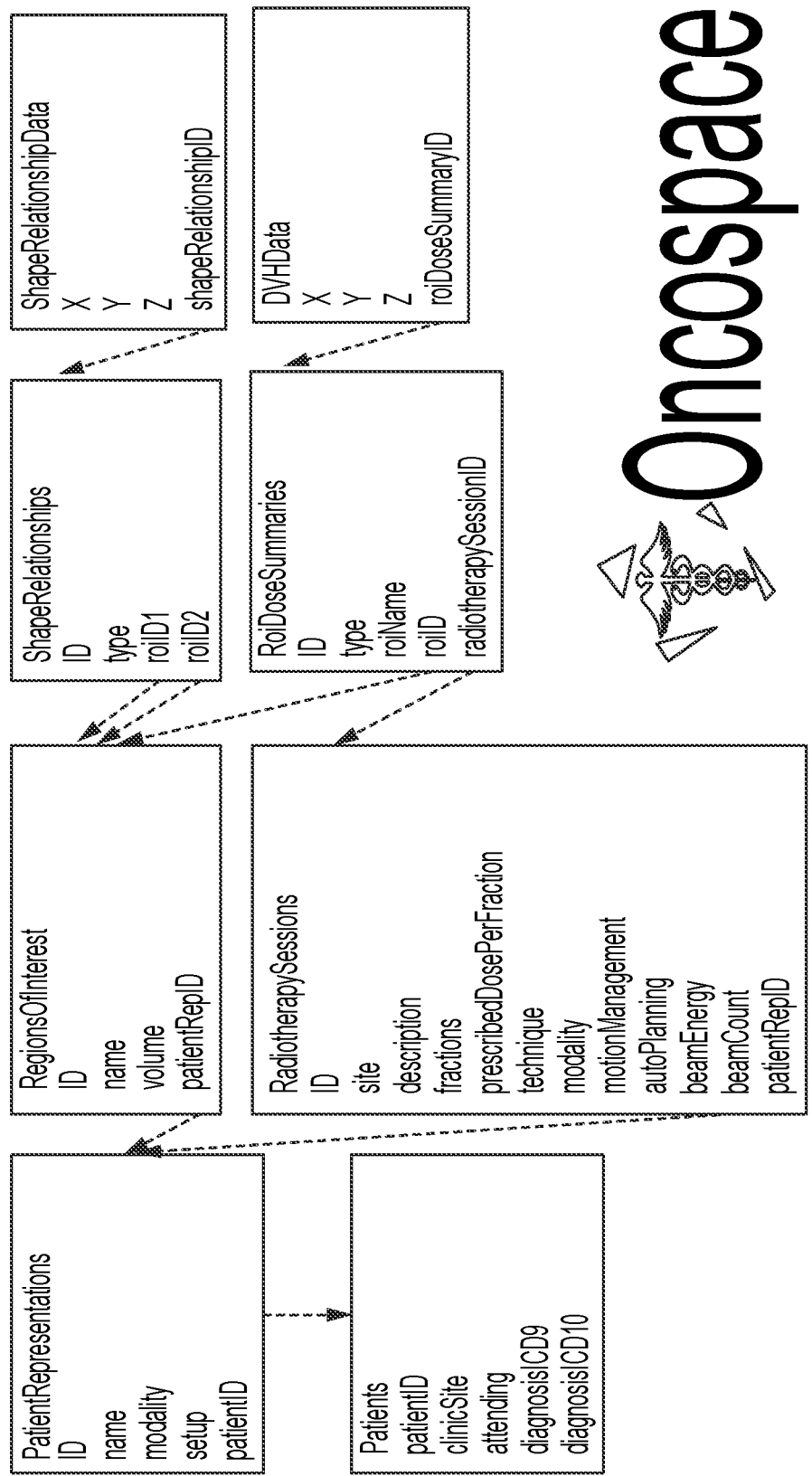
FIG. 3 shows a patient database, according to an embodiment of the invention.

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® NT/98/2000/XP/Vista/Windows 7/8/etc. available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but is not limited to) a hard disk drive and/or a removable storage drive, representing a floppy diskette drive, a magnetic tape drive, an optical disk drive, a compact disk drive CD-ROM, flash memory, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface.

Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

The computer may also include an input device which may include any mechanism or combination of mechanisms that may permit information to be input into the computer system from, e.g., a user. The input device may include logic configured to receive information for the computer system from, e.g. a user. Examples of the input device may include, e.g., but not limited to, a mouse, pen-based pointing device, or other pointing device Such as a digitizer, a touch sensitive display device, and/or a keyboard or other data entry device (none of which are labeled). Other input devices may include, e.g., but not limited to, a biometric input device, a Video source, an audio Source, a microphone, a web cam, a Video camera, and/or other camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions (e.g., for example, a field programmable gate array (FPGA)). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CATS, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

Since the seminal paper of B. Emami, J. Lyman, A. Brown, et al., "Tolerance of normal tissue to therapeutic irradiation," Int. J. Radiat. Oncol. Biol. Phys. 21, 109-122 (1991), which is herein incorporated by reference in its entirety, many publications have helped to advance our understanding of normal tissue tolerance doses in radiotherapy. These efforts culminated in the comprehensive QUANTEC report of 2010, S. M. Bentzen, L. S. Constine, J. O. Deasy, et al., "Quantitative analyses of normal tissue effects in the clinic (QUANTEC): An introduction to the scientific issues," Int. J. Radiat. Oncol. Biol. Phys. 76, S3-S9 (2010), which is herein incorporated in its entirety by reference. Quantec not only summarizes common normal tissue effects but also highlighted obstacles to a more advanced understanding of these effects. One particularly important charge was the "[e]stablishment of large continually growing databases" to facilitate the collection and permanent storage of vast amounts of information required for dosimetric-outcome analyses. This has been made possible through the development of an in-house, analytic oncology database that has been routinely populated at our institution over the last 7 years. With such a vast amount of information already contained within this database, analysis tools for large-scale evaluation of dose-toxicity relationships are disclosed.

By housing a database of prior patients, it is possible to determine risks for new patients by either modeling or querying data from the database to determine risk models that can be applied to a new patient. Each risk such as Xerostomia or dysphagia depends on a certain information about the patient which includes treatment plan features Such as proximity of targeted tissues to normal functional anatomy, radiation dose delivered to normal anatomy or clinical factors such as diagnosis, Karnofsky performance status or surgical or medication histories as well as demographic data Such as gender, age or race. The invention provides a means to evaluate the risks for an individual patient based on the data provided in the database (either via a model derived from the data or from accessing the data directly). The risk evaluation may be made based on the proximity of critical structures to target volumes with all the clinical and demographic information to provide input to the automated treatment planning. See U.S. Application Ser. No. 61/909,937, the content of which is herein incorporated by reference in its entirety. Secondly, the risk evaluation can be used, including the planned dose, to evaluate a candidate treatment plan for potential risks. Thirdly, with each new patient treated, the system improves its knowledge base by adding the new patient to the database to refine the model.

We currently assess our plan quality by evaluating the dose to the critical structures through dose volume histograms (DVH) which fail to consider where the higher doses are within the critical structure. This project seeks to refine the analysis to help us understand what parts of the critical structures are more or less important.

Current practice crudely estimates radiation induced toxicity risk with simple dose-volume criteria to whole organs at risk (OAR). Enhanced or decreased toxicity risk due to patient related factors (e.g. chemo, baseline status, symptom susceptibility and tolerance) are considered in an ad hoc manner. Knowledge base from continual collection of clinical data provides opportunity to learn from clinical experience and apply the knowledge clinically. DVH assumes that every sub-region of an OAR has the same radiosensitivity and functional importance to the related toxicity. DVH assumes that each OAR is uniquely responsible for the overall human function related to the toxicity.

The whole organ DVH vs Toxicity relationship can be noisy and variable. Evidence on parotid dose shows more importance on superior portions in relation to xerostomia. Swallowing function vs dose to muscles also plays a factor. Other clinical factors can compound analysis.

Are there regions of a given structure that are more sensitive than others? Or are there combinations of regions that make a difference to overall function? Xerostomia may involve a combination of regions of parotid and submandibular glands and portions of each of these glands may be more sensitive than others to the actual patient function. See Buettner et al., "Novel approaches to improve the therapeutic index of head and neck radiotherapy: An analysis of data from the PARSPORT randomised phase III trial," Radiotherapy and Oncology 103:82-87 (2012), which is herein incorporated by reference in its entirety. Dysphagia involves several muscles responsible for swallowing function. See Kumar et al., "Radiation Dose to the Floor of Mouth Muscles Predicts Swallowing Complications Following Chemoradiation in Oropharyngeal Squamous Cell Carcinoma," Oral Oncology 50:65-70 (2014), which is incorporated herein by reference in its entirety. After radiation, some of these muscles may compensate for one another, and it may be crucial to spare a particular muscle if other muscles are impacted by the disease or impossible to spare dosimetrically. Similarly, cognitive dysfunction from brain irradiation is likely impacted from more specific regions of the brain being irradiated. See Redmond et al., "Association between Radiation Dose to Neuronal Progenitor Cell Niches and Temporal Lobes and Performance on Neuropsychological Testing in Children: a Prospective Study," Neuro-Oncology 15(3):360-369 (Jan. 14, 2013), which is herein incorporated by reference in its entirety. Identifying which region(s) of the brain are involved in which impairment requires a significant amount of data to ascertain.

In 2007, we began the Oncospace program at Johns Hopkins which integrates structured data collection into the clinical environment for capturing treatment related toxicities, quality of life and outcome measures. In addition we capture the 3D dose distribution and the contoured target and normal anatomy and the relationships between them. The Oncospace database houses this data in a manner designed for analysis, which allows us to quickly analyze the dose vs toxicity relationships for our patients. The database currently houses over 700 head and neck patients with the full dosimetry, toxicity and outcome measures.

The increased success of atlases and deformable image registration to identify anatomical regions in CT or MRI images provides an opportunity to automatically define sub regions across the patients in the database. Additionally, atlas based segmentation has been used in the head and neck region (ref) to assist in contouring normal anatomy. In radiation therapy, we segment a set of structures in each anatomical region as standard of care. Given the existing set of tools and segmented structures from standard of care, we can provide methods of refining the segmentation to produce sub regions that have correspondence across the patients in the database.

A goal of one embodiment is for mining the data to provide the clusters of sub regions that most impact a particular toxicity or outcome. Such an algorithm incorporates current knowledge through controlling what sub regions are considered, while giving enough flexibility to find what may not be known. The objective of the search would be to maximize the statistical significance of the dose to the sub regions to the outcome measure.

Some Embodiments of the Current Invention Include

Implementing an algorithm that advances the analysis of dose-toxicity relationships at the sub-organ level to identify specific portions of the organ(s) that are more or less critical and sensitive to radiation damage.

Using the algorithm to study what regions and sub-regions most impact patient related toxicities of xerostomia, dysphagia and cognitive function using our Oncospace database.

Incorporating the refined dose-toxicity relationships into the treatment planning process to reduce treatment related toxicities.

One purpose of an embodiment of the invention is to clinically deploy an interface for automatic Radiation Therapy (RT) treatment planning for patients with cancer to reduce RT treatment planning time. In this regard, plan quality can be improved by using plan data from previous RT treatments. An embodiment can also be used to improve safety by reducing protocol deviations. Another purpose is to provide a framework for automatic extraction of clinically meaningful dosimetric-outcome relationships from an in house, analytic oncology database. Further, a display protocol adherence via a coded interface may highlight values out of tolerance or at high risk. For example, a green highlight can indicate low risk of a toxicity, or a dose level within protocol tolerance. The color orange can indicate higher risk, and red can identify out of tolerance. More patient data can mean more Successful queries and more accurate assessment of risk. The automated toolkit may also enable manual edits, when prior data cannot be queried or if a specific patient deviates significantly from the normal (e.g. Surgical removal of structures).

Another purpose of an embodiment is to improve understanding of the dose vs toxicity relationships for organs at risk and their functional sub-regions. Another purpose can be to identify compounding clinical factors associated with treatment related toxicities. Another purpose can be to utilize the knowledge for risk assessment, treatment plan quality and automation, and clinical decision support.

Automatic Inverse Planning Plan Objectives can also be generated. These objectives specify the desired goals of the planning process and can be used to evaluate the quality of a plan as well as drive the computerized optimization algorithm to the overall planning objective. Objectives can be dose-based where we specify a particular dose and volume level to limit the OAR to, or the objectives can be risk-based where we estimate the risk from the dose and seek to limit it. An objective can be added from a selected prescription and/or protocol. For each objective, the lowest achievable OAR dose from the database for a given OAR volume can be selected where the target dose objectives are met and the structure has an equal or greater overlap with the target structure. Automatic planning can reduce plans that exceed protocol specifications. As indicated in FIG. 6, in one embodiment, only one automatic plan exceeded tolerance for any objective.

Figure 7:
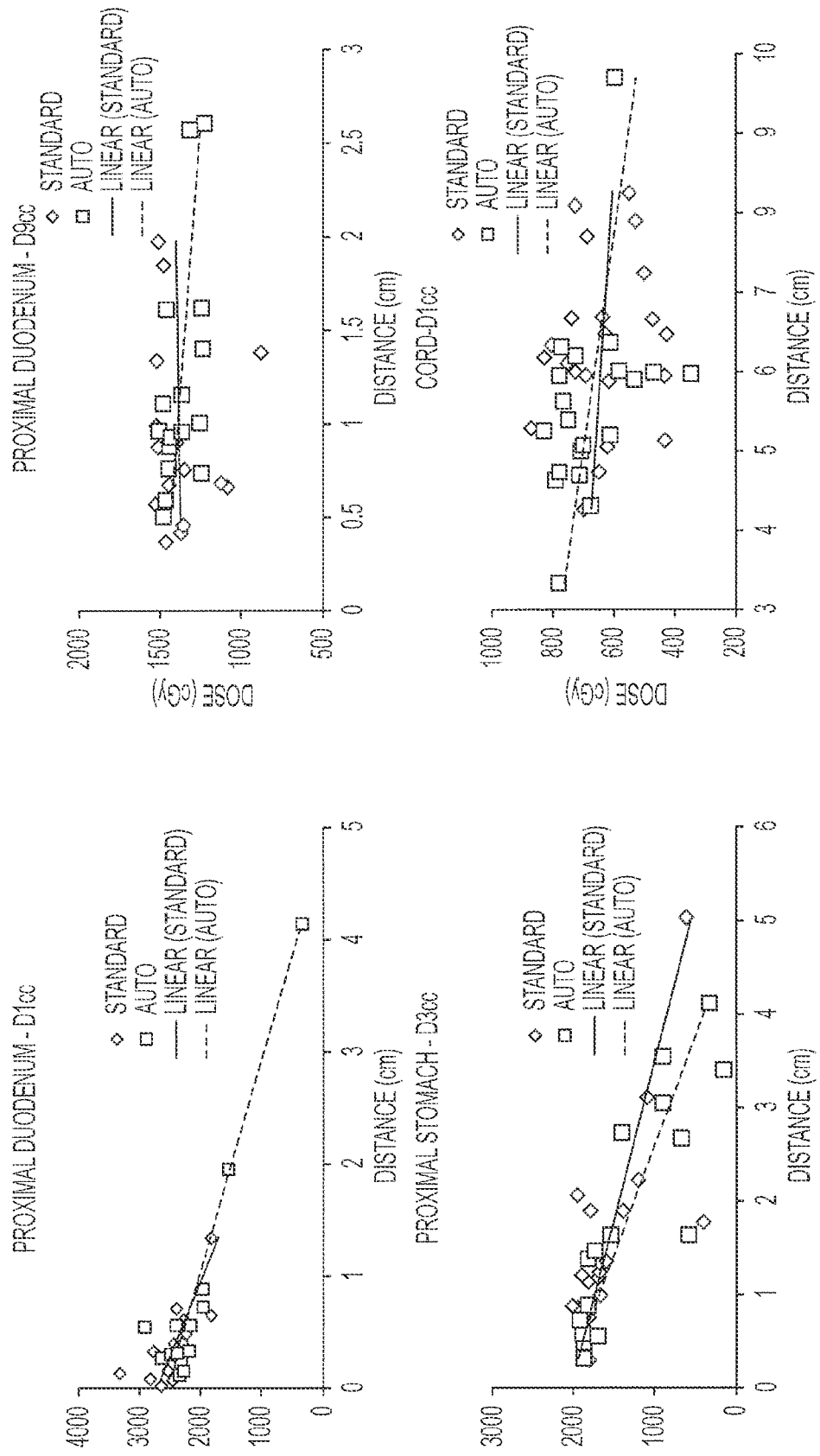
FIG. 7 shows results of automatic planning trends, according to an embodiment of the invention.
Figure 8:
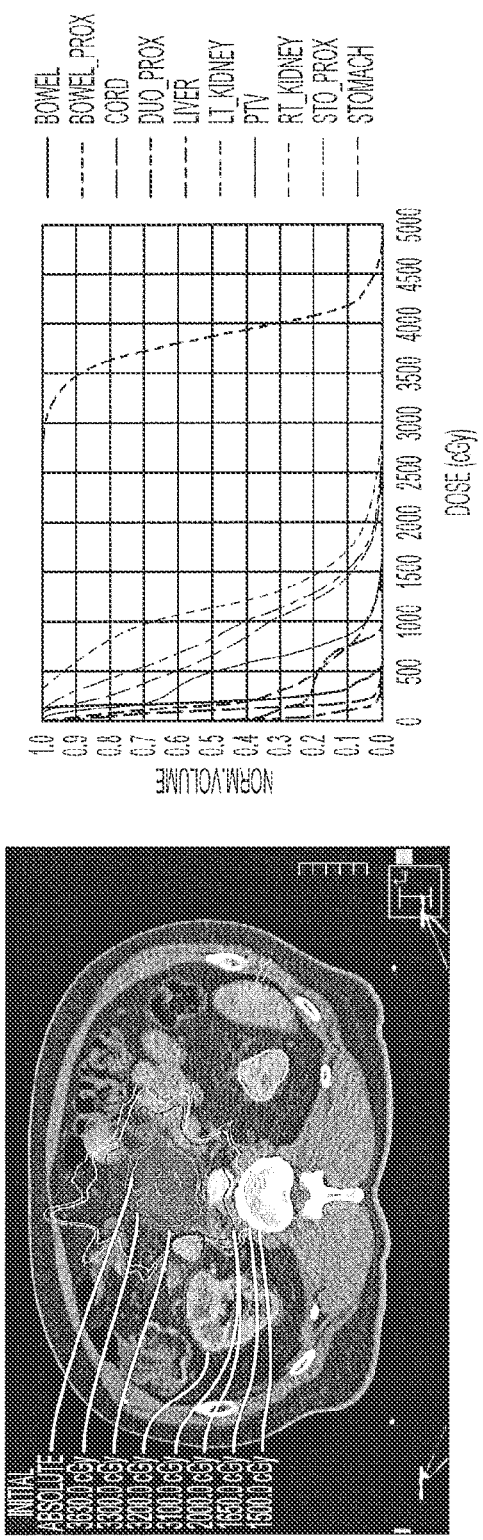
FIG. 8 shows an interface for automatic treatment planning, according to an embodiment of the invention.

As can be seen in FIG. 7, automatic planning trends towards lower dose at increasing distance from critical structures.

Low OAR objectives can be weighted. If objectives are achievable, tradeoff in optimizer can be minimized. In a plan evaluation dashboard, protocol objectives can be displayed. Compliance of these objectives can be highlighted (e.g., PASS). And the plan evaluation dashboard can be modified for new protocols and variations.

The database can have consistent naming convention. For example, database lookup can require exact matching of names (i.e., kidney_lt does not equal lt_kidney). A renaming interface can catch common alternate names. Uncommon names can be manually edited. ROI generation scripts can be used to add all structures for a given site before contouring. Names can be converted to lower case with special characters removed. Further, structures can be renamed to a common scheme. For example, the database can lookup according to a consistent structure naming (kidney_L can correspond to lt_kidney, proximal_duodenum can correspond to due_prox). The tag structure can be implemented so that a planning target volume (PTV) corresponds to target structure, OAR corresponds to critical structures, and no annotation corresponds to other structures not included in the database.

Figure 4:
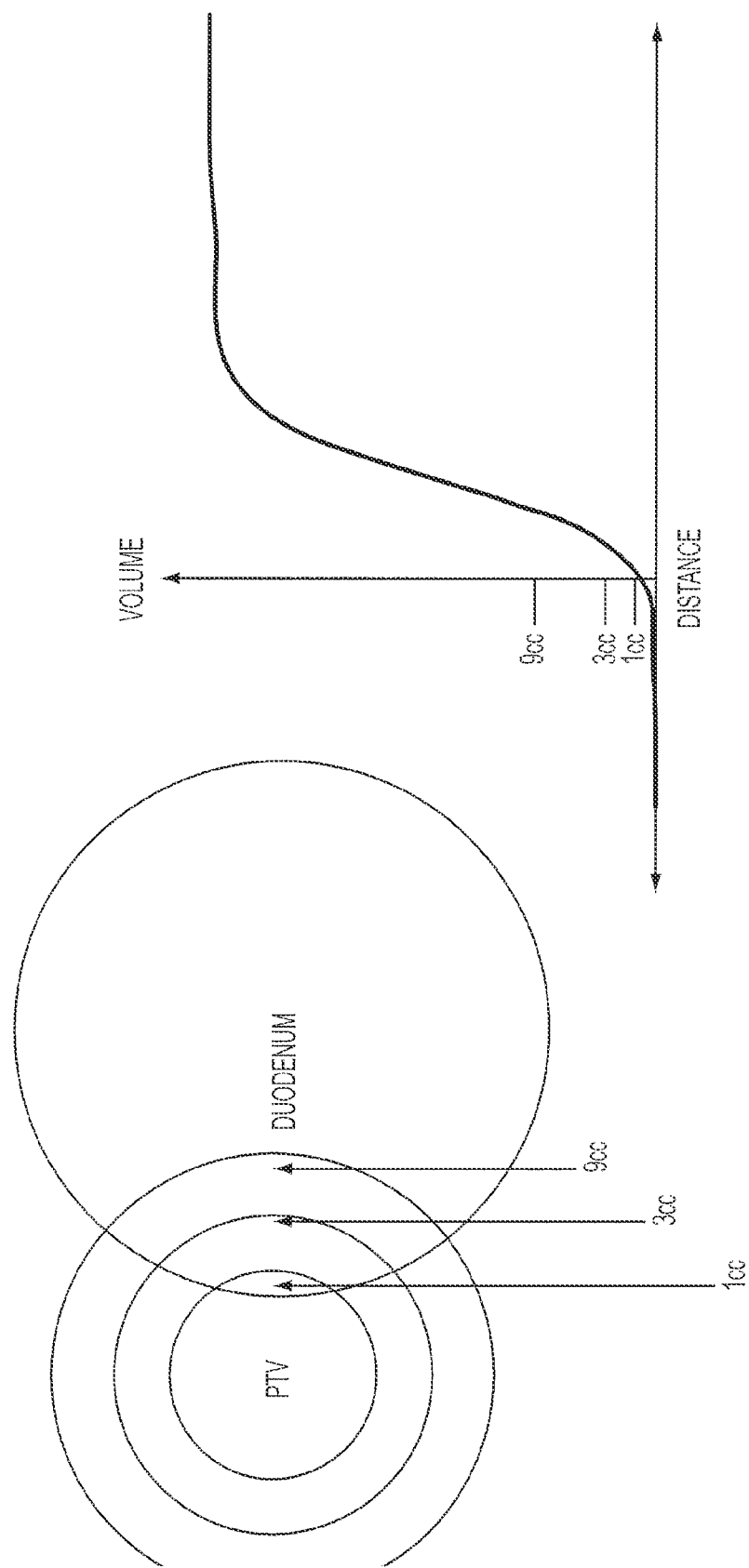
FIG. 4 shows an overlap volume histogram, according to an embodiment of the invention.

DATA ANALYSIS. An embodiment can be implemented using a Microsoft SQL Server Database. Using SQL queries, all DVH curves and outcomes having records for at least 100 patients were extracted from the database. Paired structures such as the left and right parotids were automatically combined based on OAR naming conventions and were included as additional structures in the current analysis. DVH curves were interpolated at a series of normalized volume thresholds, $V_t \in [0.01, 0.02, \ldots, 0.99]$, and the resulting distribution of dose points $D(V_t)$ was stratified according to outcome. In one embodiment, Overlap Volume Histograms (OVHs) can be used. OVH can map a shape of an OAR to a volume-distance plane though target expanding and contracting. OVH plots can be read as X % of the OAR volume is within Y cm of the target. See FIG. 4. Thus, DVH and OVHs can be used for each patient. Logistic regression was computed separately for each $D(V_t)$ using maximum likelihood estimation, with a final probability given by $P[D(V_t)] = (1 + \exp[-\beta_0 - \beta_1 \cdot D(V_t)])^{-1}$. OVH can be calculated in a range of around 86 seconds to around 158 seconds. A typical optimization time can be around 150 seconds.

Figure 5:
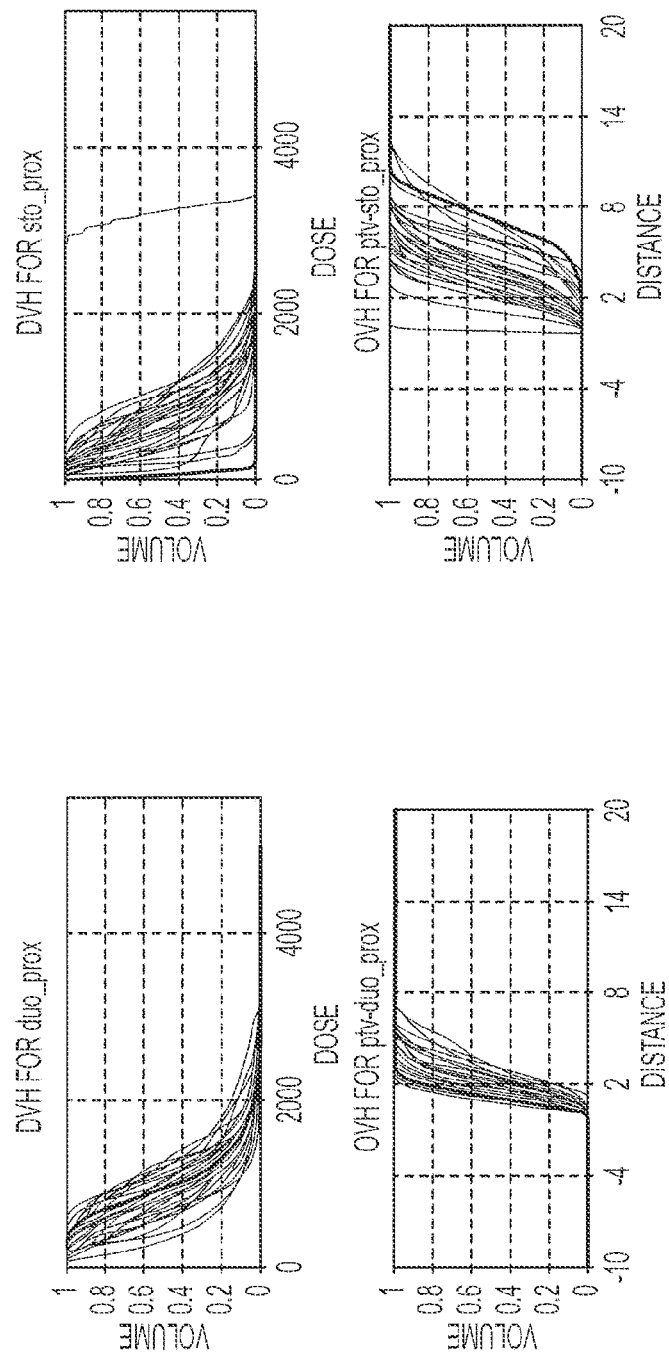
FIG. 5 shows a comparison between dose volume histogram and overlap volume histogram, according to an embodiment of the invention.

As seen from FIG. 5, Proximal Duodenum can have some volume within 2 cm of the PTV for all current patients. Dose can be much higher to the duodenum due to close proximity to PTV. Proximal Stomach can have much more variability in position. For instance, dose can be lower due to greater distance from target structure and most tumors in pancreas head, thus far from stomach.

EXAMPLES

The following includes examples of at least one embodiment of the invention, but it is not intended to limit the invention to the following examples. An embodiment of the current invention can establish a data-mining framework in which treatment planning data and normal tissue complication effects in an integrated, analytic oncology database can be efficiently and automatically formulated into meaningful clinical recommendations.

Dose-volume histograms (DVH) and clinical outcome-related structured data elements have been routinely stored to our database for 513 HN cancer patients treated from 2007 to 2014. SQL queries were developed to extract outcomes that had been assessed for at least 100 patients, as well as DVH curves for organs-at-risk (OAR) that were contoured for at least 100 patients. DVH curves for paired OAR (e.g., left and right parotids) were automatically combined and included as additional structures for analysis. For each OAR-outcome combination, DVH dose points, $D(V_t)$, at a series of normalized volume thresholds, $V_t = [0.01, 0.99]$, were stratified into two groups based on outcomes after treatment completion. The probability, $P[D(V_t)]$, of an outcome was modeled at each $V_t$ by logistic regression. Notable combinations, defined as having $P[D(V_t)]$ increase by at least 5% per Gy (p<0.05), were further evaluated for clinical relevance using a custom graphical interface.

The strength of the dosimetric-outcome relationship can be assessed as the increase in probability per Gy from treatment planning, computed numerically as $\exp(\beta_1)$. For example, the horizontal line in FIG. 1 reflects the distribution of dose points at 95% of the combined parotid volume. Parameter $\beta_1 = 0.1650$ implies an increase in the probability of grade 2 or greater xerostomia of $\exp(\beta_1) = 1.179$, or 17.9% per Gy from treatment planning (p<0.001). In this case, a dose of 9.6 Gy to 95% of the combined parotids resulted in a 50% probability of grade 2 or greater xerostomia.

To filter the large number of initial OAR-outcome combinations, regression results were further evaluated only if the strength of the dose-outcome relationship was significant (p<0.05) and increased by more than 5% per Gy.

Results: A total of 57 individual and combined structures and 115 outcomes were queried, resulting in over 6,500 combinations for analysis. Of these, 528 combinations met the 5%/Gy requirement, with further manual inspection revealing a number of reasonable models based on either reported literature or proximity between neighboring OAR. The data mining algorithm confirmed the following well-known toxicity/outcome relationships: dysphagia/larynx, voice changes/larynx, esophagitis/esophagus, xerostomia/combined parotids, and mucositis/oral mucosa. Other notable relationships included dysphagia/pharyngeal constrictors, nausea/brainstem, nausea/spinal cord, weight-loss/mandible, and weight-loss/combined parotids.

DATA COLLECTION. To date, treatment planning and outcomes-related data has been prospectively collected for 513 HN cancer patients. 53 patients in a multi-institutional Pancreas SBRT Trial have been used. In one embodiment, a large patient population is preferred. Initial results used a database of only 14 patients. OVH was calculated in around 122 seconds. In this embodiment, the patients had 37 standard plans and 29 automatic plans. Average optimizations that were required for standard planning was 40+/−42. Average optimizations required for automatic planning was 27+/−26. Thus, there was large variability in required optimizations, and more patients were desired for statistically significant results. Increasing the database population can result in more reliable database queries. Higher quality patient plans in the database result in higher quality plans for new patients. Treatment planning data, including dose-volume histograms (DVH) and radiotherapy prescription details (number of fractions, dose per fraction, etc.), were imported into the database after treatment completion to ensure that patients had received all treatment fractions. Data integrity was further promoted through a graphical user interface to verify an organ at risk (OAR) and plan naming conventions. This interface also enabled data transfer from the treatment planning system directly into the database. To collect clinical data, a second, web-based interface can be used to collect structured data elements directly from patients during each on-treatment and follow-up appointment. Primary sources of clinical data included established toxicity measures (FIG. 2) and quality-of-life questionnaires.

Thus, prediction of toxicity or outcome risk from Dose Volume Histogram (DVH) can be determined. The prediction can also take into consideration treatment related toxicities, quality of life outcomes and disease outcomes. The prediction can be based on other clinical factors such as age, race, concurrent therapies, disease location, histology, social and medical history (e.g. smoking, or HPV status). The prediction of the toxicity or outcome based on the relationship between critical organ and the target volume (e.g. Overlap Volume Histogram (OVH) or other shape relationships) to inform risk prior to planning as DVH is only known during and after planning.

Figure 9:
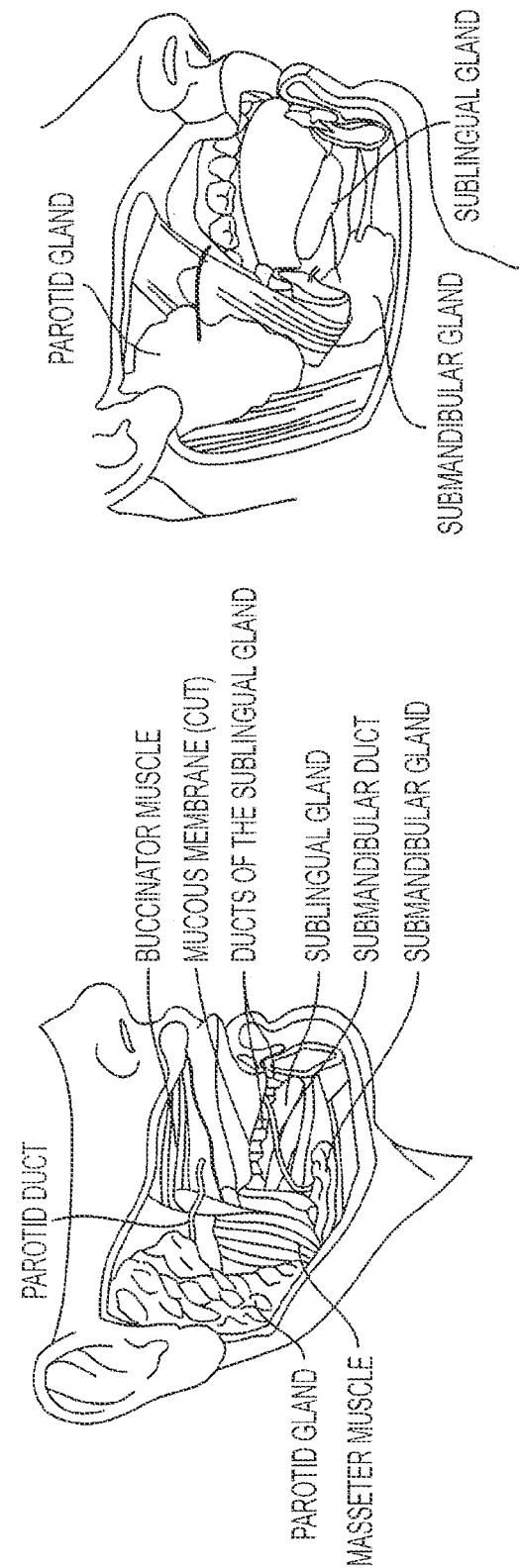
FIG. 9 shows different tissues associated with Xerostomia, according to an embodiment of the invention.
Figure 10:
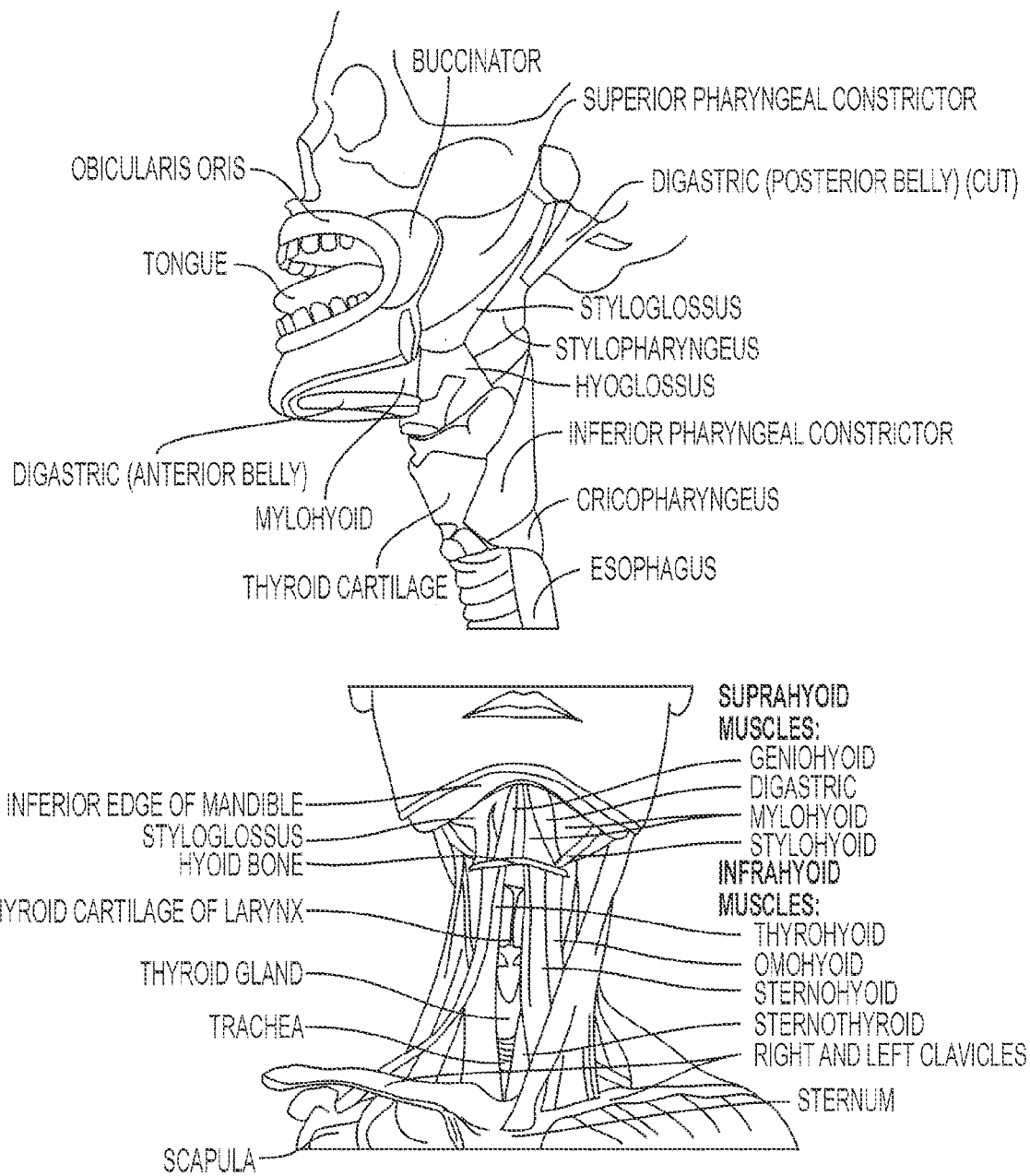
FIG. 10 shows different tissues associated with Dysphagia, according to an embodiment of the invention.
Figure 11:
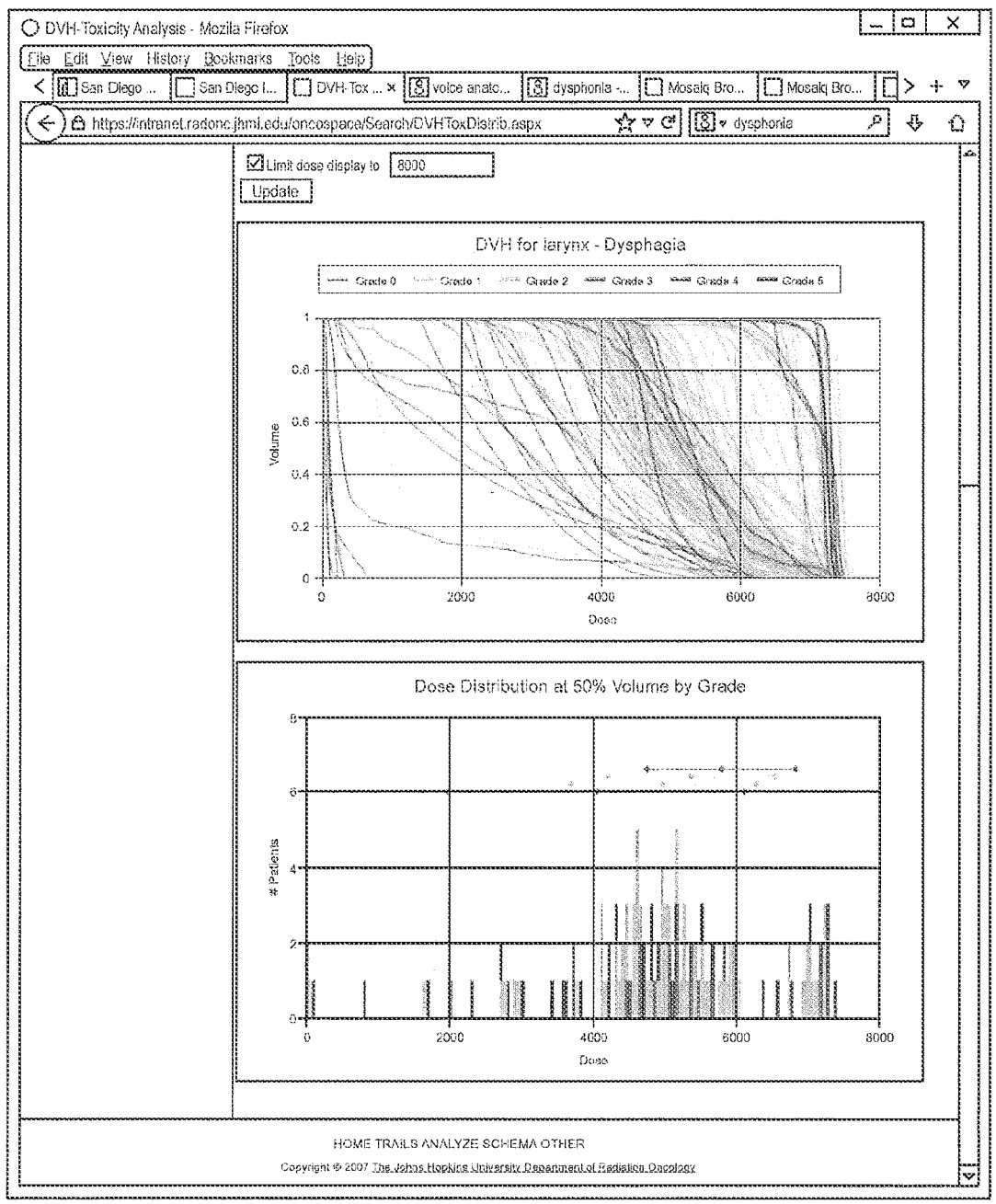
FIG. 11 shows a DVH representation of larynx and a dose distribution representation at 50% volume by grade for Dysphagia, according to an embodiment of the invention.
Figure 12:
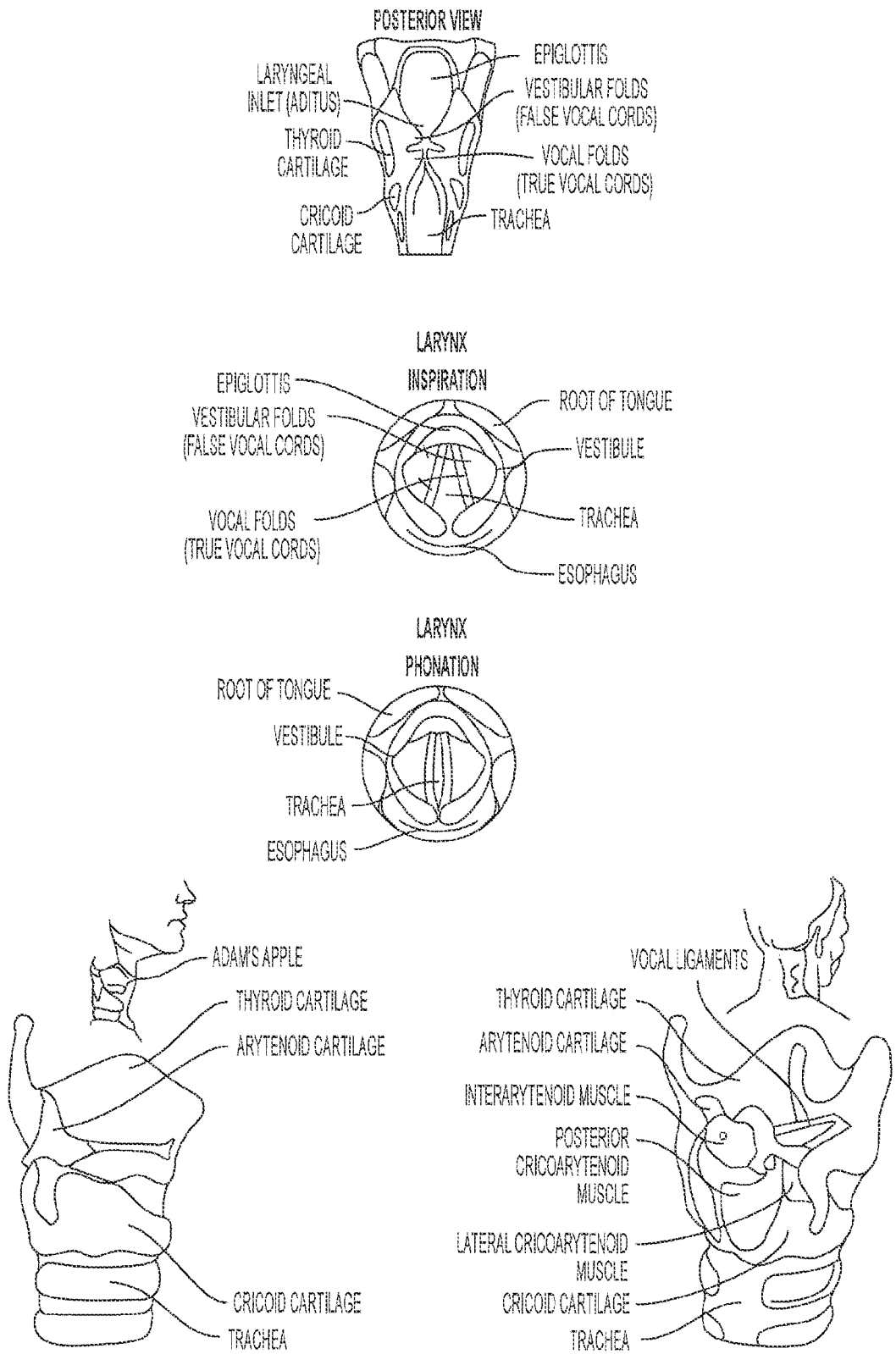
FIG. 12 shows a representation of tissues associated with voice change, according to an embodiment of the invention.
Figure 13:
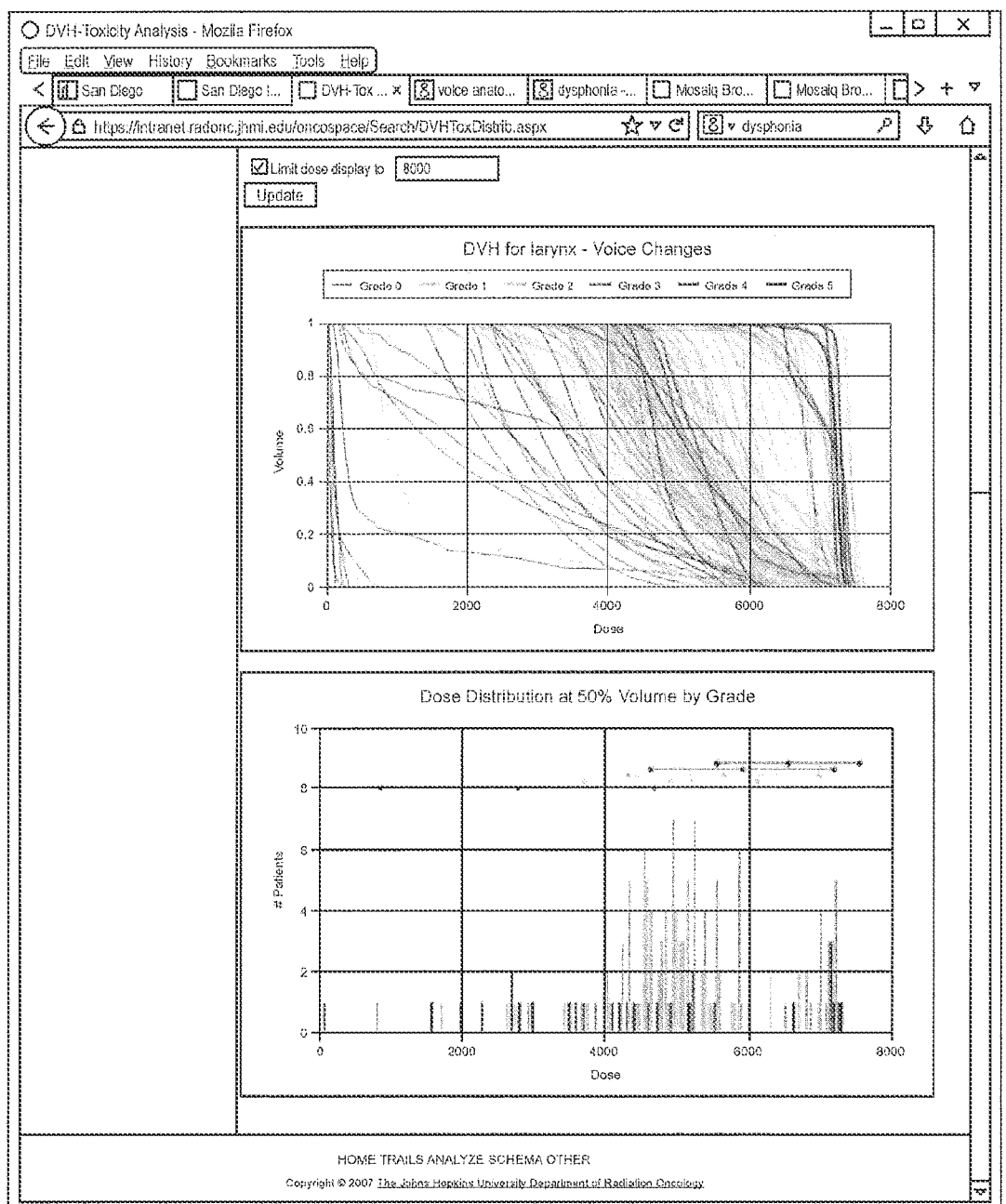
FIG. 13 shows a representation of DVH for larynx—voice changes, and a dose distribution at 50% volume by grade, according to an embodiment of the invention.
Figure 14:
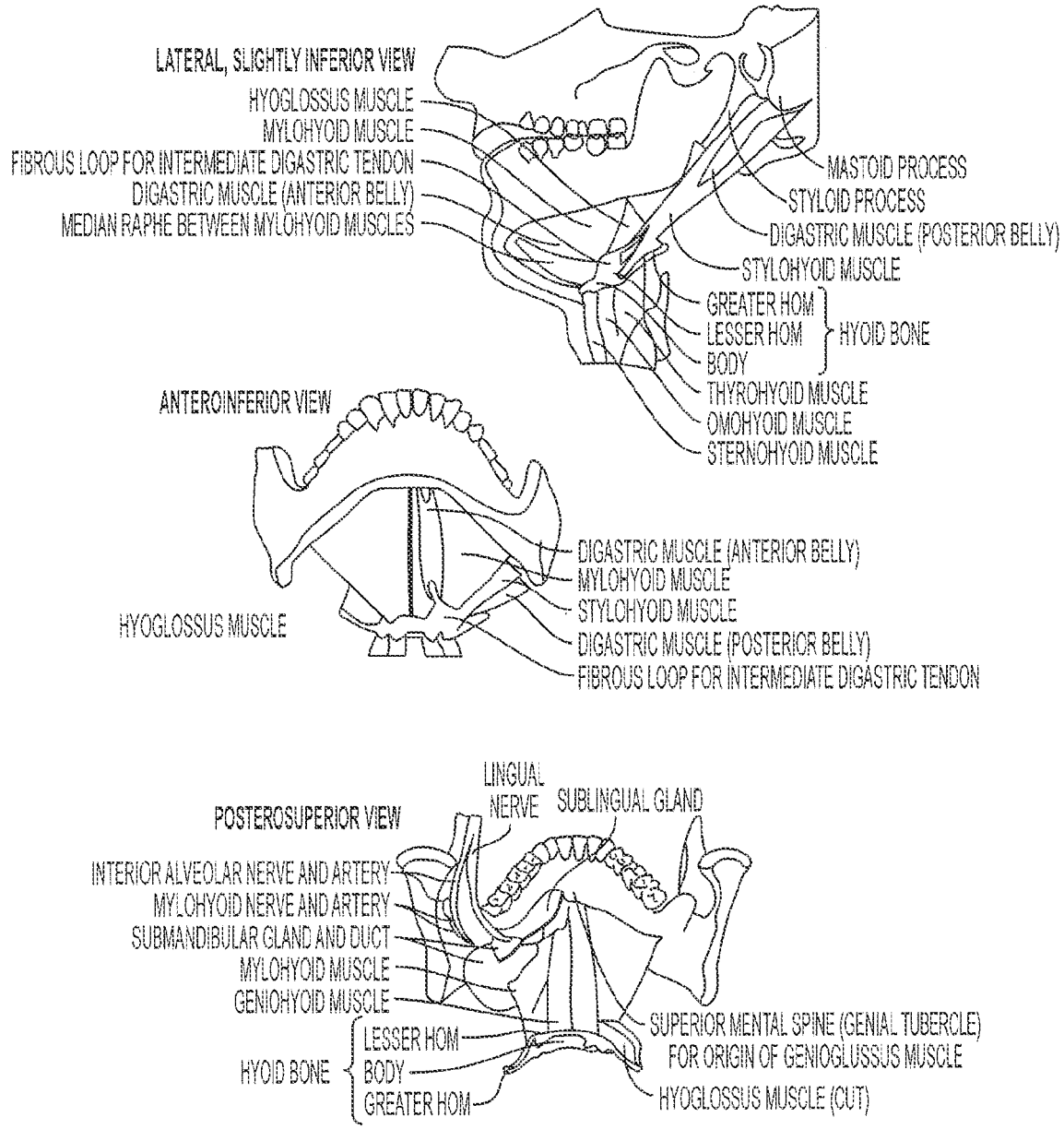
FIG. 14 shows a representation of tissues associated with Trismus, according to an embodiment of the invention.
Figure 15:
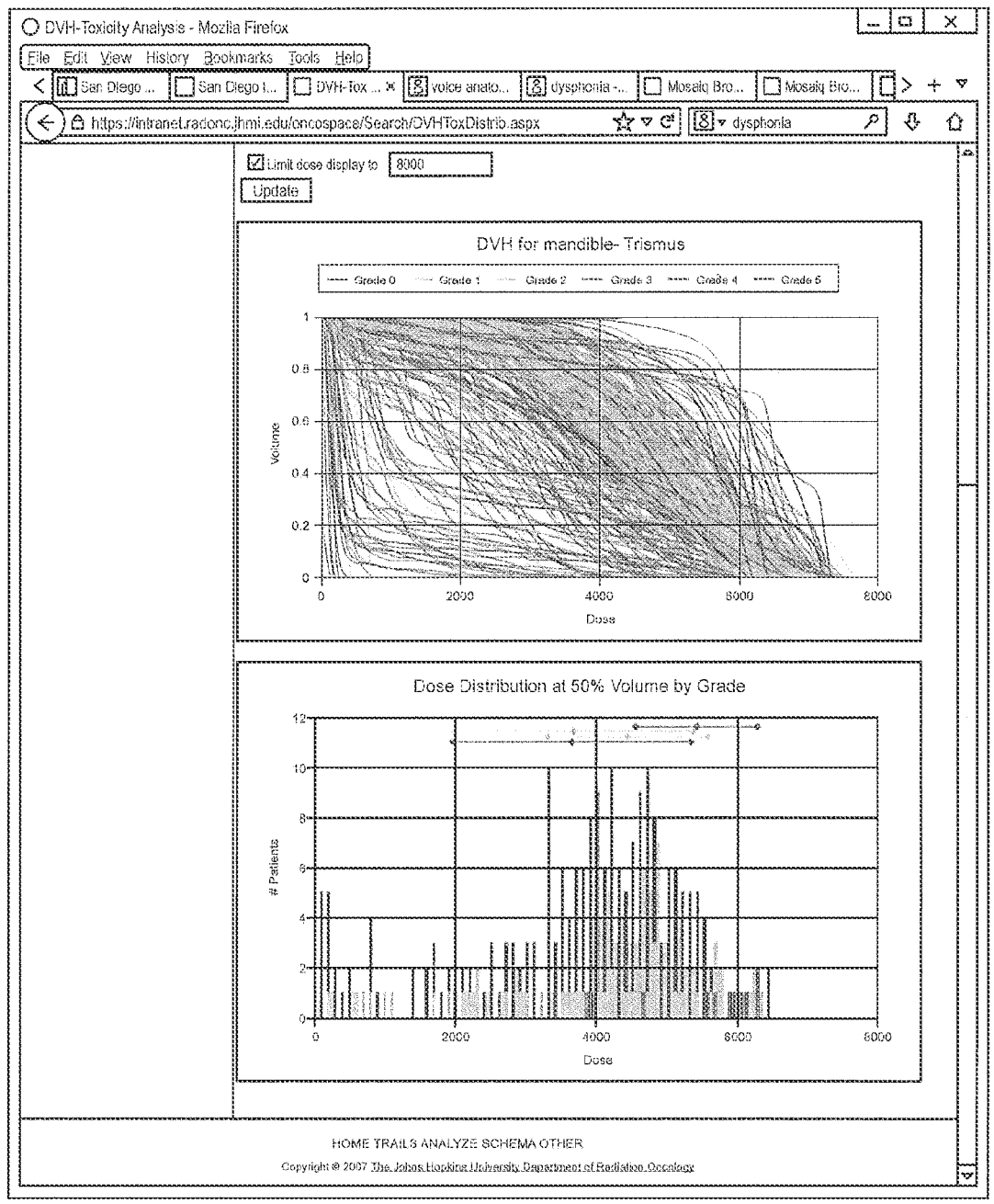
FIG. 15 shows a representation of DVH for mandible—Trismus and a dose distribution at 50% volume by grade, according to an embodiment of the invention.

FIG. 9 shows different tissues associated with Xerostomia. FIG. 10 shows different tissues associated with Dysphagia. FIG. 11 shows a DVH representation of larynx and a dose distribution representation at 50% volume by grade for Dysphagia. FIG. 12 shows a representation of tissues associated with voice change. FIG. 13 shows a representation of DVH for larynx—voice changes, and a dose distribution at 50% volume by grade. FIG. 14 shows a representation of tissues associated with Trismus. FIG. 15 shows a representation of DVH for mandible—Trismus and a dose distribution at 50% volume by grade.

By way of example, using an offensive strategy analogy, if we wanted to destroy military factory and we didn't know the functional subunits, we carpet bomb. Alternatively if we know functional model, we can strategically place bombs to limit destruction and destroy overall function. The inverse is true for critical structures in RT where we want to protect critical parts. By further analogy, using defensive strategy as an analogy, to protect we can limit broad based destruction. We can also provide extra protection of critical subunits. We can analyze redundant factories or surrender one for protection of others. We can ask how critical is overall function to survival? And we can surrender it for preservation of more critical function.

In a data mining approach that involves clustering, one embodiment of the invention has results assessing treatment plans involving xerostomia and dysphagia. In one embodiment, a model to refine analysis of dose to sub-regions is implemented. Some results show models for sub-region or multi-OAR segmentation and knowledge of critical region clusters. This embodiment may provide a framework for experimentation of all OARs.

In one embodiment, a broad based dose vs toxicity data mining technique is used. A sub-region clustering for selected toxicities may be used. For Xerostomia, tissues of parotid, submandibular and sublingual may be analyzed. For Dysphagia, larynx and swallow muscle groups may be analyzed. The method may include clinical factors such as Chemo, HPV, Age, Baseline Toxicity, KPS, Smoking. Further, a model for assessment of individualized importance of risks can be implemented. Further, knowledge can be included into the treatment plan evaluation and automation.

Refined dose painting to avoid critical sub regions can lead to lower toxicity rates in radiotherapy. By incorporating clinical factors, radiation toxicities should refine risks for 'similar' patients. Clinical decisions influencing risk can be individualized for a patient. Automation/quality control of treatment planning can be implemented incorporating patient risk assessment.

In one embodiment, the data mining approach can establish importance of select toxicities. It can also establish definitive evidence that the sub region analysis will improve toxicity related outcome. Further, it can establish importance of individualizing risk decisions. Next, it can establish importance of risk inclusion into the plan quality and review process.

The data mining approach may also be used on PTV. The method may be used to target volumes to look for more critical areas of tumor that result in improved disease control. The method may also be used in prophylactic neck region.

Thus, one embodiment evaluates risk based on the dose to 'subregions' of a set of critical structures. This can be an alternative to DVH where the data can be used to understand what portions of the set of critical structures may be more or less critical to the toxicity or outcome and is the topic of our current research. For example, salivary function is provided by the parotid, submandibular and sublingual glands. By breaking the entire set of glands up into smaller subregions and evaluating salivary function of prior patients, we expect to find a set of those sub regions that is most critical to salivary function refining our identification of regions to avoid, as well as identifying the importance of these 'sub-regions' to risk prediction.

An intermediate mathematical model of toxicity risk can be created from the database that could be used independently of the database to predict the risk.

In one embodiment, an ability of both the database and any intermediate model can be achieved to be able to learn from new data, so each new patient added improves the knowledge in the database. Further, an ability to assess patient specific risk tolerances as input can be achieved to the auto-planning. One patient may be more concerned with incontinence over impotence. Or the patient may be blind in one eye already so it is more important to maintain vision in the other eye. Further, an ability to automatically plan an intensity modulated radiotherapy treatment plan to best align (or minimize) the toxicity or outcome risk for a new patient base on the risk models above can be achieved.

RESULTS. FIG. 2 provides some of the most notable dose-outcome relationships from the DVH analysis. Dysphagia, esophagitis, and voice changes were predominantly affected by high doses to small volumes of the larynx, esophagus, and pharyngeal constrictors. In contrast, mucositis and xerostomia primarily depended on low doses delivered to large volumes of the combined parotid tissue, oral mucosa, and mandible. Nausea was closely related to low doses in large volumes of the mandible and combined parotids as well as high doses in small volumes of the brainstem and spinal cord. Finally, weight loss was most associated with low doses to large volumes of the mandible and combined parotid, with an additional dependence on dose to the superior pharyngeal constrictor.

Regarding dosimetry, an acceptable treatment plan can quickly be reached using prior patient information. After auto planning, plans can be improved manually. The database can help the physician by, for example, capturing physician intent by including previously approved treatment plans. The dashboard spreadsheet can enable quick assessment of relevant dose parameters. The database aids in research by allowing for the collection and assessment of planning data and comparison to toxicity and other patient statistics.

CONCLUSION. Our database platform can enable large-scale analysis of dose-outcome relationships. The current data-mining framework reveals both known and novel dosimetric and clinical relationships, underscoring the potential utility of this analytic approach. Multivariate models may be necessary to further evaluate the complex relationship between neighboring OARs and observed outcomes. We have established a framework for large-scale analysis of normal tissue complication effects in a continually growing database. The current data-mining algorithm has provided insight into novel dosimetric and clinical dose-toxicity relationships not otherwise observed. Future work will focus on improving the efficiency and automation with which meaningful relationships are extracted and presented as clinical recommendations. Automatic planning can speed up RT plan generation. Higher quality plans can use previously approved plans. This can provide greater safety by limiting protocol deviations. The plan evaluation dashboard can allow for dosimetrists and physicians to quickly evaluate plan quality. Adding newly approved plans to the database increases future plan quality. Naming must be consistent to use tools.

We use toxicity and outcome data from prior patients, so the derivation of risk is based on querying this data from the data base along with the DVH. This data is added back to database for learning. Also, the display of the risk data for evaluation of risk is also important. For example we can predict risk for a full DVH and toxicity as a single number. But, it is also important to display the DVH and the colorized risk map that we have to assist the reviewer of plan quality assessment of what aspects of the DVH are influencing the toxicity risk. Furthermore a similar display can be used that incorporates the subregion analysis as well. We also use a full automated planning component that is different from biological IMRT optimization.

Without limiting the invention, the following disclosure of "Creating a Data Science Platform for Developing Complication Risk Models for Personalized Treatment Planning in Radiation Oncology" illustrates various embodiments of the broad inventive principles disclosed herein.

Data Science Examples

Creating a Data Science Platform for Developing Complication Risk Models for Personalized Treatment Planning in Radiation Oncology Abstract The common approach to assessing risk in radiation oncology treatment uses Lyman-Kutcher-Burman (LKB) derived models to calculate normal tissue complication probability (NTCP). LKB is not sufficiently robust to capture the modern clinical reality of three-dimensional intensity modulated radiation therapy (IMRT) treatments; the approach accounts for only two factors—$D_{max}$ and $V_{eff}$.

We present a data science platform designed to facilitate the rapid creation of data-derived NTCP models. The platform supports the use of native Philips Pinnacle data such as dose grids and contoured regions. Further, outcome data is encoded using Common Terminology Criteria for Adverse Events 4.0. Thus, the platform exploits the normal clinical workflow and information encoded with a standard ontology.

We used a platform to create NTCP models for two complications (xerostomia and voice dysfunction due to parotid and larynx irradiation, respectively) in less than three weeks.

We assess the resulting platform with a focus on its context within a Learning Health System (LHS). The system reported can serve as a guide to the development of radiation oncology data science platforms in particular and local-level LHS components in general.

1. Introduction 1.1 Motivation and Goal

In radiation oncology, two competing factors can be considered when generating treatment plans. Sufficient dose can be delivered to cancerous tissue to eradicate the tumor. However, the dose to surrounding healthy tissues can be kept reasonably low to limit complications that may arise during treatment.

Figure 16:
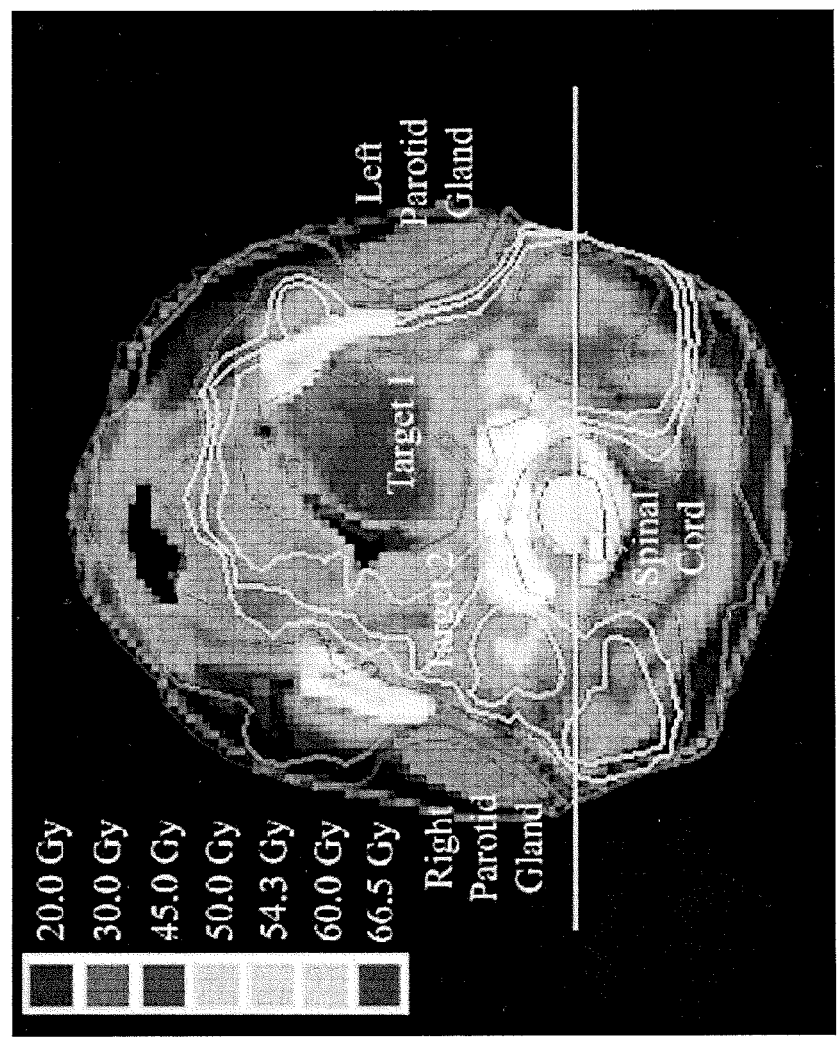
FIG. 16 shows specialized treatment planning systems and CT scans are used to create a complex, three-dimensional dose distribution, according to an embodiment of the invention.
Figure 17:
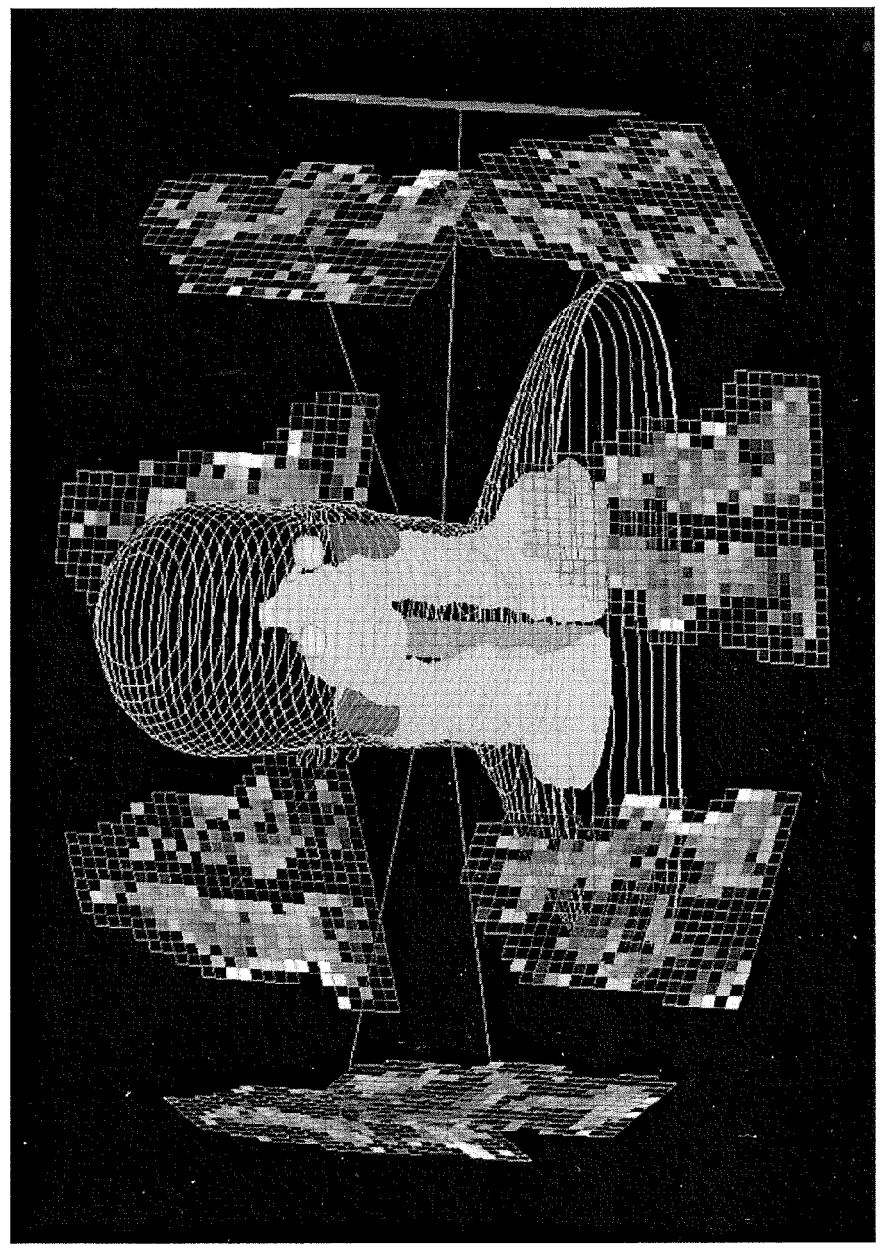
FIG. 17 shows automated systems execute the plan by directing multiple intensity modulated radiation beams to the target volume, according to an embodiment of the invention.
Figure 18:
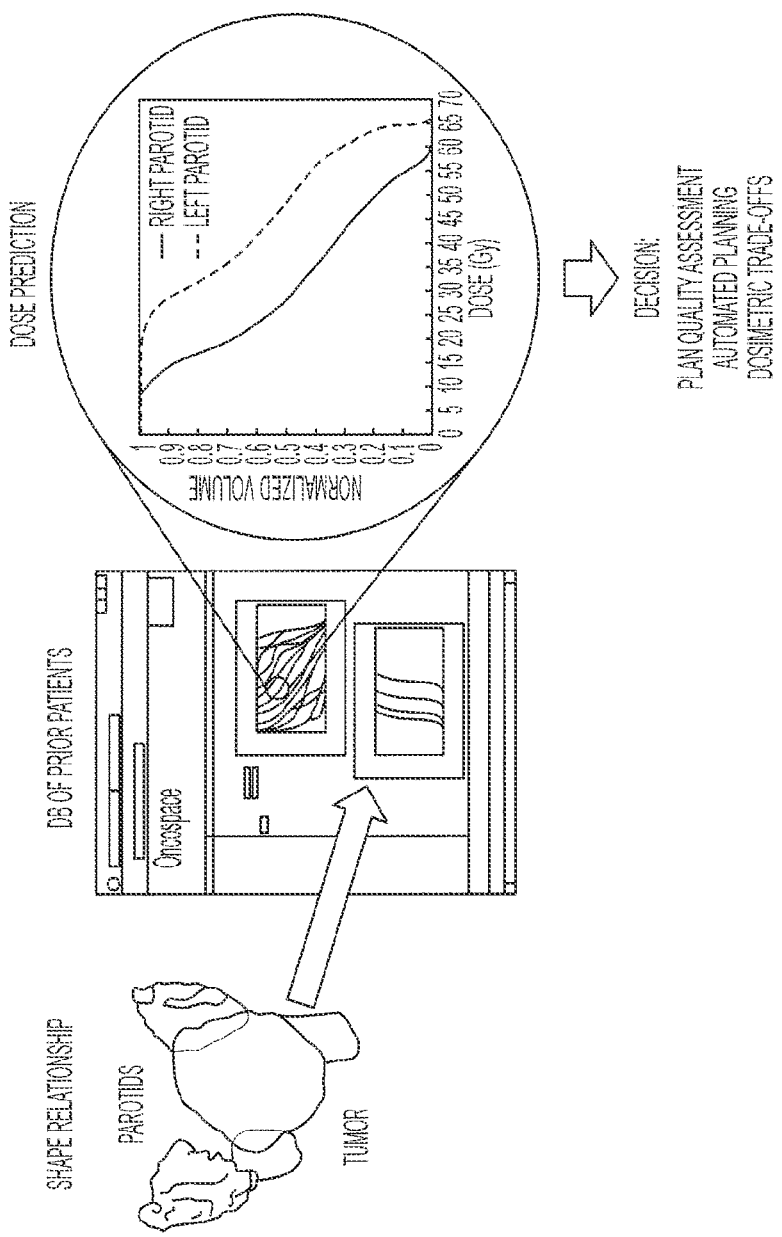
FIG. 18 shows clinical outcomes from previous patients are used to drive safer personalized planning with robust risk assessment, according to an embodiment of the invention.

To address this challenge, clinicians have highly sophisticated planning tools at their disposal. The typical workflow entails using dedicated software to create three dimensional treatment plans that are overlaid onto computed tomography (CT) images (FIG. 16). FIG. 16 shows that treatment planning software can be overlaid on a patient radiograph. Automated equipment executes the plan by delivering multiple intensity modulated beams [1] to the target volume while exposing surrounding tissue to lower, more diffuse energy levels (FIG. 18).

Despite highly advanced planning and delivery systems, the efficacy of a treatment plan depends strongly on current knowledge of normal tissue dose tolerances. Normal tissue complication probability (NTCP) models provide population-based estimates on dose limits to healthy tissues, but these models are known to have limitations. For example, these models generally ignore the complex, three-dimensional nature of radiation dose distributions, instead relying on simplified data reduction techniques. Patient medical history, lifestyle and chemotherapy regimen are also typically ignored. By improving the quality of NTCP models, it is likely that the quality of treatment plans may also be improved.

The Johns Hopkins University Department of Radiation Oncology has established an informatics platform known as "Oncospace" that may facilitate advanced NTCP modeling. Through routine, prospective acquisition of patient demographics, medical histories, treatment planning information, and outcomes (e.g., complications), there is sufficient data to support a variety of new modeling efforts.

Data science is the process of knowledge discovery from data [2]. The process requires rapid exploratory development of multiple analytical models [3]. The purpose of this work is to create an analytic pipeline that can transform the data in Oncospace into a format suitable for creating multiple ad hoc NTCP prediction models. This includes the incorporation of spatial dose information and patient-specific factors to improve upon existing models. By creating a data science platform for robust, data-driven NTCP models, it may be possible to create safer, personalized treatment plans based on the experience gained from treating prior patients (FIG. 18).

The Department has previously used this data to create shape descriptors to predict the nature of treatment plans [4].

This project seeks to incorporate many factors, including spatial data, in NTCP calculation.

1.2 Paper Overview

The Background section 2 presents the foundations, limitations and recent directions of NTCP modelling, as well as the process of healthcare data science (i.e. knowledge discovery in data).

The Methodology Section 3 and Results Section 4 describes our approach to domain specific challenges in the knowledge discovery process and our resulting system.

Section 5 Discussion and Other Embodiments reviews our work with a particular goal of placing the effort in the context of a Learning Health System.

2. Background

2.1 the Problem Domain, Complication Risk

Tolerance dose (TD) was the standard risk assessment measure in radiotherapy before medical imaging led to widespread adoption of spatial dose planning. For example, $TD_{50}$ values represented radiation levels that, when delivered uniformly to an organ's entire volume, resulted in a 50% risk of a given toxicity [5].

NTCP models are often derivatives of the widely used Lyman-Kutcher-Burman (LKB) framework. A series of papers develop the LKB model by adapting the tolerance dose to NTCP calculation for non-uniform irradiation over a portion of an organ. First, LKB assumes that there is a power relationship between a uniform dose across an entire organ (the tolerance dose assumption) and a larger uniform dose over a part of an organ [6]. The relationship is captured by two additional parameters, m and n—representing NTCP dose sensitivity and the dose-volume tradeoff rate, respectively.

Figure 19:
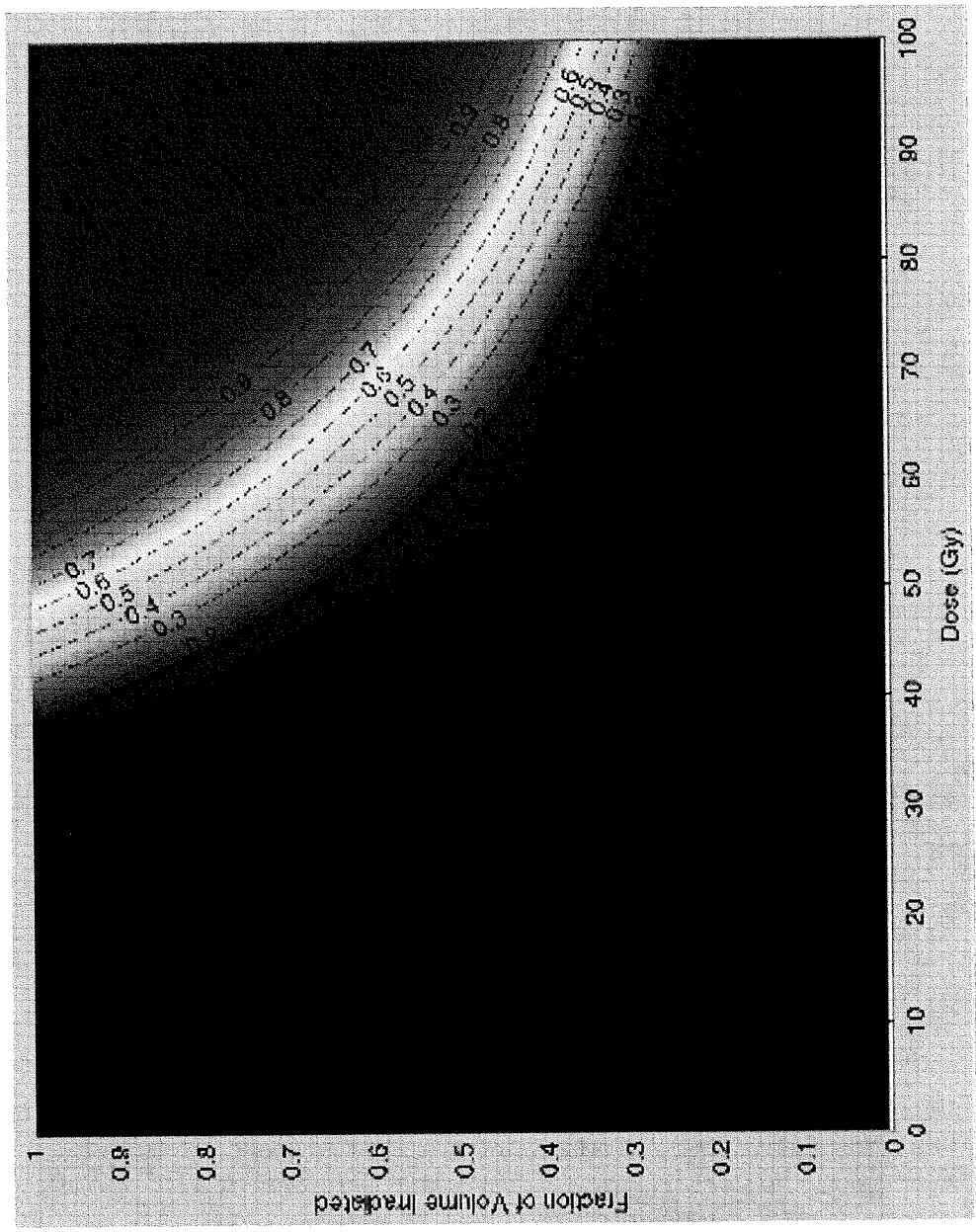
FIG. 19 shows NTCP contour map with isocurves representing LKB Dose-Volume tradeoff for xerostomia due to parotid irradiation (n=0.70, m=0.18, and $TD_{50}$=46 Gy), according to an embodiment of the invention.

FIG. 19 depicts the NTCP contours for dose/volume. The 0.5 isocurve intersects the y=1.0 line at x=$TD_{50}$ value (46 Gy in this case). High values form translates into the onset of risk beginning at small doses; the risk increases gradually. With low m values NTCP values are near zero until the dose approaches $TD_{50}$ then risk increases sharply. That is a low m value leads to a narrow band for the isocurves surrounding the 0.5 curve and the colors quickly move from blue to red; conversely, high m values leads to a wide band of isocurves and the colors gradually progressing from blue to red. Isocurves are vertical lines at n=0; the isocurves gain curvature as n increases. Thus, FIG. 19 shows a contour map with isocurves of constant LKB NTCP values using parameters for xerostomia due to parotid irradiation (n=0.70, m=0.18, and $TD_{50}$=46Gy(5, 6)).

Different complications have different LKB parameter values [7, 8]. FIG. 19 depicts the LKB dose-volume relationship for xerostomia (dry mouth) due to parotid irradiation.

With given $TD_{50}$, m, and n values, LKB provides a function for calculating NTCP for using dose and volume. However, treatment dose levels are not uniform. Dose volume histograms (DVH) are used to reduce the varying doses to two scalar values: maximum dose ($D_{max}$), and effective volume ($V_{eff}$) [9, 10].

Figure 20:
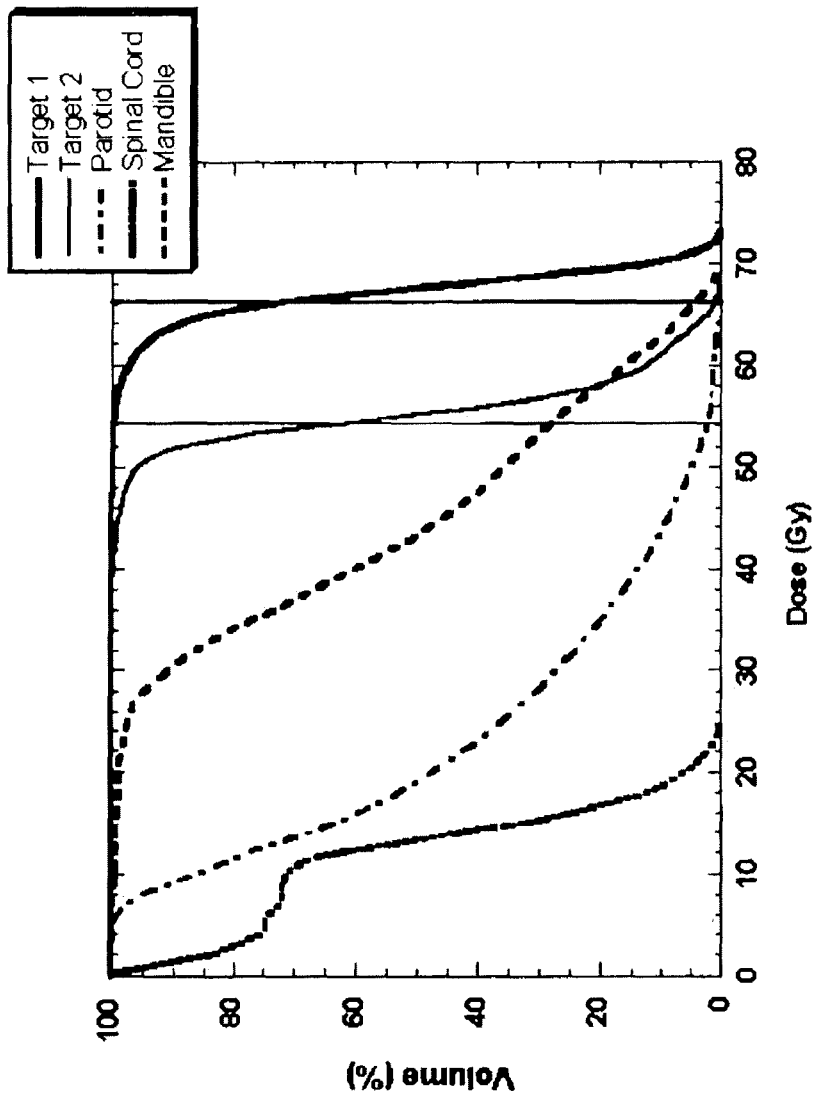
FIG. 20 shows DVHs generated during treatment planning, according to an embodiment of the invention.

In FIG. 20, each curve represents dosage delivery to a target region or included organ. The DVH can be read as "y % of the volume received at least x Gy of radiation." To calculate NTCP from a DVH, $D_{max}$=the maximum dose delivered and $V_{eff}$=the hypothetical percentage of the total volume irradiated if the entire volume were irradiated at $D_{max}$. $V_{eff}$ is calculated using the tradeoff parameter n.

In summary, the LKB model calculates NTCP by: accounting for partial volume irradiation by assuming an equivalence relationship between dose and volume represented by the parameter n; accounting for dose variation by using the DVH to reduce a treatment plan to $D_{max}$, and $V_{eff}$ scalar values; and fitting the result to a normal probability distribution with a volume-adjusted tolerance dose ($TD_{50}$) as the mean and a standard deviation scaled using the m parameter.

2.2 New Directions in NTCP Modeling

A number of limitations in the LKB model restrict its direct clinical applicability. The model's two DVH-derived inputs and three parameters are the sole NTCP determinants. LKB does not include relevant factors specific to the patient, such as, dose placement, chemotherapy regimen, medical history, etc. [11].

Bentzen et al. surveys the lessons learned since the introduction of LKB more than two decades prior and presents future directions for NTCP research. Trends include: addressing the more diverse spectrum of treatments modern oncology patients receive; creating personalized risk-benefit assessments; and focusing the developing methods based on "more data" as opposed to creating "more [analytical] models."

The survey provides a four level taxonomy of validity: (1) face validity—clear and obvious inconsistencies between the model and known facts are not present; (2) internal validity—the model's predictions are consistent with the data provided; (3) external validity—the model is resistant to over-fitting and maintains predictive performance against other external datasets, ideally from a separate institution; and (4) clinical utility—applying the model results in clear benefits to patient care.

Our current platform addresses face and internal validity. We hope to extend the platform to allow for external validation when other institutions contribute to Oncospace.

2.3 Knowledge Discovery in Healthcare

Clinical patient data is collected in the course of treatment and stored in health information systems. The data, therefore, are not in a format that is immediately conducive to analysis.

Fayyad, et al. introduced what is generally considered the fundamentals of the process for knowledge discovery in databases (KDD). Typically the vast majority of data analyzed was not collected for that purpose, but rather in the course of an institution conducting its general activities. In the case of health-care, data is generally from electronic health records (EHR), or other components within hospital information system.

Fayyad, et al. divides KDD into nine steps: (1) understanding the problem domain and the previous work in the area; (2) selecting a target dataset; (3) data cleaning and preprocessing; (4) data reduction and projection; (5) matching the knowledge discovery goals with a data mining approach; (6) exploratory analysis with hypothesis and model testing; (7) data mining; (8) interpreting results; and (9) acting on discovered knowledge.

Figure 21:
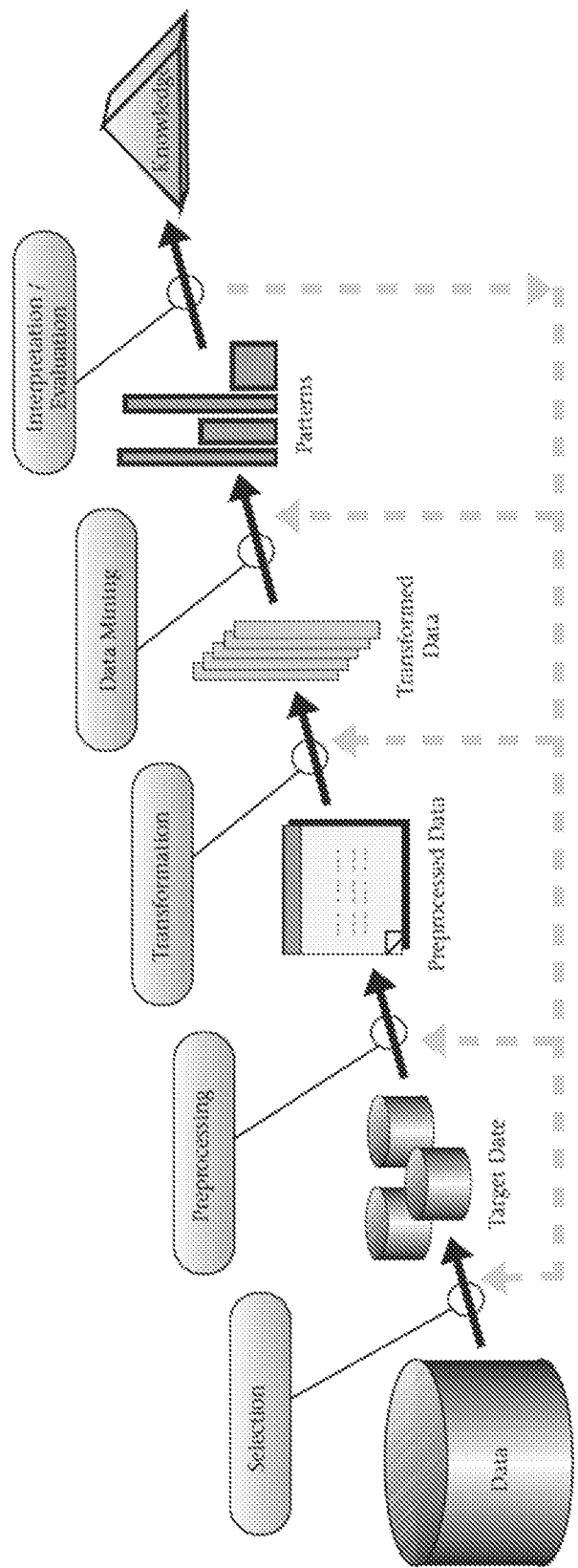
FIG. 21 shows stages in the knowledge discovery process, according to an embodiment of the invention.

This paper presents our work on the prerequisite steps prior to data mining, i.e., steps 1-5 (see FIG. 21).

KDD primarily addresses situations where the original data is highly structured and stored in relational database systems. Medical data in general, and radiation oncology data in particular is largely unstructured, consisting of images, free-text, custom software format, etc. The Oncospace project has focused on integrating structured data collection into the clinical environment and has utilized the Common Terminology Criteria for Adverse Events 4.0 data standard for capturing treatment related toxicities which greatly simplifies the data cleansing.

The emerging area of data science addresses the requirements unstructured data imposes. A key requirement for a data science platform is an analytic sandbox that is separate for the organizational data repository. Data science modeling involves "failing enough," that is experimenting with enough models to feel confident that the superior models that emerge have true predictive advantages. The analytic sandbox allows for conducting research without risking the original data stores [3].

Figure 22:
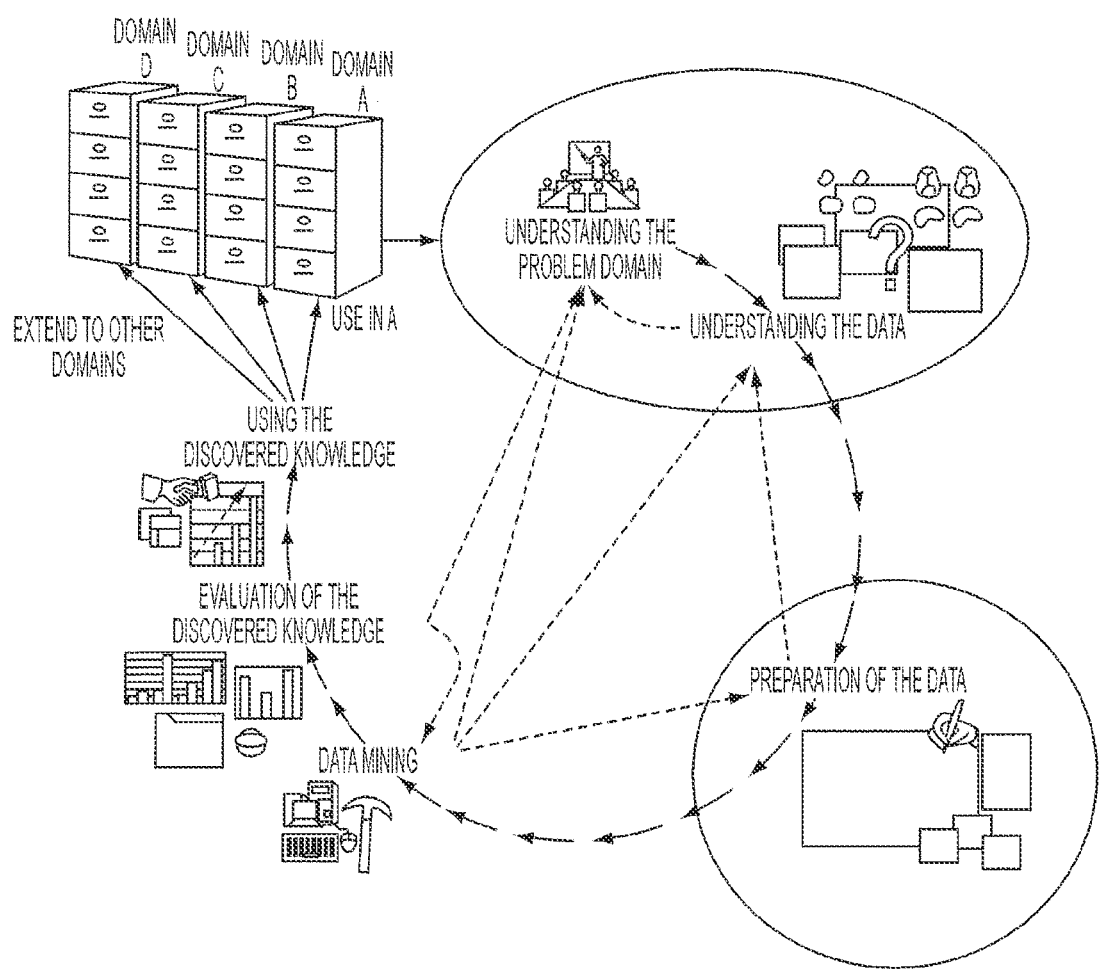
FIG. 22 shows a knowledge discovery process, according to an embodiment of the invention.

In addition unstructured data, the nature of healthcare raises further issues, such as: the heterogeneity of medical data; the multidisciplinary nature of the process due to the need for highly-trained clinical experts; ethical issues arising from the nature of the problem; etc. These issues create a process that is more iterative in nature. As is depicted in FIG. 22, the medical domain's inherent complexity requires data science analysts to frequently refine their understanding of the problem domain and data; there must also be constant revisiting of the data preparation stage to insure that the format is appropriate for creating clinically relevant models [13]. Circles can represent the process of creating the platform for data-mining.

3. Methodology

3.1 Overview

This section describes our implementation of KDD steps 2-4; these step are the perquisites of the data mining tasks (see Section 2.3). Step 1, understanding the problem domain is addressed by our background of NTCP in Sections 2.1 and 2.2.

3.2 Oncospace Data Selection

Figure 23:
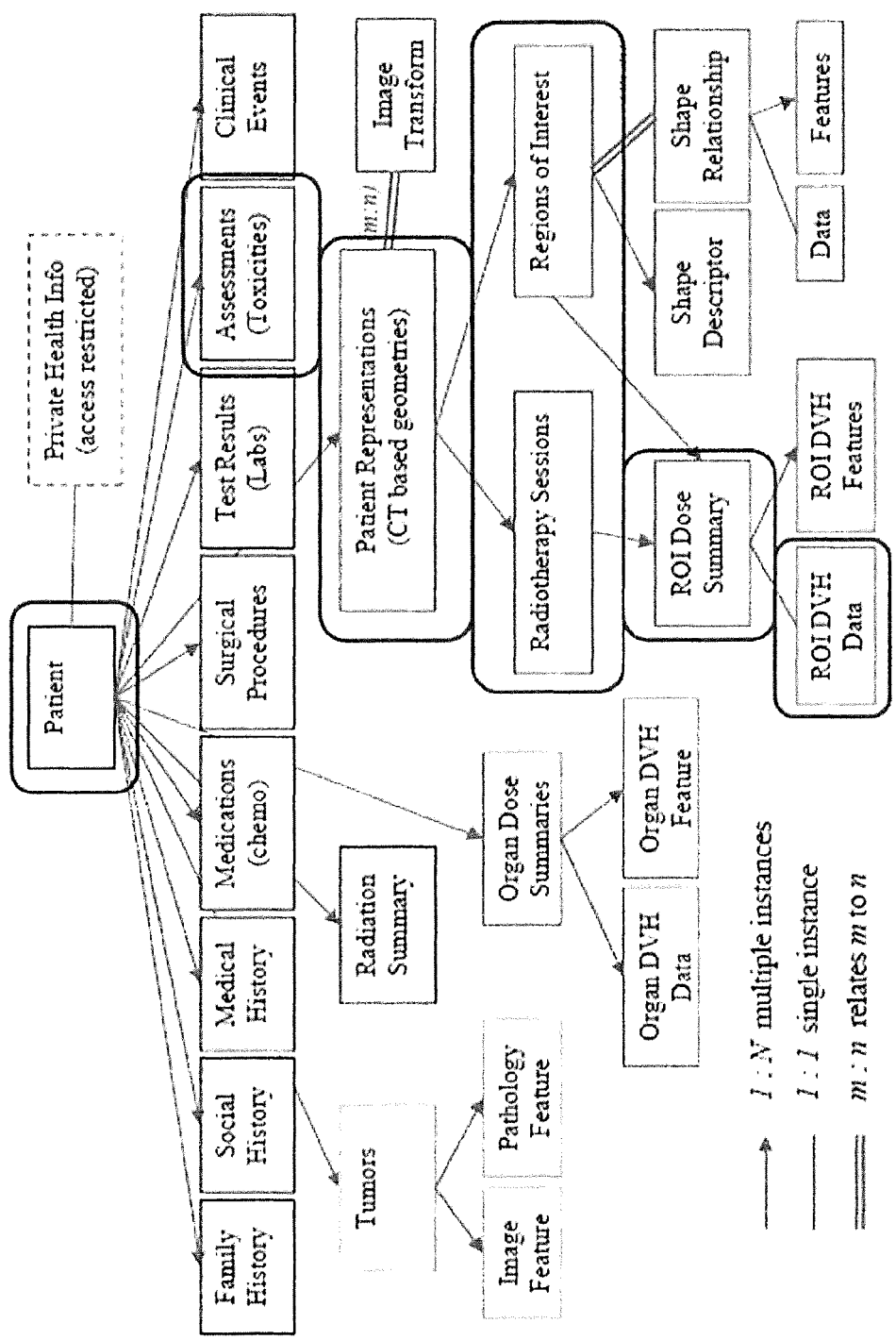
FIG. 23 shows a database structure, according to an embodiment of the invention.

Oncospace data selected for the pipeline is circled in red on FIG. 23. The dose grids, regions of interest, and DVHs are taken directly from the Pinnacle treatment planning system. Patient outcomes/toxicities (assessments) are scored at each patient visit in structured form. Red circles can highlight data selected for the platform.

3.3 Cleaning and Preprocessing Native Pinnacle Data

Figure 24:
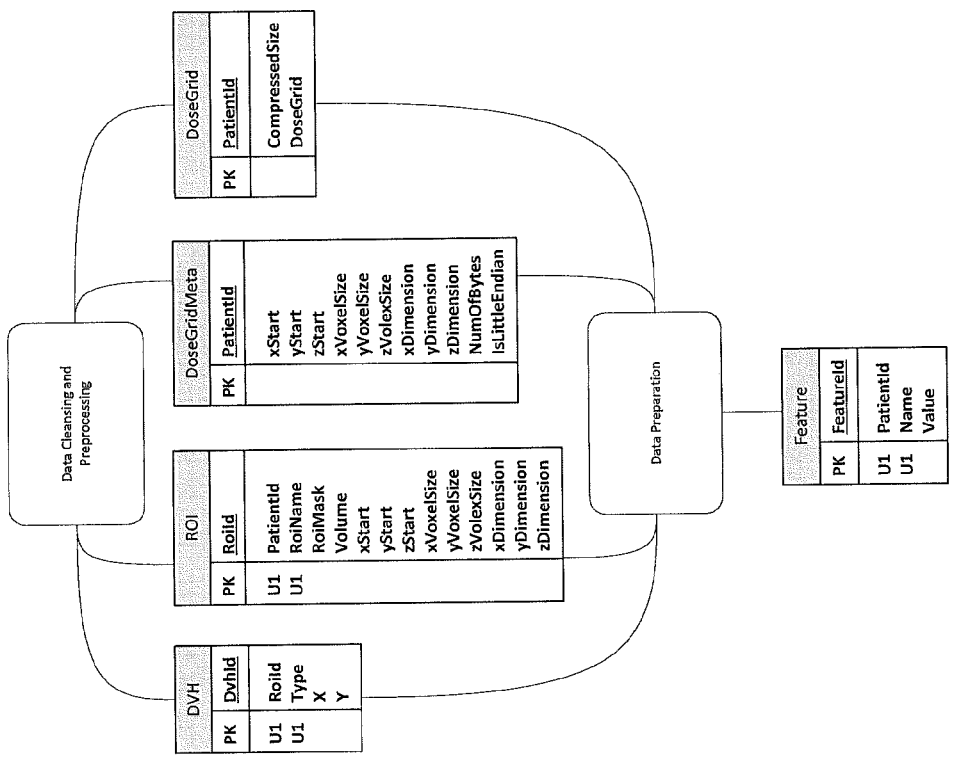
FIG. 24 shows the loading and processing of data within the analytic sandbox tables, according to an embodiment of the invention.

A Pinnacle dose grid is an array of xxyxz 32-bit floating-point values—one dose value for each voxel. The DoseGrid table within the analytic sandbox (see FIG. 24) stores the cleaned and preprocessed Oncospace grid data.

In the treatment planning setting, the average size of dose grids (3.22 MB) is not a matter of concern. The platform must process over 300 patients however. This scale imposes a requirement of transferring 1.09 GB via the network. To address this issue we store dose grids in the analytic sandbox using gzip compression.

A second issue encountered occurs due to the Hospital's migration from Solaris. Oncospace contained data in both endian formats. Detecting the problem in a dose grid is straight-forward; the grid will contain values that are grossly out of range (including NaN values).

Oncospace supports a one-to-many relationship between patient and treatment plans. For data analysis, all relationships should be one-to-one to allow for the creation of a single feature vector for each case.

Typically, Head and Neck patients receive a single treatment. We excluded the single patient with multiple treatments from the analytic sandbox. Therefore the sandbox relationships are joined by the anonymous patient id.

3.4 Transforming 3D Data

The Radiation Oncology Medical Physics positioning protocols uses a single continuous real number workspace spatial coordinate system as a reference frame for assuring consistency between planning and treatment. The dose grids and CT (ROI) frames are independent of each other, with different voxel sizes. Oncospace provides workspace starting location, voxel size and voxel dimensions for both frames.

We use three separate software classes to provide a straight-forward interface for obtaining three dimensional dose values within: a DoseGrid, a ROI, and a ROIDoses.

Given a point in the workspace, DoseGrid uses a k-d tree to return a dose value based on the nearest dose grid voxel center. ROI provides an iterator of CT voxel center points within a contoured region. ROIDoses provides an iterator of workspace ROI voxel center points, in the workspace reference coordinates with corresponding dose values.

3.5 Visualization of the 3D Treatment Planning Data

Figure 25:
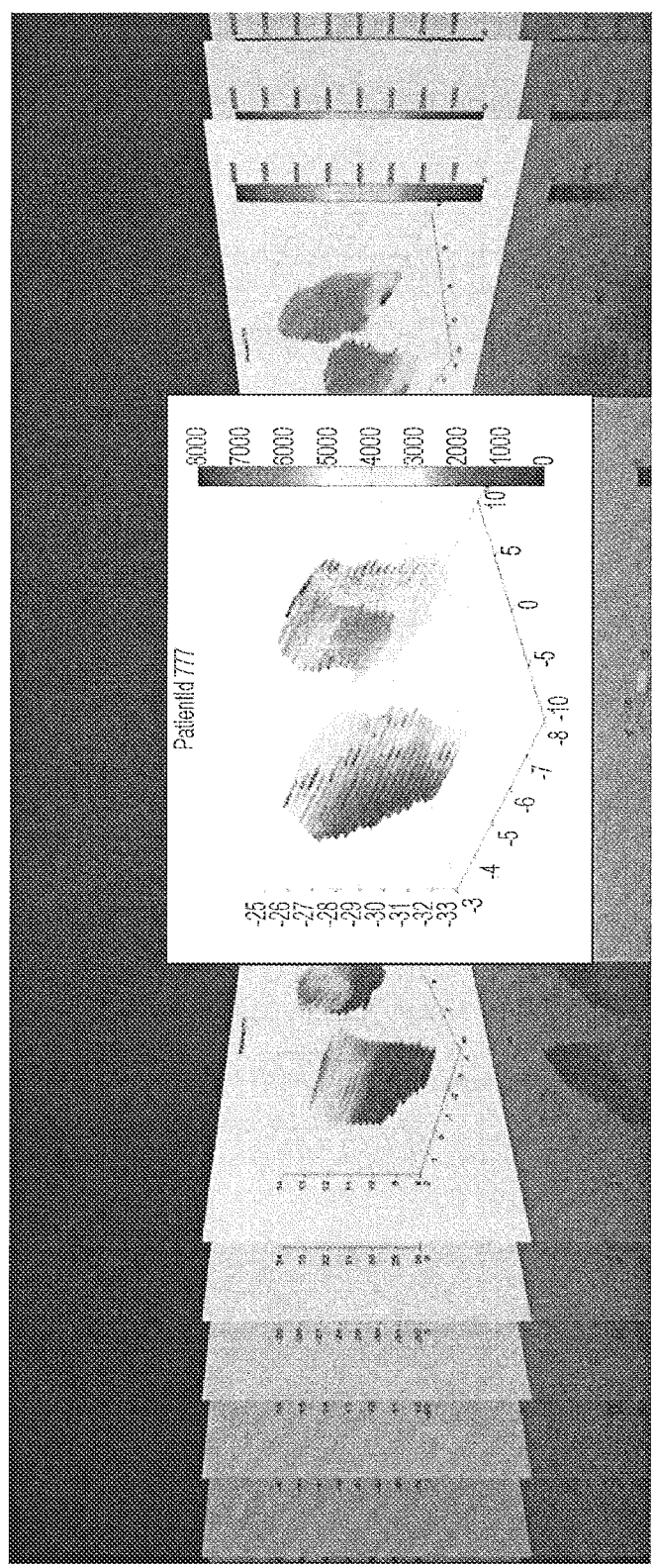
FIG. 25 shows 3D visualizations of Oncospace parotid treatment plans, according to an embodiment of the invention.

Using ROIDoses we can create three-dimensional treatment delivery visualizations (see FIG. 25). A difficulty inherent in medical data is variation due to lack on canonical representations [13]. The manual contouring of our organ regions can lead to significant variation. By providing an overview of the dataset, the visualizations were beneficial in designing informative histogram based features that were sufficiently general to manage the high levels of non-clinically relevant deviations in the underlying data.

3.6 Storing Features in a Format Suitable for Data Mining

Calculating NTCP is well suited to a trained classification data mining approach. These algorithms typically require a tabular training set for parameterization. Each row is a patient, and each column is either a numeric or categorical value. After training calibration, the models will provide a likelihood score for new patients.

The data preparation step (see FIG. 24) calculates per patient summarization feature values. An example of a feature is the LKB NTCP value for voice change based on the treatment plan's larynx DVH.

The Feature table contains unique records of a patient id and feature name, with a corresponding value. SQL Server provides a PIVOT operator that transposes individual field names into column headers.

The combination of the Feature table and PIVOT operator permits rapid, ad hoc creation of tabular data sets. There is no need to change the analytic sandbox's schema during experimentation.

4. Results

4.1 Platform

Figure 26A:
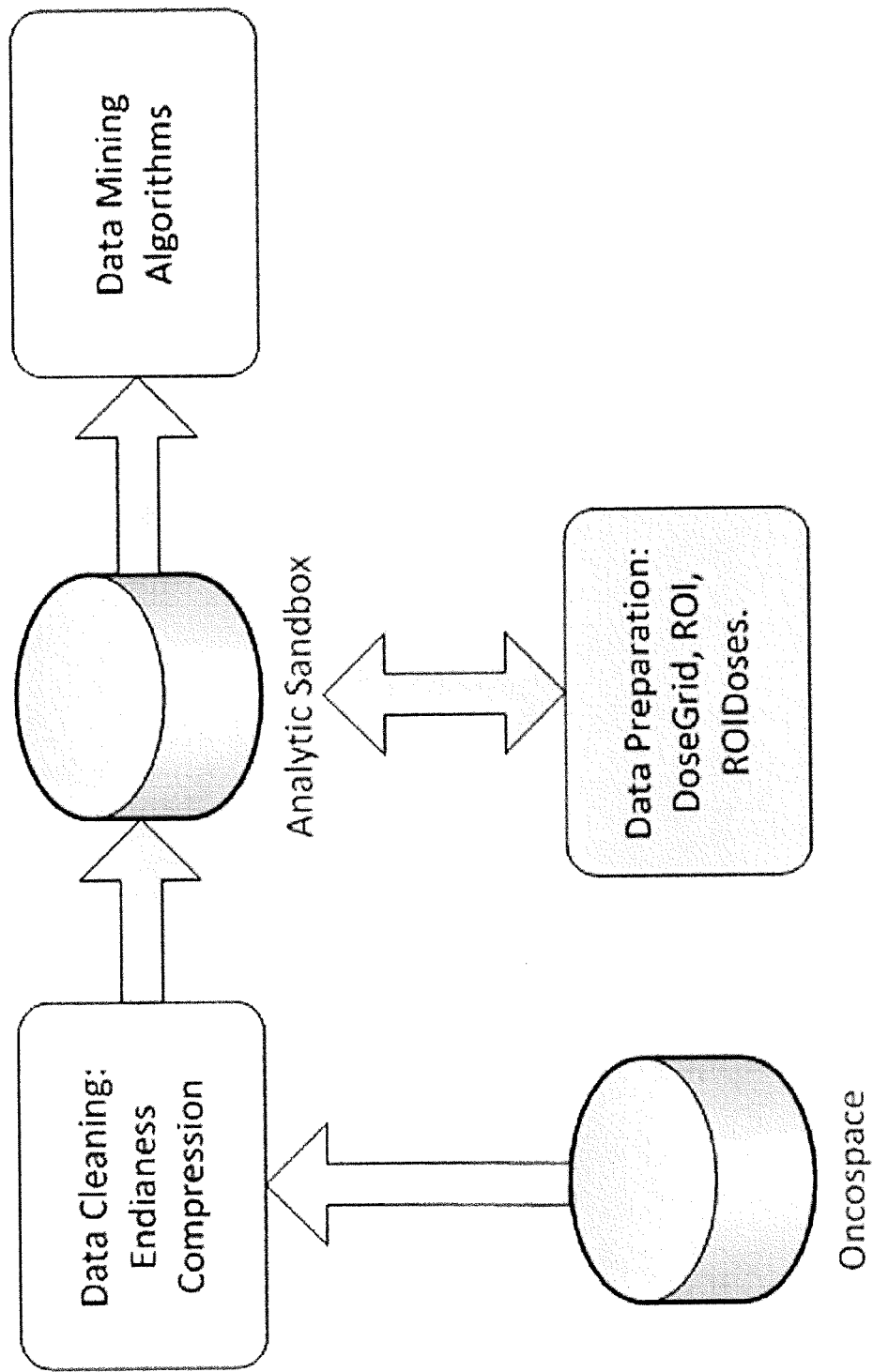
FIG. 26A shows a high-level view of the resulting platform, according to an embodiment of the invention.

FIG. 26A displays the resulting analytic pipeline. Data mining algorithms read from the analytic sandbox exclusively. Exploratory analysis is therefore separated from the general use repository.

4.2 The Analytic Sandbox

A key benefit of the analytic sandbox is the decoupling of KDD operation from the underlying data source. The decoupling permitted not only the prototyping of different data models for analysis, but also the safe modification of data storage. As noted in Section 3.3, the data for dose grids in the sandbox is stored in a gzip format. The resulting 73.8% compression rate reduced the average dose grid storage size from 3.22 MB per patient to 864.37 KB and the total storage from 1.09 GB to 292.91 MB.

4.3 the Size Reduction is Particularly Important in KDD where it May be Necessary to Transmit, the Entire Dataset Over Network Connections. Experiences with the Platform We initially used the platform to explore NTCP models for xerostomia due to parotid gland irradiation. To verify the platform's general utility, we created models for voice dysfunction due to larynx irradiation. The model development time was particularly low. We constructed initial models for both toxicities within three weeks of completing the framework.

We are in the process of verifying, interpreting and refining our models (step 8 in KDD). On a preliminary basis, models in both cases appear to improve upon the LKB approach.

5. Discussion and Other Embodiments

5.1 the Platform's Strengths, Weaknesses, and Observations

The platform is capable of exploiting data drawn directly from the Philips Pinnacle treatment planning system. Dose grids, patient DVHs, and contoured regions derive directly from the clinical workflow. The platform also benefits from experts reviewing the patient record and identifying outcomes using a standardized terminology.

As we note in Section 4.3, we were able to use the platform to rapidly develop NTCP models for two separate complications.

The main drawback we have observed is the need for more patient cases. In the parotid analysis, we had 364 cases in total, 275 of which had Grade 2 or higher xerostomia; in the larynx analysis, we had 99 cases, 8 of which had Grade 2 or higher voice dysfunction.

Using techniques such as leave-one-out validation we were able to develop meaningful results. However, manifold-based model trainings implicitly separate patients into subgroups and perform analysis over the individual subgroups. Insufficient training cases within subgroups constrain the predictive performance of this class of models.

5.2 Other Embodiments

The platform can address the first five steps in KDD. The work can serve as a foundation for analyzing data within Oncospace. We can create NTCP models for additional complication.

The platform can address the first five steps in KDD. The work can serve as a foundation for analyzing data within Oncospace. We can create NTCP models for additional complication.

Beyond NTCP modelling, patient similarity models may also be developed. Physicians can use the models to assess the "expected course" of treatment complications based on previous patients.

In another embodiment, data from external institutions can be included. This data would also be integrated into the platform. Not only does data from other institutions address the need for more cases presented in Section 5.1, but also presents the opportunity to assess the external validity of models (see Section 2.2).

5.3 The Learning Health System

In keeping with this minitrack's goal and the HICSS 47 Distinguished Lecture's theme, we assess this project in the context of a Learning Health System (LHS) [14]. Our platform's goal matches LHS' raison d'etre. We wish to use technology to rapidly learn from EHR data and adapt our new knowledge to the clinic.

A LHS possesses a fractal nature; a system has self-repeating patterns at different levels of scale. The platform's use of data in the native format of clinical systems such as Pinnacle, and patient records reviewed by experts using a canonical terminology is a pattern we expect to be replicated at multiple LHS levels.

From a computing perspective we expect patterns implemented within this platform reproduced using Big Data technologies at higher levels in a fractal LHS. A number of "NoSQL" systems [15] are available for storing large-scale versions of the analytic sandbox. MapReduce [16] is an approach that is easily applicable to the processing required for data cleansing and preparation. These technologies are built for scale; they serve as the backbone infrastructure of the major Internet companies.

6. Conclusion

We have presented a platform for rapidly creating data-driven NTCP models. The system draws data directly from Phillips Pinnacle treatment planning software. We use outcome data encoded in a standardized terminology.

The resulting platform supported the rapid creation of initial NTCP models for two complications.

Within the context of a Learning Health System the platform: demonstrates a local system for discovering knowledge from data generated in the course of the normal clinical workflow; and exhibits the fractal nature of a LHS where local design patterns can be replicated at higher level using Big Data scaling technologies.

In addition, further implementations using the broad inventive principles described herein are contemplated.

Machine Learning Based Risk Modeling of Voice Dysfunction and Xerostomia Using Spatial Dose Distribution in Intensity-Modulated Radiation Therapy

I. Abstract

Objective Modern oncology using intensity-modulated radiation therapy (IMRT) can permit three-dimensional treatment planning. However, contemporary methods for assessing normal tissue complication probability (NTCP) are typically Lyman-Kutcher-Burman (LKB) derivatives. LKB does not account for dose placement. We seek to use machine learning to incorporate three-dimensional planned dosages into complication risk modeling.

Materials and methods Prospective patient data from the Oncospace project (voice dysfunction: n=99, $n_+$=8, $n_-$=91; xerostomia: n=364, $n_+$=275, $n_-$=89) can be used to train linear regression (LR), random forest (RF), and naïve Bayes (NB) models for voice dysfunction and xerostomia (dry mouth) due to irradiation of the larynx and parotid glands, respectively. Bagged LR (BLR) and NB (BNB) models can also assessed. Features can be selected using information gain; and models can be evaluated using the receiver operating characteristic area under the curve (AUC).

Results Of the five features selected for voice dysfunction, four were spatially specific. The baseline LKB AUC was 0.596. Model AUCs were: BNB 0.915, BLR 0.905, NB 0.900, LR 0.896, RF 0.724. For xerostomia due to parotid gland irradiation, the most significant feature was LKB-based NTCP. The baseline LKB AUC was 0.700. Model AUCs were: BNB 0.743, BLR 0.737, NB 0.734, LR 0.731, and RF 0.674.

Discussion The strong outperformance of the spatial models to LKB for voice dysfunction supports a relationship between the complication and dose placement. LR's failure to outperform other high bias models for both complications supports the possibility of higher predictive performance with additional cases.

Conclusion We have presented machine learning NTCP models for two toxicities in radiation oncology. In both cases, we demonstrated an improved performance over LKB.

II. Objective

An objective of our work can be to use a machine learning approach to develop normal tissue complication probability (NTCP) models that incorporate spatial dose distribution.

III. Background and Significance

Intensity-modulated radiotherapy (IMRT) employs sophisticated computerized systems to deliver complex three-dimension treatment plans. The IMRT workflow entails a medical physicist developing a personalized treatment plan using specialized software that overlays the dose distribution onto a patient's radiograph (see FIG. 16). An automated system then executes the plan by generating multiple intensity-modulated radiation beams from separate origins focusing on the target region(s). IMRT's advantage is the ability to deliver a high dose to diseased tissue while providing a tailored diffusion pattern to the normal surrounding tissue [17].

While IMRT gives practitioners the ability to provide tailored treatment, there is a lack of guidance as to the impact of spatial dose distribution on complication risk. The absence of quantified methods for spatial risk assessment also impairs the development of automated tools within treatment planning software. This work presents a machine learning approach to calculating NTCP that incorporates spatial dose distribution.

A. Oncospace

The Oncospace informatics project of Johns Hopkins University's Department of Radiation Oncology provides both the patient data and the model building data science platform for this work. Oncospace's goal is the prospective collection of patient demographics, medical histories, treatment plans, and outcomes. The database currently contains approximately 600 patients with full three-dimensional treatment planning data extracted from Phillips Pinnacle Radiology System using the cross-vendor DICOM RT standard. Outcome data is encoded using Common Terminology Criteria for Adverse Events 4.0.

Oncospace also provided a data science platform to facilitate machine learning modeling of the data collected [18]. The data for this work consists of Oncospace's dose grids for the manually segmented parotid glands and larynx, the treatment plan DVHs (see the Lyman-Kutcher-Burman Section), and patient outcomes for xerostomia (dry mouth) and voice dysfunction due to irradiation of the parotid glands and larynx, respectively.

B. NTCP Modeling

1. Lyman-Kutcher-Burman

Contemporary NTCP models are generally based on the Lyman-Kutcher-Burman (LKB) approach. LKB an extension of the tolerance dose (TD) approach developed early in radiation oncology.

Prior to modern three-dimensional medical imaging, radiotherapy was restricted to uniformly irradiating an entire region containing both disease and normal tissue. Risk assessment entailed using a value that specified a dose level that yielded a specified probability for a given complication. For example, $TD_{50}$ is the dose level that leads to a 50% complication risk [19].

As medical imaging and radiology technology advanced, the need to model both partial volume and non-uniform intensity irradiation became clear. LKB extended the TD approach to address these requirements.

Lyman [20] addresses partial volume by assuming a power relationship between the TD for a uniform dose across an entire organ volume and the TD for a uniform dose over a partial volume. That is:

$$TD(V) = \frac{TD(1)}{V^n}$$

Lyman then derives NTCP using a normal Gaussian distribution:

$$NTCP(V) = \Phi(t) = \frac{1}{\sqrt{2\pi}} \int_{-\infty}^{t} e^{\frac{-t}{2}} dx$$

$$t = \frac{D - TD_{50}(V)}{\sigma(V)}, \text{ where } \sigma(V) = mTD_{50}(V)$$

That is, the Lyman partial volume NTCP results from a normal distribution with a mean of the volume adjusted $TD_{50}$ and a standard deviation proportional to the volume adjusted $TD_{50}$. Ermani, et al. [21], Burman, et al. [22] provide widely cited values for the parameters, m, n, and $TD_{50}$.

Kutcher and Burman [23] relates dose variation to Lyman's partial volume using a concept of effective volume:

$$\Delta V_{\text{eff}} = \Delta V_i \left(\frac{D_i}{D}\right)^{\frac{1}{n}}$$

In practice, $D=D_{max}$, the maximum dose the patient receives and $D_i$ corresponds to doses assigned to bins in to a histogram, and $\Delta V_i$ is the proportion of the volume that receives the dose level. We can therefore calculate:

$$V_{\mathit{eff}} = \sum_i \Delta V_i \left(\frac{D_i}{D}\right)^{\frac{1}{n}}$$

The $V_{\mathit{eff}}$, can serve as an input to the Lyman NTCP formula. Therefore, once m, n, and $TD_{50}$ parameters are provided, a dose volume histogram (DVH) fully determines the LKB NTCP. FIG. 19 visualizes the LKB NTCP dose-volume relationship for xerostomia due to parotid irradiation.

It is common in clinical practice to refer to an equivalent uniform dose (EUD). EUD is the dose where the NTCP isocurve intersects the V=1. EUD represents a dose for uniform full volume irradiation that is hypothetically equivalent to the proposed treatment plan [24]. Therefore, EUD links LKB to the earlier TD approach.

It is also common to represent DVHs as cumulative histograms. A point on the curve can be read as, "y proportion of the volume received at least x Gy of radiation" (see FIG. 20).

2. Beyond LKB

Three coarse biological assumptions underlie LKB: an organ's functionality is distributed uniformly over its volume—i.e. there are no specific regions within an organ that must be preserved to avoid complication risk; there is a smoothly defined equivalence between dose and volume—e.g. in FIG. 19's contour map, bathing the both parotid glands in a 46 cGy dose is equivalent to exposing approximately two-thirds of a single parotid to an intense 100 cGy dose; and the sole factors in NTCP are dose and volume.

It is well recognized LKB's assumption limits its robustness and applicability to the clinic [25]. Bentzen, et al. [26] surveys the recent state of NTCP modeling with a goal of setting future priorities for improvement in the field. Machine learning fits well with several identified trends, including: the need for spatial modeling due to the widespread use of IMRT; a shift to data-driven modeling; a growth in patient-level data analysis; and a lack of consistency in organ contouring (see Spatial Features section).

Research into the impact of dose placement on outcome includes: animal models(11-13); controlled clinical trials [27]; and further manual contouring or identification of regions of interest outside of the clinical workflow [28, 29]. These approaches are costly and labor intensive however.

Data driven approaches have generally focused on DVH related analysis, such as representing the curve using principal component analysis [30]. There has also been work on optimizing treatment plans based on the intersection of organs and the target regions using an "overlap volume histogram [31]." However, we believe that this is the first work to move beyond uniform dose and employ a full machine learning approach to spatial dose distribution. The spatial features presented are automatically generated without non-clinical manual contouring.

C. Applicable Machine Learning

We direct the reader to Domingos [32] for an excellent high-level outline of machine learning. We will present the topic in a clinical context and specific to NTCP modeling.

The first step in machine learning is to represent a patient as a set of features referred to as a feature vector. In this work's context, features are transformations of the raw DVH and spatial data. We will refer to a set of feature vectors (patients) as a dataset. Feature selection is a process of selecting the most informative features from an initial set of candidates.

A trainer algorithm uses a set of feature vectors (training data) to learn (or train) a model. From a workflow perspective, the trainer receives the vectors as input and outputs a model. Training data vectors will contain outcome as one of the features. In the case of NTCP modeling, the model the trainer learns will be a classifier. The classifier accepts new feature vectors, and outputs a prediction of the presence of the complication. The trainer algorithm and the set of models it can learn together form a machine learning technique or method.

1. Validation

Machine learning methods generally lack sufficient confidence proofs. Therefore, assessing models, like learning, is data driven. We use cross-validation for model assessment [33]. In 10-fold cross-validation, the training data is divided randomly into ten groups. Each group iteratively serves as the testing data while the models are learned using the remaining groups as a training data.

2. Bias Vs Variance

Selecting machine learning methods often entails a tradeoff between bias and variance. Bias can be viewed as the error due to the structure the model imposes on the data. The structure allows for training on small datasets, but the bias error is fixed.

Linear regression is a high bias model that may be trained using as few as two data points. While additional data may initially create a better fitting model, the model will still attempt to fit the data to a line. The linear structural assumption fixes a limit on predictive performance that additional data cannot address.

Variance represents a model's instability upon encountering feature vectors dissimilar to its training set. Therefore, variance error declines with new data. Variance is the price of flexibility (i.e. reduced bias). Approaches that reduce bias while limiting increases in variance, such as bagging (see below) often benefit model performance.

3. Naïve Bayes

The WEKA naïve Bayes (NB) implementation is restricted to nominal features; continuous numerical features are discretized and binned [34]. NB classifiers assume all input features are independent of each other. In case of binned features, this is clearly not true because the presence of a value in a given bin precludes its presence in others. Despite the invalidity of the independence assumption NB often perform remarkably well [35]. NB applies Bayes theorem:

$$P(X_i | A) = P(A | X_i) \frac{P(X_i)}{P(A)}$$

The independence assumption, and Bayes theorem permit us to calculate A's contribution to the likelihood of the feature vector's membership in $X_i$ using prior knowledge from the training data. Like linear regression, NB is a linear separator; therefore, it is considered a relatively high bias model.

4. Bagging

Bagging is a method of using a single dataset to generate multiple simulated datasets. We build the bagged dataset by randomly selecting a feature vector from the original dataset with replacement—that is, a feature vector can be selected multiple times. The new dataset can contain the same number of feature vectors as the original. Due to multiple selection, the expected percentage of the original feature vectors that are "outside the bag" of the new dataset is 36.8% ($e^{-1}$).

A trainer then learns separate models for each bagged sample. Using the models, we can build an ensemble classifier that uses the vote of its components. Bagging generally reduces bias while yielding a limited increase in variance [36].

5. Random Forest

Random forests are classifiers built of independently trained trees. Each is trained on a separate bagged dataset. During training, at each decision node, the features that are selected to create the split rule are a random subset of the features within the feature vector. The trees in RF perform classification based on diverse views of the training data. The resulting classifier returns the vote of the individual trees. RF offer provable converge with the growth of the number of trees [37]; and are often top performing classifiers.

IV. Materials and Methods

Oncospace provided patient prospective patient data as well as a platform for transforming the data into usable features [18]. Oncospace extracted dose grids and target regions from Phillips Pinnacle treatment planning system using the cross-vendor standard DICOM RT. Outcomes are encoded using the Common Terminology Criteria for Adverse Events 4.0; for both toxicities scores of two or greater indicate for the complication. Feature selection, model training, and AUC evaluation were performed using the WEKA software package [41].

Patient Positioning

A. Features

Data for the larynx and individual parotids glands used for feature creation included: region volume, DVHs, and three-dimensional dose grid treatment plan data. We used clinical experience to group dose levels into five bands (in cGy): 500-2499; 2500-3999; 4000-5499; 5500-6999; and ≥7000.

1. DVH Based Features

For each patient in the dataset the $V_{eff}$ and $D_{max}$ values were calculated for: the larynx; the individual parotid glands; and the combination organ of both parotid glands using volume weighting. LKB NTCP values for the xerostomia and voice dysfunction using the $V_{eff}$ and $D_{max}$ values for the larynx and the combined parotids, respectively. The LKB parameters for the calculations were: m=0.16, n=0.45, $TD_{50}$=4,630 for voice dysfunction(26); and m=0.18, n=0.70, $TD_{50}$=4,600 for xerostomia [21, 22].

For the parotid glands we also calculated the amount of each dose band received by each gland as a portion of the combined parotid volume. That is:

Let $V_L^D$=the volume of the left parotid receiving dosage within band D; and $V_L$ and $V_R$=the total volume of the left and right parotid glands, respectively. Then the features left parotid value is:

$$\frac{V_L^D}{V_L + V_R}$$

We refer to this feature as "gland dose exposure."

2. Spatial Features

Spatial features for modeling voice dysfunction are created from a single region—the larynx; spatial features for modeling xerostomia are created from the individual parotids. Organ regions are manually contoured in the course of the clinical workflow. Therefore, the actual shape and location of regions can vary substantially. The challenge is to create spatial features that are sufficiently specific as to be informative and still general enough to avoid capturing non-relevant variation.

We arrived upon an appropriate set of features by using spatial dose visualizations. Each region's spatial dimensions were divided into fifths using the maximum and minimum values for the dimension; this yielded 15 sub-regions per region. We then calculated the percentage of the total dose within the band delivered to each sub-region. We refer to these values as "dose grid distributions" for a band, on a region's $i^{th}$ dimension's $j^{th}$ bin. This process created 75 features per region.

3. Feature Selection

The calculations above yielded 79 candidate features for voice dysfunction (NTCP, $V_{eff}$, $D_{max}$, region volume, and 75 spatial features) and 165 candidate features for xerostomia (NTCP; left, right, and combined $V_{eff}$ and $D_{max}$; left and right region volumes; 10 gland dose exposures; and 150 spatial features). We performed feature selection using information gain on the entire dataset for voice dysfunction features and using 10-fold cross-validation for xerostomia features.

B. Models

We trained linear regression and naïve Bayes models with and without bagging, as well as a random forest model for both toxicities. 1000 iterations was used both for bagging as well as RF. At each node RF randomly selected two features during voice dysfuction training and four features during xerostomia training. We evaluated the results using 10-fold cross-validation.

V. Results

A. Feature Selection

Table 1 presents the five top ranking voice dysfunction features. With the exception of $V_{eff}$, all of the high ranking features are spatial. LKB NTCP ranks $53^{rd}/79$. The table also provides coefficients from the linear regression model.

TABLE 1

Features selected for voice dysfunction using entire dataset with linear regression coefficients.

| Information gain | Coeff. | Attribute |
|---|---|---|
| 0.104 | 0.2938 | 40-55 Gy lower 5th Z axis |
| 0.104 | 0.3092 | $V_{eff}$ |
| 0.101 | 0.3836 | 25-40 Gy 2nd lower 5th Z axis |
| 0.077 | 0.7714 | >70 Gy lower 5th Y axis |
| 0.077 | 0.6589 | 5-25 Gy lower 5th Y axis |

Table 2 provides the 19 features used for xerostomia modeling. Unlike voice dysfunction, LKB NTCP is most important feature for all of the folds. The highest ranking spatial feature is $12^{th}$. Feature marked "not used" in the table were provided to the linear regression trainer, but were not sufficiently informative to be included in the resulting model.

TABLE 2

Features selected for xerostomia using 10-fold cross-validation with linear regression coefficients.

| Avg. gain | Coeff. | Attribute |
|---|---|---|
| 0.11 ± 0.011 | −0.2461 | LKB NTCP |
| 0.084 ± 0.014 | 1.6513 | Right gland dose exposure 40-55 Gy |
| 0.08 ± 0.013 | Not used | Left parotid $D_{max}$ |
| 0.077 ± 0.012 | 1.2516 | Right gland dose exposure >70 Gy |
| 0.077 ± 0.011 | 0.0000 | Right parotid $D_{max}$ |
| 0.076 ± 0.012 | −1.2108 | Left gland dose exposure 55-70 Gy |
| 0.073 ± 0.008 | Not used | Combined $V_{eff}$ |
| 0.075 ± 0.012 | 1.7048 | Left gland dose exposure >70 Gy |
| 0.075 ± 0.012 | −1.1185 | Right gland dose exposure 55-70 Gy |
| 0.07 ± 0.009 | 1.8110 | Left gland dose exposure 40-55 Gy |
| 0.067 ± 0.011 | 0.0000 | Combined $D_{max}$ |
| 0.054 ± 0.006 | 0.2986 | 25-40 Gy 2nd lower 5th Z axis, right |
| 0.052 ± 0.005 | Not used | 55-70 Gy middle 5th Z axis, right |
| 0.046 ± 0.007 | Not used | 40-55 Gy middle 5th Z axis, left |
| 0.05 ± 0.006 | Not used | Right parotid $V_{eff}$ |
| 0.046 ± 0.008 | Not used | 25-40 Gy middle 5th Z axis, right |
| 0.045 ± 0.005 | Not used | 40-55 2nd lower 5th Z axis, right |
| 0.043 ± 0.007 | 0.7167 | 25-40 Gy highest fifth 5th X axis, left |
| 0.043 ± 0.015 | Not used | Left gland dose exposure 25-40 Gy |

TABLE 3

AUC values using 10-fold cross validation

| Method | Voice dysfunction n = 99, $n_+$ = 8, $n_-$ = 91 | Xerostomia n = 364, $n_+$ = 275, $n_-$ = 89 |
|---|---|---|
| BNB (1000 iter.) | 0.915 | 0.743 |
| BLR (1000 iter.) | 0.905 | 0.737 |
| NB | 0.900 | 0.734 |
| LR | 0.896 | 0.731 |
| RF (1000 trees) | 0.724 | 0.674 |
| LKB | 0.596 | 0.700 |

VI. Discussion

A. Model Validity

Model validity can be assessed in four contexts: face validity—e.g. the model's complication risk should increase with dose intensity; internal validity—e.g. the receiver operating characteristic area under the curve should demonstrate under cross-validation that the model's predictions are consistent with the data available; external validity—the models created should perform well across multiple dataset, ideally from external institutions; clinical utility—the models should provide a clear improvement in patient care [26].

When assessing face validity for xerostomia LR, the negative coefficients for LKB NTCP (−0.2461), left gland dose exposure 55-70 Gy (−1.2108), and right gland dose exposure 55-70 Gy (−1.1185) are of concern. The negative coefficients demonstrate a reliance on correlation amongst the features—if the features were independent then a negative coefficient for LKB NTCP would remove face validity. The correlation may be due to idiosyncratic patterns in treatment planning. The model's predictive performance therefore could degrade due to changes in treatment planning that have a neutral or positive impact on patient care.

The modeling outperformance of LKB NTCP in both toxicities supports the internal validity of the models. Further, the high AUC values for the voice dysfunction models may lead to clinically useful metrics for treatment planning.

At present, Oncospace contains Johns Hopkins Radiation Oncology patients exclusively. Extending the project to other treatment sites will provide the opportunity for external validation. External validation can also protect against the modeling of idiosyncrasies described previously.

B. Feature Relevance

The importance of spatial features on voice dysfunction outcome supports Dornfield et al. [31] In addition, the relatively low AUC for LKB NTCP also lend credence to non-uniform functionality of the larynx with respect to dose. However, gland exposure, and dose bands above 4,000 cGy appear to contribute to xerostomia risk.

C. Random Forest Underperformance

NB and LR are both high bias, low variance models. RF's often can outperform both methods. RF's individual trees reduce bias by dividing the data sample into sub-samples and then make predictions based on the smaller groups. The large number of trees—each trained using a different bagged dataset and, with randomly selected fields at each node—limits increases in variance. We expect as patient cases increases from the hundreds to the thousands, RF performance to improve, ideally surpassing BNB.

D. Benefits and Pitfalls of Machine Learning

A machine learning approach has a number of benefits. Unlike animal models, the results are directly applicable to human patients. The research is less costly and labor intensive than clinical trial, or manually segmenting images outside of the clinical workflow. Further, machine learning offers the possibility of personalized medicine by incorporating features reflecting medical history, chemotherapy, demographics, etc.

The negative linear regression coefficients discussed in the Model Validity section points to the chief drawback of machine learning—the models are data driven, not based on the underlying biological process. Clinical interpretation of machine learning results is essential.

E. Other Embodiments

As mentioned in the previous section, clinical interpretation and validation of the results can also be achieved. Xerostomia can be further modeled. Many of the highly ranked features measured dosages over entire individual glands. Therefore interactions between both the parotid and submandibular gland can be examined by modeling risk across the entire mandible region.

VII. Conclusion

Using prospectively collected treatment planning data from Oncospace [18], we created both spatial and DVH based features for NTCP modeling. All features are calculated directly from the data without need for further manual involvement.

After feature selection, we created five machine learning models each for two complications—voice change and xerostomia.

A. Specific Aims

After a century of treating cancer patients with radiation, we still struggle to predict normal tissue toxicity with enough accuracy to make critical clinical decisions. Normal tissue dose limits remain based on a few dose-volume attributes, and decisions are made on a population basis based on sparse data from a few clinical trials and retrospective studies. Current radiobiological models assume that there exists a uniform dose to anatomical structures that will have the equivalent biological effect as the complex non-uniform doses that are delivered with every treatment to every patient. These models assume that every part of the identified anatomy contributes equally to the biological function of that anatomy and that each part is equally sensitive to radiation. These models simply fail to adequately model the impact of radiation on human function. This is done historically to fit the data to simplistic clinical models created long before the availability of computing power capable of analyzing complex, multidimensional problems. To advance our understanding of radiation effects on normal tissues, we must embrace the potential of "big data" predictive analytics for insight discovery.

We propose a local-level learning heath system for radiation therapy. This will serve as a working example in the greater oncology community, harnessing the potential of big data to help resolve long term knowledge deficits that are critical to cancer management. Where several groups hypothesize about data-driven learning health systems at a high level, our system is a tangible, realistic implementation that can be emblematic of future systems across oncology.

One of the primary reasons for current knowledge deficits in oncology is because toxicities are complex and often delayed, with laboratory studies requiring imaging and physiologic monitoring of primates for years after exposure [43, 44]. However, we treat cancer patients every day and simply fail to collect the data with enough detail to understand it with good resolving power. We have changed this practice by systematically collecting structured data in the clinical workflow for head and neck cancer patients. During each physical or virtual patient encounter, treatment related toxicities, functional measures, quality of life, and disease status are recorded. This clinical data is combined with the 3-dimensional (3D) dosimetry in our Oncospace database.

The radiation-toxicity relationship is complex due to the 3D nature of dose and the complex function of the anatomy. For example, xerostomia involves a combination of parotid and submandibular glands, and portions of each may be more sensitive to the actual patient function. Dysphagia involves several muscles responsible for swallowing that may compensate for one another after radiotherapy. It may be crucial to spare a particular muscle if other muscles are impacted by the disease or impossible to spare dosimetrically.

One goal of one embodiment of this project is to apply a learning health system model to expand our knowledge beyond the standard dose-volume relationship with clinical outcome. This spatial dose distribution in the defined anatomy, coupled with non-radiation related patient information can substantially improve our prediction of treatment outcomes for individual patients. Toxicities are what limit our ability to treat the disease; refining our ability to predict the risk will ultimately improve our ability to deliver lethal doses to the tumor.

Given existing anatomy, we propose to automatically identify spatially dependent features of the anatomy that correspond across the patients and evaluate their dosimetric characteristics. These features provide more refined spatial information about our dose that can be included in risk prediction models.

Furthermore, each patient can be different. They can present with different baseline function, different diseases, different medical and genetic histories, and different sensitivities. They can have different treatment intents and different tolerance levels for adverse effects. These can all play a role in the decision making for treatment plans, symptom management, and the overall course of care for cancer patients. At a core of a decision making process can be the ability to accurately predict risks for each individual patient. Improved, prediction of the risk of treatment related toxicity and disease control can substantially improve outcomes for our patients.

One goal is for generalizable risk prediction models with machine learning algorithms and use the variable features that most impact a particular toxicity or outcome for stratified groups of patients. The objective is to develop data science models that maximize the significance of prediction. Finally, we will ascertain the clinical utility for treatment plan quality assessment and care management individualized to the patient.

B. Background and Significance

There is a growing consensus that the future of patient care will be an integration of a learning health system and clinical expertise to provide personalized medicine. A learning health system promises to bring the power of big data to the patient bedside by deriving knowledge from electronic health records and applying it to clinical decisions. The system learns from each new patient as interventions and outcomes are recorded. Successful approaches can include seamless alignment with current clinical practice consistent with existing clinical knowledge, experience and workflow.

The fundamental practice of medicine begins with a diagnosis and assessment of prognostic indicators about the individual patient. Then a decision is made on the most appropriate intervention and therapy to achieve the best possible outcome. With each patient, physicians gain experience and understanding that they apply to new patients. Currently, experiences are primarily shared through publications and the results of clinical trials [45, 46]. With a learning health system, the generation and dissemination of knowledge can be enhanced by providing both access to recorded prior experience and the processing power of computers to resolve predicted outcomes from a multitude of prognostic and therapeutic factors.

Of all branches of medicine, oncology is particularly suited to benefit from a learning health system [47]. Cancer outcomes are somewhat variable and depend on multiple patient, treatment, and disease related factors. Clinical decisions are currently based on practice guidelines [48-50] and the experience of the individual physicians. These guidelines are not capable of including the many factors related to outcome in their decision trees. A learning health system, coupled with high quality clinical data, offers the opportunity to bring complex multivariate predictive modeling to improve outcomes and quality of life for cancer patients.

A goal for one embodiment includes validating a learning heath system in the oncology setting, with specific application to radiation therapy as a working example of how big data can improve decisions and individualize medicine for patients. To our knowledge such an example does not exist in current oncology practice.

B.1. A Learning Health Example: Predicting Radiation-Induced Normal Tissue Complications The practice of radiation therapy relies on an ability to balance treatment related toxicities with disease control. There are many decisions made during the course of care from choosing the optimal treatment plan, to symptom management and nutritional and psychological support. Each patient is different, and early prediction of patient-specific complications is essential to ensuring the best possible outcomes [51].

For example, the presence of human papilloma virus (HPV) has increased the prevalence of head and neck cancer and may have a profound impact on treatment decisions. Despite improved survival gains with HPV positive cancers, several treatment-related complications have been shown to increase over time [52-54] This includes a spectrum of swallowing complications ranging from silent aspiration to enteral dependence for nutrition (i.e. feeding tube) that significantly impact quality of life [55-58]. We have prospectively acquired the HPV status for nearly 600 head and neck cancer patients since 2012, currently accounting for 243 patients in our analytic database. A learning health system can enable this information to be processed and formulated into predictive models that benefit future patients. This can shorten the bridge between prospective data collection and practice-changing insight discovery.

Wide spread adoption of intensity modulated radiotherapy (IMRT) has also had a significant impact on outcomes for head and neck cancer patients. This includes reducing the incidence and severity of late xerostomia, [59-61] though there is evidence that further improvements are possible [62]. Changes in vocal quality [63, 64] and taste sensation [65, 66] are also common factors in head and neck cancer that impact a patient's quality of life. We have prospectively recorded radiation-induced toxicities for over 500 patients in our analytic database. As such, understanding the impact of current treatment modalities on both acute and chronic toxicities remains a strong focal point.

Many studies have been published on radiation-induced toxicities over the past two decades, as documented by a recent initiative known as the Quantitative Analysis of Normal Tissue Effects in the Clinic (QUANTEC) [67, 68]. Despite the tremendous body of literature reviewed, it is clear that current knowledge is limited by a lack of prospective data collection tools, large scale data storage solutions, advanced toxicity modeling and validation tools, and the resources to facilitate a "data-pooling culture" [68, 69]. These are all components comprising a clinical learning health system. We are actively addressing the challenges of prospective data collection and storage through in-house, web-based mobile solutions and other custom extract-transform-load (ETL) tools. Preliminary normal tissue complication probability (NTCP) models are also being explored.

The QUANTEC reports also highlight limitations in existing NTCP models [68, 70]. In particular, the models ignore the 3D nature of radiation dose and complex anatomical function, instead relying on simplified data reduction techniques. Patient medical history, lifestyle and chemotherapy are also typically ignored. By improving the prediction of NTCP, the quality of treatment plans and effectiveness of treatment will be improved.

Computer systems that store toxicity and 3D dose will enable a better understanding of the relationship between dose and NTCP [71]. Modern machine learning algorithms are very capable of understanding complex multi-dimensional data that often is not translatable to publications or to simpler clinical guidelines. For example, one might ask the system, "What is the risk of xerostomia given this dose distribution, the patient diagnosis, history and baseline function and concurrent therapies?" and a system could search a database, identify similar previous patients with comparable dose distributions and characteristics, and use the previous patient outcomes to predict the risk.

Our clinic, through our Oncospace program, has adopted a culture of prospective data collection in the clinical workflow to enable the evaluation and monitoring of toxicity and disease response for all of our patients, in particular for head and neck and thoracic cancers. One goal of this proposal is to accelerate the gain in knowledge that traditionally comes from clinical trials by using the full clinical data of all patients, and having it "live." The acceleration is accomplished by using pragmatic controlled trials to shorten the feedback loop. To bring this knowledge to the individual patient, the system must be able to present predictions of outcomes that consider all aspects of the patient and present it in a form suitable for making clinical decisions.

Our proposal addresses the challenge of developing a clinical learning health system by combining our Oncospace knowledge database with predictive modeling and presenting the predictions in a form that enables physicians to make clinical decisions for new patients.

B.2. The Learning Health System in the Clinic

Figure 26B:
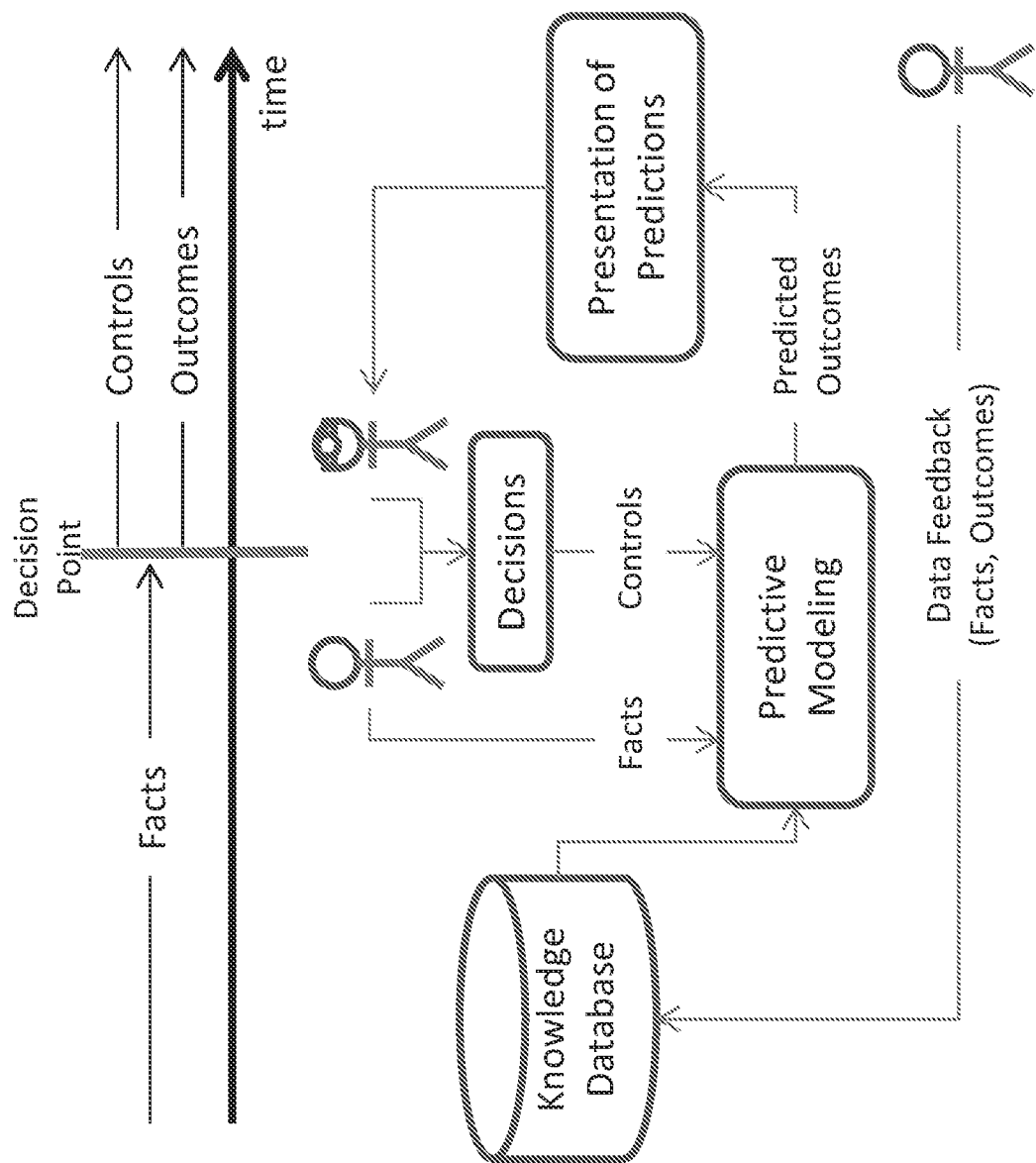
FIG. 26B shows a graphical depiction of a learning health system, according to an embodiment of the invention.

When creating a clinical decision support system, it is essential to provide actionable results that are relevant to the patient's current status [72]. An approach for applying the learning health system model to clinical decision support is depicted in FIG. 26B. It consists of a knowledge base of prior patient data, a set of predictive models, and a means to present the predictions to care providers and patients to assist them in decision making based on a new patient's status. As patients finish treatment and are evaluated in follow-up, feedback of new data allows the system to continually learn.

To design a system that permits the delivery of current and actionable decision support, we categorize available data concerning the patient into three types. The data types are dependent on the moment of the decision point in the course of care for the patient.

Facts or fixed data are information about the patient that cannot change. Examples are gender, race, diagnosis and genetics. Also included are facts that have already happened, such as baseline toxicity, or prior medications that have been used, or measured disease response.

Controls can be what can be changed or adjusted for a patient during the course of care. This includes symptom management such as future medication or nutritional support. It also includes any changes that can be made to treatment such as modifying the treatment doses.

Outcomes can be those data that represent the measures of disease control, treatment related toxicities, and the quality of life of the patient. These are measures of how well we have cared for the patient and represent the things to improve upon in a learning health system.

Patients are on a timeline as they go through treatment. As they progress, both control data and outcome data can become factual data. For example, at the midpoint of therapy, all current medications, existing toxicities, or disease response measures can become facts. These new facts can influence a subset of many control variables in radiotherapy (RT), including the remaining radiation dose, symptom management, prescribed medications, nutritional support (e.g., a feeding tube), and physical therapy.

The goal of a decision support system is to use a representation of the facts and control data (known as a feature vector) to predict the outcomes for patients. Then, given a new patient, the support system can allow physicians to explore the impact of varying the remaining control data on the outcome predictions. The decision support therefore assists the decision to modify control variables to achieve the best expected outcomes for the individual patient.

The learning health system must have the depth, granularity, and volume of data to predict outcomes with enough statistical power to be safe for patients. The system depends on prior patient data to make predictions for new patients. The knowledge can be contained in the data with sufficient detail to make critical decisions.

For the example model of dose versus toxicity, the control data is our radiation treatment plan, which contains the 3D dose distribution delivered to the patient. The facts are the patient anatomy, the tumor and target regions for treatment, patient history, concurrent therapies, baseline function, and diagnosis. The outcomes are disease status, treatment related toxicities, and quality of life. The ultimate goal is to establish a learning health system that allows us to create a better treatment plan that controls the disease while minimizing the toxicity.

The specific aims within this proposal represent the construction of a generalized learning health system model with application to our specific clinical example of radiation-induced complications. However, the proposed learning health system can be applicable to many other research topics as well.

B. 3. The Culture of Data Collection in the Clinical Workflow

For the system to be valuable, the data contained in the knowledge base must have enough depth and granularity to extend the knowledge of the physician. This means the treatment related data and the outcome data must have enough detail to allow clinical predictions that are at the level of the decisions to be made. For example, routine weight measurements only provide a superficial mechanism for tracking weight loss, which is an established negative prognostic factor for head and neck cancer patients [73-75]. We routinely assess radiation-induced complications [76], quantify swallowing function [57], and collect patient-reported quality of life information [77, 78]. This provides rich, detailed data that indicates how treatment controls should be modified to address the primary cause(s) of excess weight loss and to improve quality of life.

Figure 27:
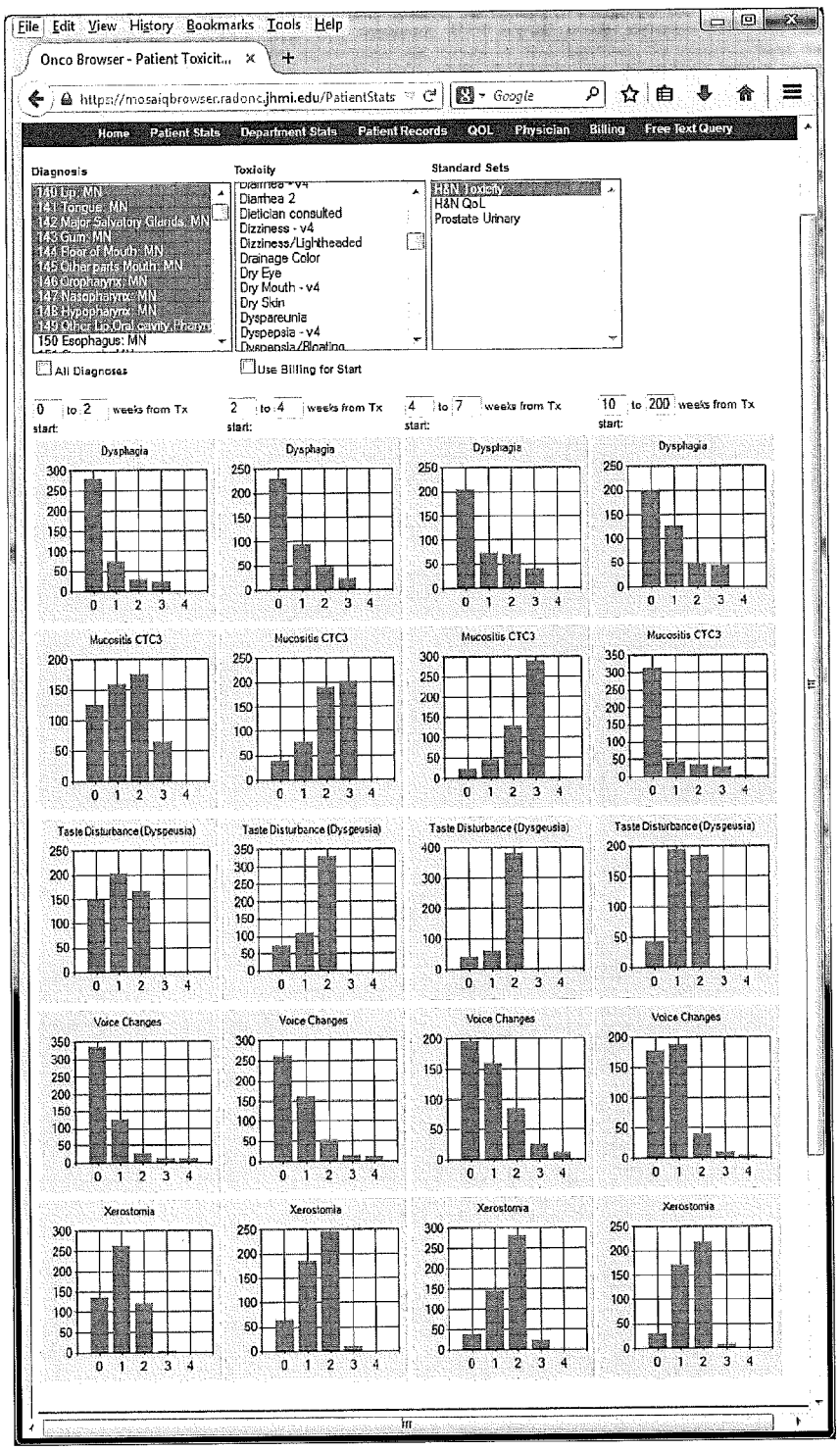
FIG. 27 shows a web page displaying toxicity distributions for head and neck cancer from start of treatment through follow up, according to an embodiment of the invention.

For example, in FIG. 27, a web page displays toxicity distributions for head and neck cancer from start of treatment through follow up. Dysphagia, Mucositis, Taste Disturbance, Voice Change and Xerostomia are selected. Each plot shows the number of patients experiencing each grade (0-4) of toxicity during the specified time periods. (0-2 wks, 2-4 wks, 4-7 wks and 10-200 wks).

The current practice of data collection for clinical trials relies on dedicated personnel to examine the patient, and manually review medical records and dictations in order to fill out paper-based forms identifying the specific data to be collected for the trial. These forms are then sent to collection centers like the Quality Assurance Review Center (QARC) or the Radiation Therapy Oncology Group (RTOG), and the information from the form is re-entered into a database created specifically for the trial. This process inherently limits the scope of information collected and is extremely inefficient given the technologies available today. The mindset towards data collection must change to one in which we ask: "How should the clinical process be modified to collect specific clinical and treatment knowledge for a particular cohort of patients?"

Since 2008, our department has made great strides in incorporating data collection directly into the workflow. Specifically, with commercial interest and support from Elekta Oncology, we have developed web-based tools for mobile devices that align with the typical patient encounter making the data collection seamless [79]. This was first adopted by our head and neck service and has now been applied for every clinical service in our department. Treatment related toxicities, disease status, quality of life, and patient vitals are collected in a standardized format on a daily or weekly basis without the additional need for data management. It is also possible to store many other types of data (e.g., radiomics, tissue biopsy details, etc.) within the current database schema, although new data types may require specialized extract-transform-load (ETL) routines. By reviewing this data through our custom web-based framework (FIG. 27), physicians have the ability to learn from previous patients in order to improve care for future patients.

We are actively exporting our culture of data collection through a consortium of institutions that share our vision. The Oncospace consortium shares the technologies through a common source code repository. The consortium also shares data by federating Oncospace databases housed at each institution. Current participating institutions include the University of Washington, University of Virginia, University of Toronto—Sunnybrook, and Washington University.

In order to maintain semantic interoperability across the consortium, the majority of our data dictionary adheres to standards. Our toxicities use the National Cancer Institute's Common Terminology Criteria for Adverse Events (NCI-CTCAE) which scores them from 0 (no toxicity) to 5 (death). In several instances though, this scoring is too coarse and higher resolution scoring has been defined to better characterize the assessment. Quality of Life instruments have also been shown to provide quantitative knowledge of the patient's well-being. These instruments are validated through multiple studies. For head and neck cancer patients, the Functional Assessment of Cancer Therapy-Head and Neck and the MD Anderson Dysphagia Inventory are used for patient reported general wellbeing and swallowing function.

A culture of data collection is required for successful implementation of the learning health system. We have embraced this culture at our institution, and many other institutions share the mindset. Therefore, the implementation of a generalized learning health system can have a broad impact in the cancer community.

B.4. Knowledge Database and Data Integrity in Radiation Oncology

Access to the knowledge is also limited by how the data is aggregated and housed. Clinical information and treatment planning systems are designed to carry out clinical care for patients. These systems are not designed to aggregate the data for analysis and experience sharing. In order to store our full clinical experience, we have designed an RT-specific relational database.

The data tables are arranged to support patient geometry, targets and organs at risk (OARs) and their spatial relationships, dose distributions and dose volume histograms (DVHs), toxicities, diagnosis and disease progression, chemotherapy and medications, laboratory values, patient histories and demographics. The database schema (FIG. 23) is arranged such that the patient table is central to all other data collection.

Personal health information (PHI) is isolated in a single table, enabling the database to be anonymous when this table is removed or access is restricted. In addition to PHI, it stores a reference date to which all other dates in the system are relative. This date is typically the first day of treatment, thus all dates are in days from first treatment.

Since 2008, we have routinely collected and stored treatment and clinical data for HN patients treated at our institution. A collection of custom scripts and user-interfaces has helped to streamline and integrate the data collection process into the daily clinical workflow. As a result, we actively maintain a culture of prospective data collection within the HN service.

Figure 28:
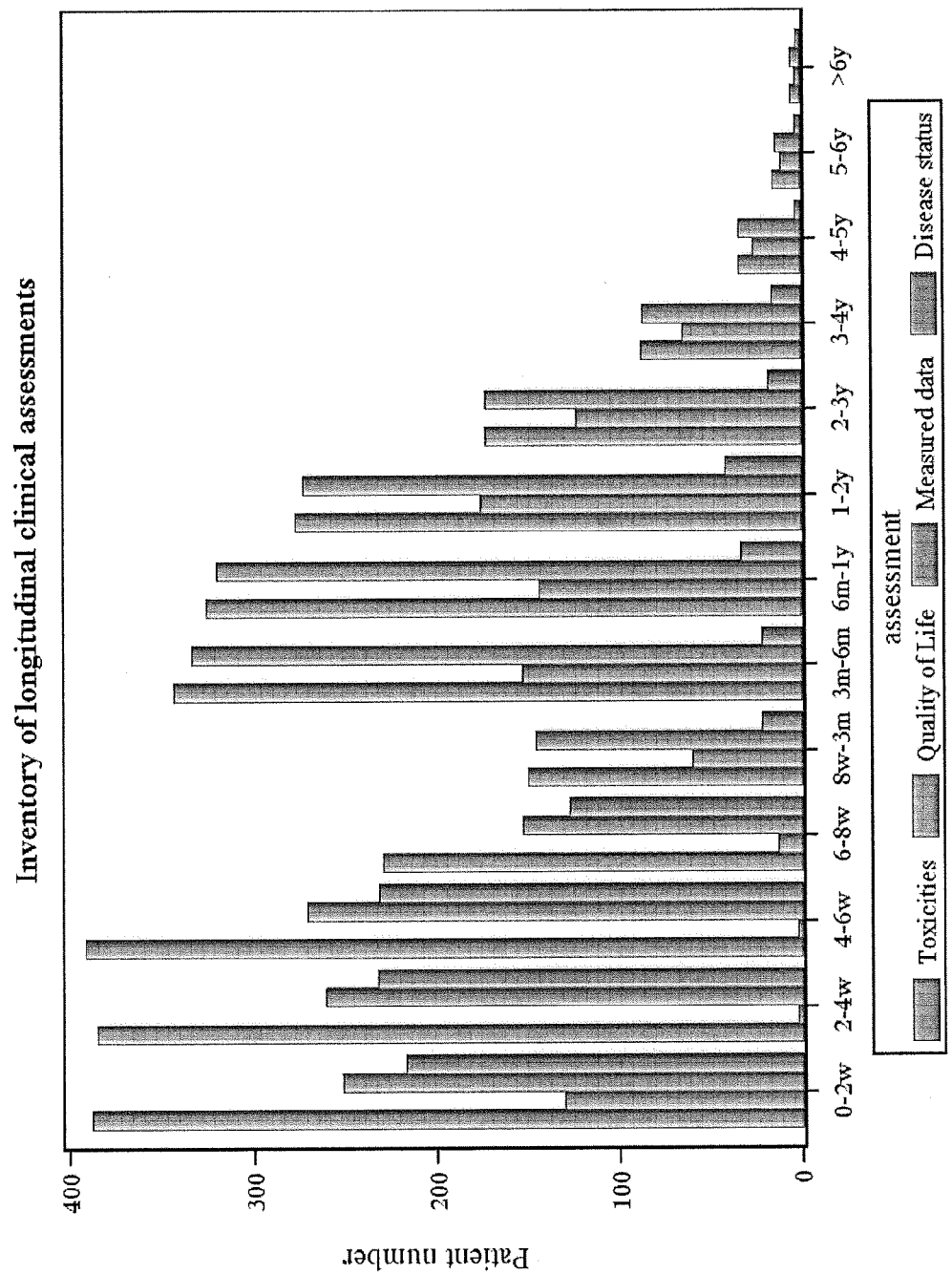
FIG. 28 shows the number of patients with specific types of clinical data in the head and neck database within each specified time period, according to an embodiment of the invention.

FIG. 28 shows the current inventory of our longitudinal clinical data, including over 6 years of patient follow up. For each patient represented in FIG. 28, 16-45 anatomical structures and 1-5 target volumes with complete dosimetry and shape relationships are also stored. This data has the depth and granularity needed to begin to address the proposed models of how the dosimetry relates to toxicities in our population of patients. All data is captured as part of our routine clinical workflow. The average number of data elements per patient, per visit are 33 for toxicities, 40 for quality of life, 9 for disease status and 5 for measurements.

To address data integrity, tools are being developed to assist with identifying possible errant data in the system. These tools evaluate data for consistency and completeness. As with any clinical information, the data can be improperly recorded. Integrity checks offer a way to systematically look for errant data to report and correct. We can detect inconsistencies such as large variations in longitudinal weight measurements when data is entered in both lbs and kg, or when an OAR's volume or location is inconsistent with normal anatomy. These integrity checks are built into the framework and will evolve over time as we identify new ways of validating the data in the system.

The aggregation of patient data and the continual improvement in data integrity will enable our system to gain knowledge over time, enhancing the capacity of the learning health system for decision making.

B.5. The Predictive Models

Medicine poses several challenges to data science. A considerable amount of relevant data is, in general, subjective as we are dealing with clinical assessments of well-being and quality of life. There is also inherent uncertainty in the data. There are sampling issues where we only assess key patient facts at certain time points. The presence of highly correlated variables also poses a problem for two reasons: (1) a correlative parameter may be highly misleading if identified in the absence of true causative factors, and (2) multiple correlative factors may obscure the single most representative predictor of outcomes.

Fayyad, et al. introduced what is generally considered the fundamentals of the process for knowledge discovery in databases (KDD) [80]. Typically the vast majority of data analyzed was not collected for that purpose, but rather in the course of an institution conducting its general activities. In the case of health-care, data is generally from electronic health records (EHR), or other components within hospital information system.

Fayyad, et al. divides KDD into nine steps: (1) understanding the problem domain and the previous work in the area; (2) selecting a target dataset; (3) data cleaning and preprocessing; (4) data reduction and projection; (5) matching the knowledge discovery goals with a data mining approach; (6) exploratory analysis with hypothesis and model testing; (7) data mining; (8) interpreting results; and (9) acting on discovered knowledge [80].

KDD primarily addresses situations where the original data is unstructured and stored in relational database systems. For this proposal we distinguish between structured and unstructured data based on the level of preprocessing required. For example, data fields such as height, weight, name, address, etc. are structured fields. Images, free-text, dose grids, etc. are unstructured data. Often, unstructured data are stored in files, not relational database management systems (RDBMS). When unstructured data are within a RDBMS, they are normally stored in binary large object (BLOB) or character large object (CLOB) fields.

The emerging area of data science addresses the requirements unstructured data imposes. A key requirement for a data science platform is an analytic sandbox that is separate from the organizational data repository. Due to the lack of statistical proofs of confidence in most data mining algorithms, data science modeling involves "failing enough." In other words, this involves experimenting with enough models and data transformations to ensure that the most superior model(s) demonstrate true predictive advantages. The analytic sandbox allows for conducting research without risking the original data stores [81].

The first step in machine learning is to represent a patient as a set of features referred to as a feature vector. Feature selection is a process of selecting the most informative features from an initial set of candidates. In 3D treatment planning risk modeling, features are transformations of the raw dosimetric and spatial data. We will refer to a set of feature vectors (patients) as a dataset.

A trainer algorithm uses a set of feature vectors (training data) to learn (or train) a model. From a workflow perspective, the trainer receives the feature vectors as input and returns a model as the output. Training vectors will contain outcome as one of the features. In the case of NTCP modeling, the model established by the trainer represents a classifier. The classifier accepts new feature vectors, and computes a prediction of the presence of the complication. The trainer algorithm and the set of resulting models together form a machine learning technique.

Machine learning approaches have a number of benefits to clinical practice. They incorporate real patient data and produce results that are directly applicable to future patients. Further, machine learning offers the possibility of personalized medicine by incorporating features that reflect medical history, chemotherapy, demographics, etc. These methods are anticipated to be less costly and labor intensive than conducting fully randomized clinical trials, even while accumulating data on many more patients.

A drawback of machine learning is that the models are data driven, not based on the underlying biological process. Clinical interpretation of machine learning results is essential. This introduces the conundrum of correlation vs causation, where data driven prediction may find high correlation with data that are truly just surrogates for the underlying cause. For example, xerostomia is correlated with radiation dose to the mandible, even though the mandible has no role in salivary production. This is explained by the close proximity between the mandible and salivary glands, such that high mandible doses often indicate high glandular doses. Given a model based on the mandible, a patient with low mandible dose would be predicted to have a low risk of xerostomia. However, if the salivary glands actually received high doses relative to the mandible, the prediction could be quite wrong. This illustrates the importance of model validation in the context of known biological processes.

B. 6. The Presentation of the Prediction and Decisions

The presentation of modeled predictions completes the learning health system. The system should present the predictions, while also offering some ability to adjust the control variables to see how the predictions change the potential outcome of the patient. Currently, a web-based interface (FIGS. 27 and 29) is used to provide basic data transfer, review, and analysis. This allows access to the knowledge base from both personal computers and mobile devices.

In our example, one may see a prediction of a 40% risk in grade 2 xerostomia. They would then be given an opportunity to see how a change in dose distribution or symptom management would effect that prediction. The presentation display must provide, as part of the framework, the patient-specific facts and possible control variables to the system. This requires the learning health system to be interfaced with the clinical systems to provide access to the radiation dosimetry and clinical factors for the predictive modeling tools.

Some aims of an embodiment focus on the validation of the predictive models for use in the learning health system. The presentation of predictions and the ability to interact with decision controls can be developed to complete the components required for decision support. This fundamental system has applicability across the spectrum of medicine. The key components are the available data and the models of the learning health system. For our example, we have both the accuracy and detail in our data and the access to perform the predictive modeling.

C. Innovations

The innovations in the proposal are contained within our ability to apply our knowledge base to real individualized decisions within the learning health system. Our previous work in this area provides several examples of how we can use the data to improve the quality of care and the inclusion of clinical outcome measures and predictions into decision making.

C.1. Prediction of Organ Dose Constraints from Geometric Shape Relationships Our first learning initiative involved the concept of using a knowledge base of prior treatment plans to predict the achievable plan quality for new patients. We recognized that the complex geometrical relationship between critical anatomy and the targeted tissues was predictive of our ability to spare the critical anatomy from radiation damage. In this case, the facts are the geometrical relationships between targets and risk structures, and the outcome is a knowledge-based estimate of the best possible dose distribution for each new patient.

Figure 29:
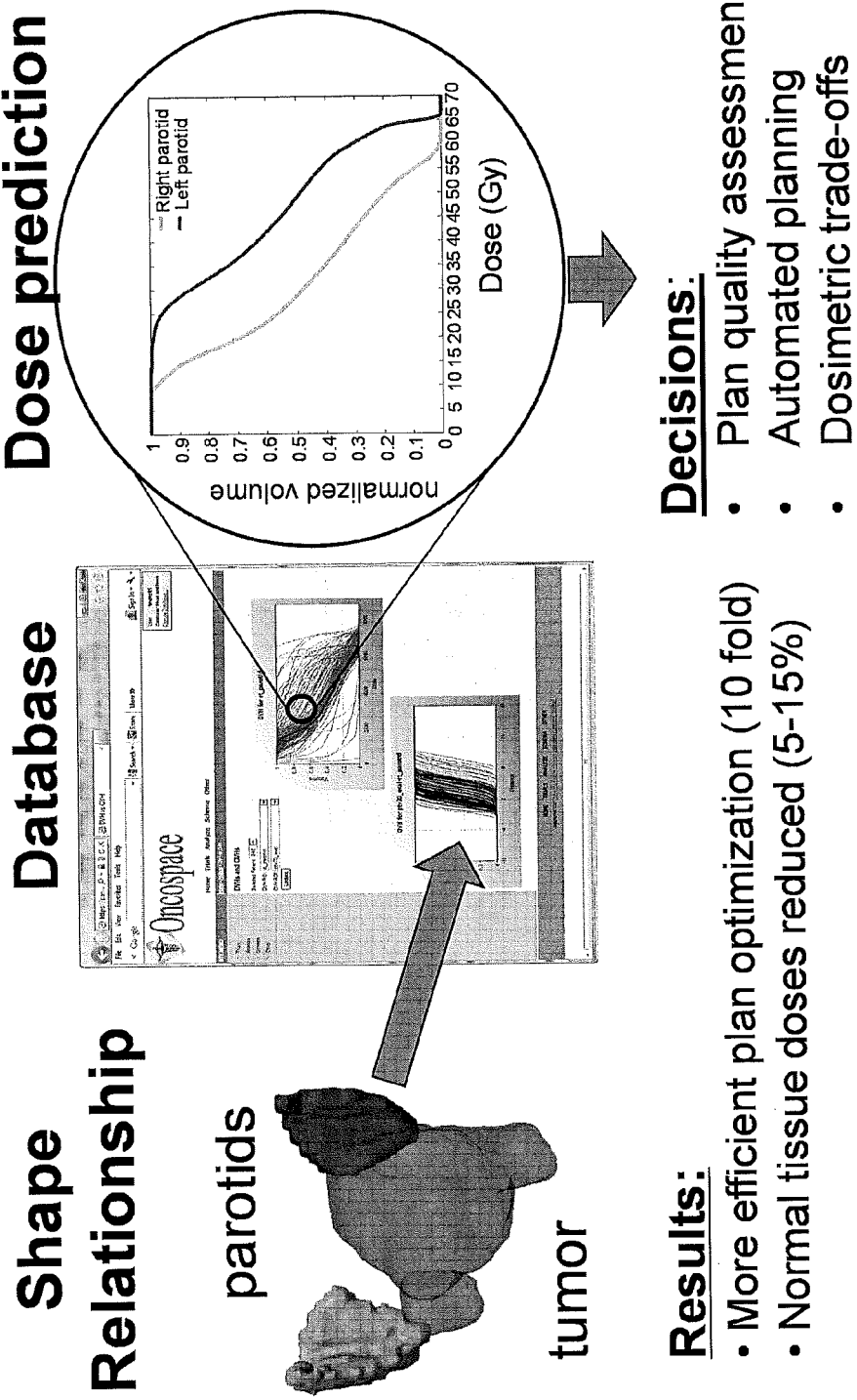
FIG. 29 shows a flowchart for selecting a treatment plan, according to an embodiment of the invention.
Figure 30:
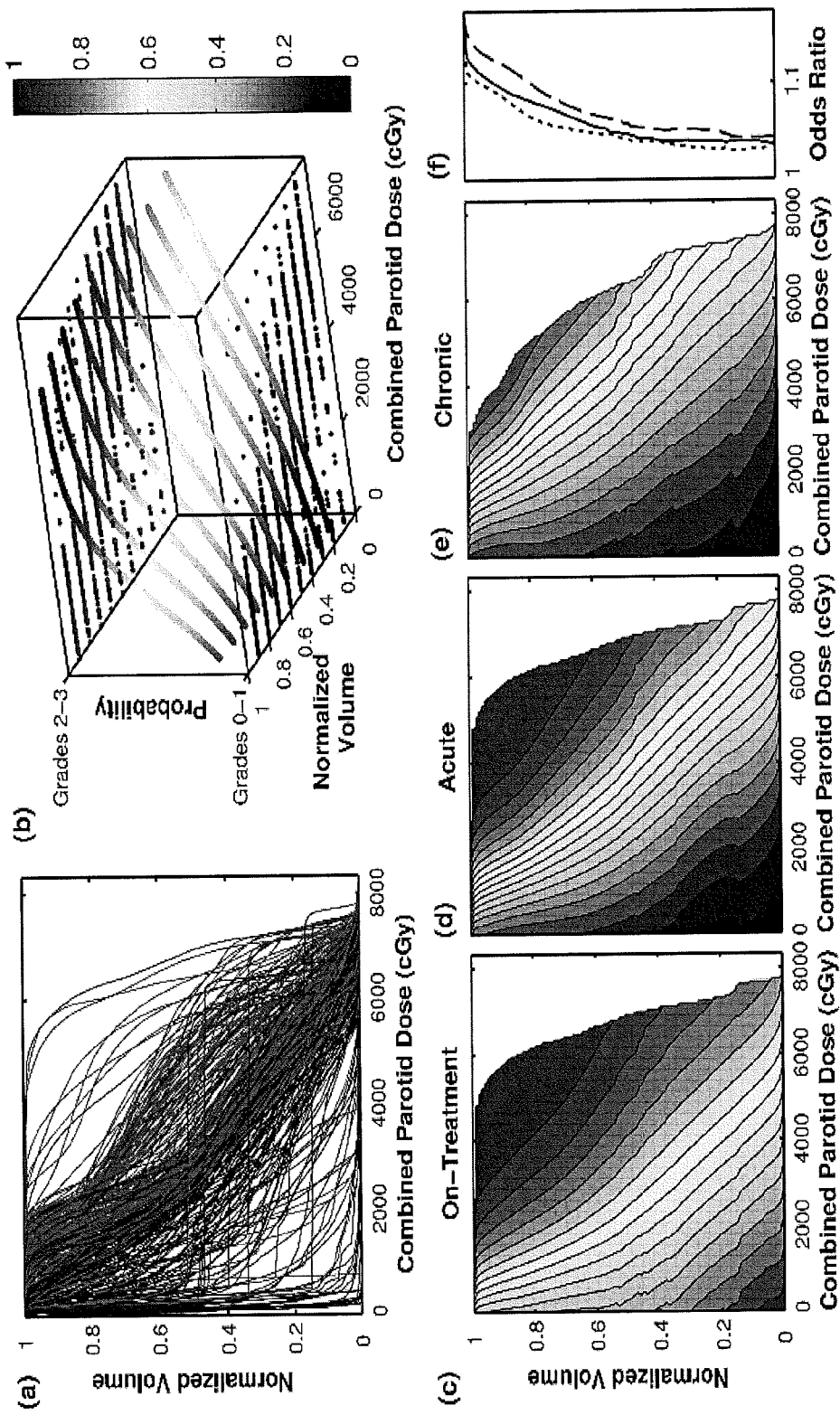
FIG. 30 (a) shows dose-volume histogram (DVH) curves for the combined parotid glands, with red and blue curves denoting patients with grades 0 to 1 ("low grade") and grades 2 to 3 ("high grade") acute xerostomia, respectively. (b) shows logistic regression curves between low-grade (blue points) and high-grade (red points) toxicity groups at normalized volume thresholds from 10% to 90%, in 10% increments. (c)-(e) show logistic regression curves computed from 0% to 100% in 1% increments, demonstrating the prevalence of high-grade xerostomia during treatment, acutely, and chronically. (f) shows odds ratios for on-treatment (solid), acute (dashed), and chronic (dotted) logistic models.

The ability to spare Organs at Risk (OAR) using IMRT depends on the geometric relationship of each OAR to the target volume. OARs in close proximity to the target are much harder to spare than those far away. To formalize this relationship, we introduced the concept of an overlap volume histogram (OVH) [82, 83]. An OVH indicates how far away a given percent of the OAR's volume is from a target. By relating OVH curves directly to DVH curves from treatment planning, we can predict the expected dose for new patients based on OAR proximity to the tumor (FIG. 29). For a selected organ at risk and percent volume, find the lowest dose achieved from all patients whose percent volume is closer to the selected target volume. This question is the basis for geometry based IMRT plan automation and quality control where we predict dosimetric sparing from the database of prior patients as input to the IMRT planning process to create planning objectives for a new patient. We query the database for the lowest dose achieved for all previous patients having an OAR closer to the target (e.g., harder to spare) than the new patient's OAR [45, 46, 84, 85]. This query is repeated for all OARs at all desired normalized volume levels [85-87]. Our group has used this model to automate the IMRT planning process and to compare plan quality [88-90]. We have applied it to head and neck, thoracic, pancreatic and prostate cancers and have been using it clinically for over 3 years. Since then, commercial interest has evolved with Varian's knowledge-based treatment planning product, and a similar product now available through Philip's Pinnacle [45] treatment planning system.

The OVH can also assist with inter-institutional comparisons of plan quality, which becomes very important in comparing radiotherapy data across multiple institutions [91, 92]. For example, the OVH can be used in conjunction with other demographic and disease-related factors in propensity score matching [93-95]. By comparing patients with similar OVH's at the different institutions, it becomes possible to compare the efficacy of different planning techniques in meeting or exceeding normal tissue does constraints. As plan quality may directly influence patient outcomes both in terms of local tumor control and normal tissue toxicities, the OVH can be used to "normalize" variations in plan quality to improve the consistency of multi-institutional studies.

This work represents an established example of how our group has successfully applied our knowledge base to improving the quality of care and decision making for radiation therapy patients.

C.2. Dose-Volume Analysis of Normal Tissue Complication Probability

The next evolution of the proposed learning system is to apply it to the prediction of radiation-induced toxicities and treatment outcomes. Although shape relationships and dose are just a subset of the parameters associated with toxicities and outcomes, we can begin to build models that focus on predicting toxicities and outcomes experienced by the patients. Our group has shown how the data can be mined to find the predictive dosimetric factors from dose volume histograms of OARs and the clinical outcome of the patients.

To explore the variety and volume of treatment planning data and clinical outcomes available in the Oncospace database, we have established a general purpose data-mining graphical user interface for large-scale exploratory analysis of dose-toxicity relationships [96, 97]. Briefly, this involves a two-level hierarchical model: a top-level data-mining function for querying and iterating over combinations of risk structures and outcomes, and a subroutine for executing specific dose-outcome analyses.

The top-level function extracts OARs and outcomes that have been recorded in the database for at least 100 patients. Combination structures can be automatically created from paired OARs based on database naming conventions. For example, the differential DVH curves (absolute volume, absolute dose, and matching histogram bins) for "l_parotid" and "r_parotid" may be summed to generate a new differential DVH curve for the "combined_parotids." For quality of life and toxicity assessment, the query returns the severity of outcomes and the relative date of assessment, defined as the number of days after the first radiotherapy fraction. This allows outcome data to be analyzed as a function of time or over finite time intervals relative to the beginning of treatment. For each combination of OAR and outcome, patients that do not have both OAR and outcome records are excluded from analysis.

Because this data mining algorithm is intended to explore such a large number of OAR-outcome combinations, we require an analysis that is efficient to implement for each combination. However, given the depth of dose data in the database, we also desire a comprehensive model capable of exploring detailed dose-volume interactions. While several existing models are suitable to this end [98, 99], we implement a logistic regression model [100, 101]. This type of model enables one or more significant dose-volume planning objectives to be explored, as single points in dose-volume space may not adequately predict the risk of radiation-induced toxicities [70].

An example of the resulting logistic curves is shown in FIG. 30a. In FIG. 30b, the logistic regression curves are shown for analyses from 10% to 90% normalized volume, in 10% increments. By repeating the logistic regression analysis at a finer volume resolution (e.g. 1% increments), the probability of a given outcome may be visualized as a heat map (FIG. 30c-e), with high-gradient regions indicating a highly discriminating region in dose-volume space with respect to the given outcome.

To characterize the strength of the relationship between each combination of OAR and outcome, the odds ratio is derived directly from the logistic regression fitting parameters. A larger odds ratio indicates that the probability of an outcome is more strongly associated with an increase in OAR dose. The maximum odds ratio and associated normalized volume level for each OAR-outcome combination can therefore be used to identify the strongest dose-outcome relationships in the database.

From a total of 57 OAR and 97 outcomes, many were found to agree with literature-based recommendations. For example, the recommended mean dose to the combined parotid glands is approximately 25 Gy to limit the risk of severe xerostomia [102]. In this analysis, a dose of 27.5 Gy to 50% of the combined parotids resulted in a 50% probability of grade 2 or 3 xerostomia. It is also recommended that high doses to the ipsilateral parotid should be counteracted by doses less than 20 Gy to the contralateral parotid [63]. However, FIG. 30f demonstrates that the odds ratio for xerostomia increases with larger normalized volume thresholds. This supports the conclusion that the "low-dose bath" delivered to large volumes (>80%) of the combined parotid tissue may actually have a stronger influence on xerostomia than mean dose [103, 104]. This illustrates the ability of the current data-mining paradigm to explore the nature of dose-toxicity relationships from thousands of OAR-outcome combinations.

This work ultimately serves to (1) benchmark toxicity rates at our institution, (2) validate existing dose-volume planning objectives from literature, and (3) generate hypotheses on dose-outcome relationships that warrant further investigation. The results of the data-mining exercise do not yet serve as clinical recommendations.

C.3. Preliminary Exploration of Machine Learning Using Spatial Dose Distributions for NTCP Prediction The primary assumption in traditional NTCP models is that physiological effects (e.g. xerostomia) are directly related to the function of whole organs (e.g. salivary gland secretions). Recent studies have begun to demonstrate that models incorporating spatial, sub-organ dose information greatly enhance toxicity prediction [103-106]. However, these models are often tedious to generate, as current data storage solutions do not enable the simple access and manipulation of 3D dose data. To our knowledge, the Oncospace database is the first to store full 3D dose distributions along with 3D representations of target structures and OAR. Although the planned dose distribution is currently being stored, it is also possible to compute and save the estimated delivered dose to each patient, but the development of tools and methods for generating delivered dose distributions is outside the scope of this proposal.

Our group has created an analytic pipeline that transforms the data in Oncospace into a format suitable for creating multiple ad hoc NTCP prediction models [107, 108]. This includes incorporating spatial dose information and patient-specific factors to improve existing models. By creating a data science platform for robust, data-driven NTCP models, we hypothesize that (1) it is possible to create safer, more personalized treatment plans based on experience from prior patients, (2) these efforts will empower collaborative NTCP research involving much larger quantities of data than was ever possible before, and (3) this framework will encourage the exploration of advanced spatial dose features that capture sub-organ effects.

Creating a spatially dependent NTCP model requires features that reflect the distribution of dose throughout anatomical structures. This was accomplished in preliminary work by sectioning the structures into fifths along each cardinal patient axis: left-right, anterior-posterior, and superior-inferior. Each axis is evaluated separately, resulting in 15 overlapping sub-regions. Five features are generated within each sub-region based on the volume receiving one of five different dose levels, which were designated from clinical experience to be 5-25, 25-40, 40-55, 55-70, and >70 Gy. Thus, a total of 75 spatially dependent dose features can be computed for each structure. The traditional Lyman-Kutcher-Burman (LKB) model NTCP prediction is also included as a feature [109-112]. While many other feature engineering techniques are possible, the current methods enable proof-of-principle testing of the machine learning platform.

Figure 31A:
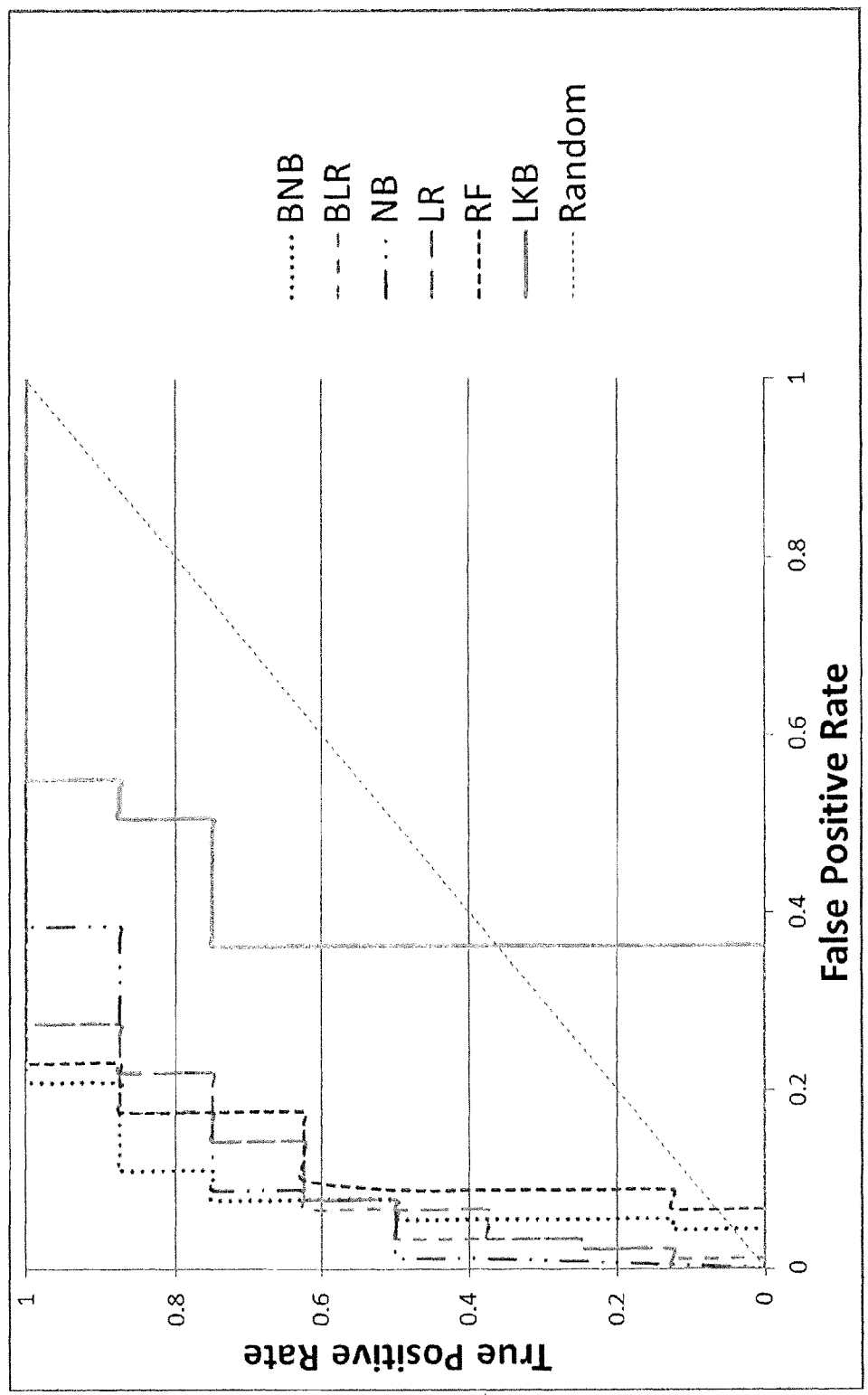
FIG. 31A shows receiver operating characteristic (ROC) curves for xerostomia and FIG. 31B shows receiver operating characteristic (ROC) curves for voice dysfunction for the following machine learning techniques: bagged naïve Bayes (BNB), bagged linear regression (BLR), naïve Bayes (NV), linear regression (LR), random forests (RF), and Lyman-Kitcher-Burman (LKB), according to an embodiment of the invention.
Figure 31B:
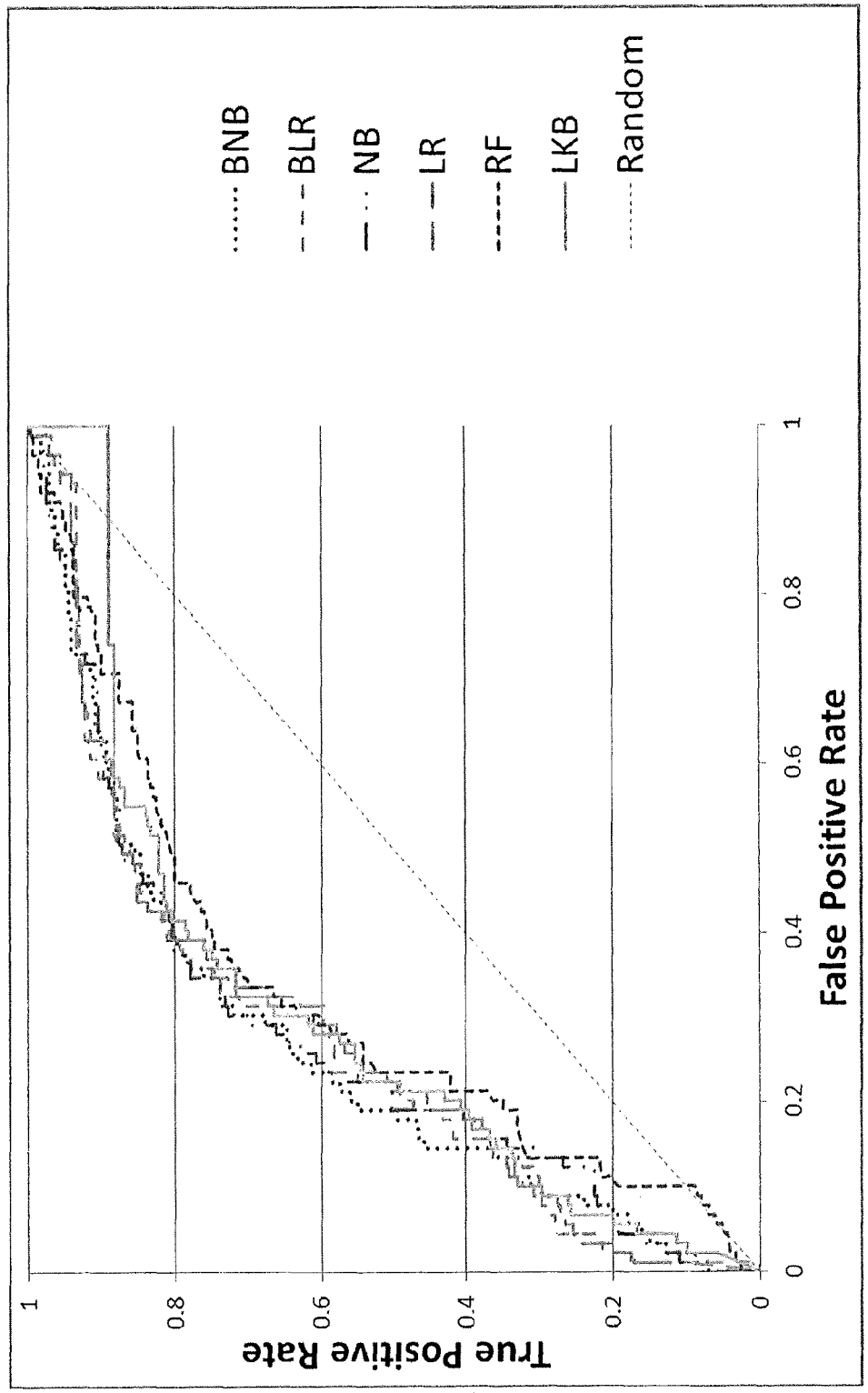

The set of best features is selected using information gain. Complications are modeled using the following machine learning algorithms: linear regression (LR), random forest (RF) [113], and naïve Bayes (NB). Bagging for LR (BLR) and NB (BNB) is also assessed to create more stable and accurate models by creating an ensemble of classifiers, each of which is trained on a dataset created by randomly sampling the training data [114]. Both bagging and RF use 1,000 iterations. FIGS. 31A and 31B present the receiver operating characteristic (ROC) curves for xerostomia and voice dysfunction, and FIG. 32 provides the corresponding area under each curve.

For xerostomia, none of the top 19 selected features were spatially dependent. The LKB NTCP prediction was found to be the single most important feature, with other informative features either based on DVH curves or related to dose from the combined (left+right) parotid glands. This supports the "parallel" nature of salivary glands, in which the overall function is distributed uniformly throughout the structures [68]. It is also in contrast to recent evidence suggesting a spatial dose dependence within the parotid glands [103, 104]. However, we believe this finding may be largely due to the current feature selection methods.

For voice change, four of the five most informative features were spatial features, with the fifth based on DVH analysis. The LKB NTCP prediction was not chosen as a feature, which may be due to the fact that LKB model parameters are more relevant to dysphagia than voice dysfunction. The spatial dependence of radiation dose on vocal changes makes sense physiologically, as voice changes are impacted by a small region within the larynx comprising the vocal cords and surrounding muscles. Physicians do not contour these structures during routine clinical practice. However, a spatially dependent NTCP model may be able to predict sub-organ physiological changes without explicitly contouring the implicated structures. Instead, sub-organ prediction models can be built upon gross anatomical structures (e.g., the larynx) that are routinely contoured for all patients. This has tremendous implications for the comprehensive modelling of swallowing dysfunction, which depends on the complex interaction between over thirty muscles and nerves [58, 115].

Through this work, we demonstrate the ability to generate complex 3D dose-toxicity models from our knowledge base.

D. Approach

We recognize that the advancement of NTCP models will only be possible by empowering collaborations between many different institutions. Contributions may include (1) treatment planning and follow-up data collected according to standardized formats and ontologies, (2) novel techniques for engineering advanced dose features from 3D spatial dose distributions, and (3) novel methods for exploring radiation effects in normal tissues. Our proposed learning health system for advanced radiobiological modeling embraces all of these efforts.

We envision Oncospace as an essential resource for next-generation insight discovery and clinical decision support. We have established the feasibility of routine, prospective data collection and storage. This not only provides large volumes of clinical information but also yields the depth of information necessary for a learning health system in the oncology setting. Our database storage solution enables treatment planning and toxicity information to be incorporated in all future studies. This is in direct contrast to what has been coined the "data-loss paradigm" in NTCP modeling [69]. The acquisition, storage, and retrieval of clinical information should no longer be a technical barrier to the pursuit of advanced dose-toxicity modeling.

The next major obstacle involves the engineering and extraction of sub-organ or sub-regional dose features without the burden of explicitly contouring these regions. Preliminary work has demonstrated the feasibility of feature extraction and the benefit of spatial dose information to improve predictive power. Many other studies are also beginning to explore the spatial effects of radiation in normal tissues, although through seemingly tedious efforts [104-106, 116]. In our proposed learning health platform, we aim to develop multiple methods for automatic spatial dose feature extraction. An open source platform will also enable other institutions to invent their own novel features. This supports creativity in feature development and flexibility in feature definitions as the quantity and quality of available data continually improves.

The third major obstacle involves the expertise to design methods that incorporate spatial dose features with other multivariate factors. A wide variety of machine learning and data mining algorithms currently exist to this end, some of which have been explored in preliminary work. However, we expect that these algorithms will continue to improve and propose to incorporate learning algorithms in a modular fashion. By decoupling the analysis from the raw data and feature extraction, we gain the ability to compare learning mechanisms. This approach again supports creativity and flexibility in future contributions to the proposed learning health system.

The final implication of our proposed system involves the potential for practice-changing discoveries as a result of the insight gleaned from an effective learning health system. It is no longer the responsibility of a single institution to influence the (inter-)national practice of medicine based on the publication of highly distilled information. Instead, we envision a general-purpose presentation layer that summarizes the learning process, the predictive model, and the implicated treatment decisions. The presentation layer will always be based on a prospectively acquired knowledge base, and it will continually incorporate new knowledge as patients are added to the database. Publications, even with supplementary data, cannot provide a comprehensive and scalable knowledge source capable of supporting a learning health system. Furthermore, as our proposed system is adopted by other institutions, the collection of single-institution studies is anticipated to result in rapid generation of new knowledge and widespread validation of best practices.

In summary, we have envisioned an open source learning platform for advanced radiobiological modeling based on highly customizable spatial dose features. This specific platform, along with the underlying data management infrastructure, can be of great benefit to the scientific and healthcare communities as we continue to improve our knowledge of radiation effects in normal tissues. We believe that advances in dose-toxicity modeling will greatly improve the potential for truly individualized patient care in radiotherapy.

D.1. Development of the Learning Health System

Our primary approach is to construct the learning health system using all data currently housed in our Oncospace database. The system will be constructed with flexible application programming interfaces (API) that will encapsulate the prediction modules for generalized use. The APIs for the input of features and the output of prediction will support an array of decision support modules. The API to the knowledge base supports access to the necessary prior patient data for inclusion in the predictive modeling. This general framework will be used to complete the specific aims of this proposal.

Specific Aim 1: To Design, Implement, and Evaluate Data Science Models for Analyzing the Dose-Toxicity Relationships at the Sub-Organ Level, Identifying Specific Portions of the Organ(s) that are More or Less Critical and Sensitive to Radiation.

Our first year goal in Aim 1 is to build a platform for generating toxicity prediction models based on the spatial dose distributions. We intend on expanding our current work on DVH vs toxicity to a platform that explores dose variables beyond that of the traditional DVH based analysis.

Our goal is to explore discriminating spatial dose features that are most significant to the related toxicity. To do this, we will build a mechanism for extracting spatially dependent dose features in a variety of ways. The determination of these features is a topic of research and will be organ and toxicity dependent. The feature module will support an environment for engineering several types of features with the ability to add new ones with simple programming effort. These features may be as simple as separating the dose into organ octants to looking at more complex gradients in the dose distribution at critical organ boundaries. Features may also be related to multiple organs, or be outside of organs but have known relationships with the patient's anatomy.

The second component of Aim 1 is to build a machine learning module that will enable the exploration of a variety of machine learning or predictive modeling algorithms to be applied to the data. Methods such as random forest, linear regression and naïve Bayes can be applied to our system and evaluated for performance.

The overall framework can contain all methods, and be able to grow programmatically. The module can be applied at several institutions, and it will be available to other centers. Specifically, our Oncospace consortium member institutions of University of Washington and Washington University are building their head and neck databases and will be able to utilize these tools.

With Aim 1 we expect to have identified spatially dependent dose features and the associated predictive models that refine our ability to predict toxicity risk beyond what we could do with DVH curves alone. We will primarily focus on xerostomia, dysphagia, taste change, salivary function and voice change, and will explore all of the other toxicities that we score in our clinical workflow to find those where predictions are significant.

Specific Aim 2: To Broaden the Learning Health System to Study the Patient, Treatment and Disease-Related Features that Most Impact Radiation-Induced Toxicities, and to Apply Models that Stratify Patients to Maximize Statistical Significance of the Toxicity and Outcome Predictions.

The second year focus of Aim 2 is to identify which non-dosimetric features make patients "similar" when related to the outcome measure of interest. To do this we will include these non-dosimetric features in our predictive models and explore which of these features improve the predictive power of the models in Aim 1. For example, feeding tube support, on-treatment mucositis, age, disease location, and baseline xerostomia may all play a role in swallowing dysfunction.

The non-dosimetric features also can include extraction and processing from the raw clinical data. For example, the level of tracer uptake from a positron emission tomography scan may indicate the aggressiveness of a tumor or the baseline function of normal anatomy. That data can be converted to a feature or set of features that may be relevant to the model. This could be as simple as the mean specific uptake value in a region. Another example is the aggregate score from a baseline quality of life assessment, combining several questions to better describe swallowing function and nutritional support.

Similar to the extraction of spatial dose features, we can construct a module for engineering features from the non-dosimetric data including demographics, baseline function, diagnostic indicators, concurrent therapies and patient histories. This module will communicate with the predictive modeling through an API. It will also have access to the database through an API to obtain the raw input data for feature creation.

In Aim 2, we can incorporate the non-dosimetric features into the predictive modeling and find the set of features that maximally improves the predictive power of the models from Aim 1. We fully expect this framework to be continually developed and improved. As we extend the number of features and continually add to the knowledge base, better patient stratifications should be able to maximize our prediction of complications and outcomes for new patients.

Specific Aim 3: To Validate the Risk Prediction Models, and Ascertain their Usefulness in Assisting the Management of Cancer Patients.

The third year focus of Aim 3 is to develop validation tools for the risk prediction models derived in Aims 1 and 2. Initially, leave-one-out cross validation can be applied to patients in the database. A subset of patients can used to generate risk prediction models, and the remainder can be used to compare the methods in Aim 2. We can then use the data from the validation set to determine the accuracy of our predictions.

The second approach can be to validate the prediction for new patients. We can continue to prospectively collect clinical data on our new patients. This will provide new data that can be used for validation. This approach can focus on shorter term complications and outcomes initially. This prospective validation can be blind to the clinicians to avoid biases that may be introduced.

With data collection efforts beginning in 2008, it is now possible to predict late complications. Patients in the prospective study can continue to be evaluated for toxicities and late complications. Validation can also be possible by leaving a subset of patients with long term follow up out of the predictive models.

The third phase can be cross-institutional validation. We can validate the model features and the prediction accuracy with data accrued at the University of Washington and Washington University. These institutions are participating in the Oncospace consortium with focus on head and neck cancers with accrual rates of 150-200 patients per year. Validation of the features can be done by building the models from their knowledge bases and evaluating whether the same patient and spatial dose features are identified as being significant. This process can highlight variations in the data and uncover variations that may be institutionally dependent.

The other cross-institutional validation is that of the prediction. We have the opportunity to use models derived from one or all institutions to predict toxicities and outcomes for patients at any institution and determine which models provide the greatest accuracy. This may show that a model using data from all institutions predicts with higher accuracy, or it may show that data from the patient's own institution is more accurate.

By the end of this specific aim, all of the aforementioned validation tools can be built directly into the generalized learning health system. This includes resources to "publish"

validated models to the presentation layer, which can allow these models to be used for future predictions.

D.2. Conclusion

Thus, one embodiment includes a system that can demonstrate individualized medicine for cancer patients by substantially improving predictions of treatment related toxicities and enabling clinicians the ability to adjust their radiation doses or their symptom management regimens to improve care for their patients. The successful completion will uncover new knowledge about normal tissue complications in radiotherapy and provide an avenue for direct application of that knowledge to clinical practice.

We have demonstrated the success of our shape based planning models in a learning health system, and preliminary results on toxicity risk modeling with both DVH and spatial dosimetry show significant promise in our ability to improve our predictions. Having already generated much support and enthusiasm from a consortium of other oncology centers, the generalized learning health system is anticipated to have a profound impact on cancer care across the country.

REFERENCES

1. Intensity Modulated Radiation Therapy Collaborative Working Group, "Intensity-Modulated Radiotherapy: Current Status and Issues of Interest", International Journal of Radiation Oncology* Biology* Physics, 51(4), 2001, pp. 880-914.
2. Dhar, V., "Data Science and Prediction", Communications of the ACM, 56(12), 2013, pp. 64-73.
3. Schmarzo, B., Big Data: Understanding How Data Powers Big Business, John Wiley & Sons, 2013.
4. Wu, B., Ricchetti, F., Sanguineti, G., Kazhdan, M., Simari, P., Jacques, R., Taylor, R., and Mcnutt, T., "Data-Driven Approach to Generating Achievable Dose-Volume Histogram Objectives in Intensity-Modulated Radiotherapy Planning", International Journal of Radiation Oncology* Biology* Physics, 79(4), 2011, pp. 1241-1247.
5. Rubin, P., and Casarett, G., "Direction for Clinical Radiation Pathology. The Tolerance Dose.", in (Editor, 'ed.'^'eds.'): Book Direction for Clinical Radiation Pathology. The Tolerance Dose., Univ. of Rochester, N.Y., 1972
6. Lyman, J. T., "Complication Probability as Assessed from Dose-Volume Histograms", Radiation Research, 104(2s), 1985, pp. S13-S19.
7. Burman, C., Kutcher, G., Emami, B., and Goitein, M., "Fitting of Normal Tissue Tolerance Data to an Analytic Function", International Journal of Radiation Oncology* Biology* Physics, 21(1), 1991, pp. 123-135.
8. Emami, B., Lyman, J., Brown, A., Cola, L., Goitein, M., Munzenrider, J., Shank, B., Solin, L., and Wesson, M., "Tolerance of Normal Tissue to Therapeutic Irradiation", International Journal of Radiation Oncology* Biology* Physics, 21(1), 1991, pp. 109-122.
9. Kutcher, G., Burman, C., Brewster, L., Goitein, M., and Mohan, R., "Histogram Reduction Method for Calculating Complication Probabilities for Three-Dimensional Treatment Planning Evaluations", International Journal of Radiation Oncology* Biology* Physics, 21(1), 1991, pp. 137-146.
10. Kutcher, G. J., and Burman, C., "Calculation of Complication Probability Factors for Non-Uniform Normal Tissue Irradiation: The Effective Volume Method Gerald", International Journal of Radiation Oncology* Biology* Physics, 16(6), 1989, pp. 1623-1630.
11. Marks, L. B., Yorke, E. D., Jackson, A., Ten Haken, R. K., Constine, L. S., Eisbruch, A., Bentzen, S. M., Nam, J., and Deasy, J. O., "Use of Normal Tissue Complication Probability Models in the Clinic", International Journal of Radiation Oncology* Biology* Physics, 76(3), 2010, pp. S10-S19.
12. Fayyad, U., Piatetsky-Shapiro, G., and Smyth, P., "From Data Mining to Knowledge Discovery in Databases", AI magazine, 17(3), 1996, pp. 37.
13. Cios, K. J., and William Moore, G., "Uniqueness of Medical Data Mining", Artificial intelligence in medicine, 26(1), 2002, pp. 1-24.
14. Friedman, C. P., "A National Learning Health System", in (Editor, 'ed.'^'eds.'): Book A National Learning Health System, 2013
15. Cattell, R., "Scalable Sql and Nosql Data Stores", ACM SIGMOD Record, 39(4), 2011, pp. 12-27.
16. Dean, J., and Ghemawat, S., "Mapreduce: Simplified Data Processing on Large Clusters", Communications of the ACM, 51(1), 2008, pp. 107-113.
17. Intensity Modulated Radiation Therapy Collaborative Working Group. Intensity-modulated radiotherapy: current status and issues of interest. International Journal of Radiation Oncology* Biology* Physics. 2001; 51(4):880-914.
18. Marungo F, Robertson S, Quon H, et al. Creating a Data Science Platform for Developing Complication Risk Models for Personalized Treatment Planning in Radiation Oncology. 48th Hawaii International Conference on System Sciences (HICSS). Kauai, HI USA: IEEE; 2015.
19. Rubin P, Casarett G. Direction for clinical radiation pathology. The tolerance dose: Univ. of Rochester, N.Y.; 1972.
20. Lyman J T. Complication probability as assessed from dose-volume histograms. Radiation Research. 1985; 104 (2s): S13-S9.
21. Emami B, Lyman J, Brown A, et al. Tolerance of normal tissue to therapeutic irradiation. International Journal of Radiation Oncology* Biology* Physics. 1991; 21(1):109-22.
22. Burman C, Kutcher G, Emami B, Goitein M. Fitting of normal tissue tolerance data to an analytic function. International Journal of Radiation Oncology* Biology* Physics. 1991; 21(1):123-35.
23. Kutcher G J, Burman C. Calculation of complication probability factors for non-uniform normal tissue irradiation: The effective volume method gerald. International Journal of Radiation Oncology* Biology* Physics. 1989; 16(6):1623-30.
24. Niemierko A. Reporting and analyzing dose distributions: a concept of equivalent uniform dose. Medical physics. 1997; 24(1):103-10.
25. Marks L B, Yorke E D, Jackson A, et al. Use of normal tissue complication probability models in the clinic. International Journal of Radiation Oncology* Biology* Physics. 2010; 76(3):S10-S9.
26. Bentzen S M, Constine L S, Deasy J O, et al. Quantitative Analysis of Normal Tissue Effects in the Clinic (QUANTEC): An Introduction to the Scientific Issues. International Journal of Radiation Oncology Biology Physics. 2010 February; 76(3):S3-S9.
27. Konings A W, Cotteleer F, Faber H, van Luijk P, Meertens H, Coppes R P. Volume effects and region- 28. Konings A W, Faber H, Cotteleer F, Vissink A, Coppes R P. Secondary radiation damage as the main cause for unexpected volume effects: A histopathologic study of the parotid gland. International Journal of Radiation Oncology* Biology* Physics. 2006; 64(1):98-105.
29. van Luijk P, Faber H, Schippers J M, et al. Bath and shower effects in the rat parotid gland explain increased relative risk of parotid gland dysfunction after intensity-modulated radiotherapy. International Journal of Radiation Oncology* Biology* Physics. 2009; 74(4):1002-5.
30. Buettner F, Miah A B, Gulliford S L, et al. Novel approaches to improve the therapeutic index of head and neck radiotherapy: An analysis of data from the PAR-SPORT randomised phase III trial. Radiotherapy and Oncology. 2012; 103(1):82-7.
31. Dornfeld K, Simmons J R, Karnell L, et al. Radiation doses to structures within and adjacent to the larynx are correlated with long-term diet- and speech-related quality of life. International Journal of Radiation Oncology* Biology* Physics. 2007; 68(3):750-7.
32. Kumar R, Madanikia S, Starmer H, et al. Radiation dose to the floor of mouth muscles predicts swallowing complications following chemoradiation in oropharyngeal squamous cell carcinoma. Oral oncology. 2014; 50(1):65-70.
33. Dawson L A, Biersack M, Lockwood G, Eisbruch A, Lawrence T S, Ten Haken R K. Use of principal component analysis to evaluate the partial organ tolerance of normal tissues to radiation. International Journal of Radiation Oncology* Biology* Physics. 2005; 62(3):829-37.
34. Wu B, Ricchetti F, Sanguineti G, et al. Data-driven approach to generating achievable dose-volume histogram objectives in intensity-modulated radiotherapy planning International Journal of Radiation Oncology* Biology* Physics. 2011; 79(4):1241-7.
35. Domingos P. A few useful things to know about machine learning. Communications of the ACM. 2012; 55(10):78-87.
36. Kohavi R. A study of cross-validation and bootstrap for accuracy estimation and model selection. IJCAI; 1995; 1995. p. 1137-45.
37. Fayyad U, Irani K. Multi-interval discretization of continuous-valued attributes for classification learning. 1993.
38. Hand D J, Yu K. Idiot's Bayes—not so stupid after all? International statistical review. 2001; 69(3):385-98.
39. Breiman L. Bagging predictors. Machine learning. 1996; 24(2):123-40.
40. Breiman L. Random forests. Machine learning. 2001; 45(1):5-32.
41. Hall M, Frank E, Holmes G, Pfahringer B, Reutemann P, Witten I H. The WEKA data mining software: an update. ACM SIGKDD explorations newsletter. 2009; 11(1):10-8.
42. Rancati T, Schwarz M, Allen A M, et al. Radiation dose—volume effects in the larynx and pharynx. International Journal of Radiation Oncology* Biology* Physics. 2010; 76(3):S64-S9.
43. Dorr H, Lamkowski A, Graessle D H, et al. Linking the human response to unplanned radiation and treatment to the nonhuman primate response to controlled radiation and treatment. *Health Phys.* 2014; 106(1):129-134.
44. MacVittie T J, Bennett A, Booth C, et al. The prolonged gastrointestinal syndrome in rhesus macaques: The relationship between gastrointestinal, hematopoietic, and delayed multi-organ sequelae following acute, potentially lethal, partial-body irradiation. *Health Phys.* 2012; 103(4):427-453.
45. Wassenaar T R, Walsh M C, Cleary J F, Remington P L, Dietz A T. Disparities in the clinical trial participation of adult cancer patients. *J. Clin. Oncol.* 2008; 26:9524.
46. Vickers A J. Do we want more cancer patients on clinical trials? If so, what are the barriers to greater accrual. *Trials* 2008; 9:31.
47. Abernethy A P, Etheredge L M, Ganz P A, et al. Rapid-learning system for cancer care. *J. Clin. Oncol.* 2010; 28(27):4268-4274.
48. NCCN Clinical Practice Guidelines in Oncology. *National Comprehensive Cancer Network.* http://www.nccn.org/professionals/physician_gls/f_guidelines.asp. Accessed Oct. 24, 2014.
49. ASTRO Clinical Practice Guidelines. *American Society for Radiation Oncology.* https://www.astro.org/Clinical-Practice/Guidelines/Index.aspx. Accessed Oct. 24, 2014.
50. ASCO Guidelines. *American Society of Clinical Oncology.* http://www.asco.org/quality-guidelines/guidelines. Accessed Oct. 24, 2014.
51. Lambin P, van Stiphout R G P M, Starmans M H W, et al. Predicting outcomes in radiation oncology: Multifactorial decision support systems. *Nat. Rev. Clin. Oncol.* 2013; 10(1):27-40.
52. Mortensen H R, Jensen K, Grau C. Aspiration pneumonia in patients treated with radiotherapy for head and neck cancer. *Acta Oncol.* 2012; 52(2):270-276.
53. Gómez-Millán J, Toledo M D, Lupiañez Y, et al. Competing causes of death in patients with locoregionally advanced head and neck cancer treated with concomitant boost radiation plus concurrent weekly cisplatin. *Clin. Transl. Oncol.* 2013; 15(4):321-326.
54. Ferlito A, Jr M H, Bradley P J, et al. Causes of death of patients with laryngeal cancer. *Eur. Arch. Otorhinolaryngol.* 2014; 271(3):425-434.
55. Quon H, Yang W, Kumar R, et al. Swallow function in patients with oropharyngeal squamous cell carcinomas treated with radiation therapy dose de-escalation. *Int. J. Radiat. Oncol. Biol. Phys.* 2013; 87(2):S141-S142.
56. Quon H, Cheng Z, Starmer H, et al. Effective pain management of mucositis with prophylactic gabapentin in the irradiated head and neck cancer patient is associated with functional benefits. *Int. J. Radiat. Oncol. Biol. Phys.* 2014; 90(1):S559-S560.
57. Starmer H M, Yang W, Raval R, et al. Effect of gabapentin on swallowing during and after chemoradiation for oropharyngeal squamous cell cancer. *Dysphagia* 2014; 29(3):396-402.
58. Kumar R, Madanikia S, Starmer H, et al. Radiation dose to the floor of mouth muscles predicts swallowing complications following chemoradiation in oropharyngeal squamous cell carcinoma. *Oral Oncol.* 2014; 50(1):65-70.
59. Nutting C M, Morden J P, Harrington K J, et al. Parotid-sparing intensity modulated versus conventional radiotherapy in head and neck cancer (PARSPORT): a phase 3 multicentre randomised controlled trial. *Lancet Oncol.* 2011; 12(2):127-136.
60. Gupta T, Agarwal J, Jain S, et al. Three-dimensional conformal radiotherapy (3D-CRT) versus intensity modulated radiation therapy (IMRT) in squamous cell carcinoma of the head and neck: A randomized controlled trial. *Radiother. Oncol.* 2012; 104(3):343-348.

61. Pauloski B R, Rademaker A W, Logemann J A, Discekici-Harris M, Mittal B B. Comparison of swallowing function after intensity-modulated radiation therapy and conventional radiotherapy for head and neck cancer. *Head Neck* 2014:1-8.
62. Tan L I, Low S H, Mat-Nor N, Heng S P. Quality of life in nasopharyngeal cancer (NPC) patients: study of salivary flow recovery pattern on xerostomia improvement for intensity modulated radiation therapy (IMRT) versus volumetric modulated arc therapy (VMAT). *Int. J Radiat. Oncol. Biol. Phys.* 2014; 90(1):S525.
63. Adams G, Burnett R, Mills E, Penniment M. Objective and subjective changes in voice quality after radiotherapy for early (T1 or T2, NO) laryngeal cancer: A pilot prospective cohort study. *Head Neck* 2013; 35(3):376-380.
64. Tuomi L, Andréll P, Finizia C. Effects of voice rehabilitation after radiation therapy for laryngeal cancer: a randomized controlled study. *Int. J. Radiat. Oncol. Biol. Phys.* 2014; 89(5):964-972.
65. McQuestion M, Fitch M, Howell D. The changed meaning of food: Physical, social and emotional loss for patients having received radiation treatment for head and neck cancer. *Eur. J. Oncol. Nurs.* 2011; 15(2):145-151.
66. Nguyen H M, Reyland M E, Barlow L A. Mechanisms of taste bud cell loss after head and neck irradiation. *J. Neurosci.* 2012; 32(10):3474-3484.
67. Marks L B, Ten Haken R K, Martel M K. Guest editor's introduction to QUANTEC: A users guide. *Int. J. Radiat. Oncol. Biol. Phys.* 2010; 76:S1-S2.
68. Bentzen S M, Constine L S, Deasy J O, et al. Quantitative analyses of normal tissue effects in the clinic (QUANTEC): An introduction to the scientific issues. *Int. J. Radiat. Oncol. Biol. Phys.* 2010; 76:S3-S9.
69. Deasy J O, Bentzen S M, Jackson A, et al. Improving normal tissue complication probability models: The need to adopt a "data-pooling" culture. *Int. J. Radiat. Oncol. Biol. Phys.* 2010; 76:S151-S154.
70. Marks L B, Yorke E D, Jackson A, et al. Use of normal tissue complication probability models in the clinic. *Int. J. Radiat. Oncol. Biol. Phys.* 2010; 76:S10-S19.
71. Moore K L, Kagadis G C, McNutt T R, Moiseenko V, Mutic S. Vision 20/20: Automation and advanced computing in clinical radiation oncology. *Med. Phys.* 2014; 41(1):010901.
72. Kawamoto K. Improving clinical practice using clinical decision support systems: a systematic review of trials to identify features critical to success. *BMJ* 2005; 330 (7494):765-0.
73. Brown T, Banks M, Hughes B, Kenny L, Lin C, Bauer J. Protocol for a randomized controlled trial of early prophylactic feeding via gastrostomy versus standard care in high risk patients with head and neck cancer. *BMC Nurs.* 2014; 13(1):17.
74. Langius J A E, van Dijk A M, Doomaert P, et al. More than 10% weight loss in head and neck cancer patients during radiotherapy is independently associated with deterioration in quality of life. *Nutr. Cancer* 2013; 65(1): 76-83.
75. Langius J a. E, Bakker S, Rietveld D H F, et al. Critical weight loss is a major prognostic indicator for disease-specific survival in patients with head and neck cancer receiving radiotherapy. *Br. J. Cancer* 2013; 109(5):1093-1099.
76. Trotti A, Colevas A D, Setser A, et al. CTCAE v3.0: development of a comprehensive grading system for the adverse effects of cancer treatment. *Semin. Radiat. Oncol.* 2003; 13(3):176-181.
77. List M A, D'Antonio L L, Cella D F, et al. The performance status scale for head and neck cancer patients and the functional assessment of cancer therapy-head and neck scale: A study of utility and validity. *Cancer* 1996; 77(11):2294-2301.
78. Chen A Y, Frankowski R, Julie Bishop-Leone, et al. The development and validation of a dysphagia-specific quality-of-life questionnaire for patients with head and neck cancer: The M. D. Anderson dysphagia inventory. *Arch. Otolaryngol. Neck Surg.* 2001; 127(7):870-876.
79. Yang W Y, Moore J, Quon H, et al. Browser based platform in maintaining clinical activities—use of the iPads in head and neck clinics. *J. Phys. Conf. Ser.* 2014; 489(1):012095.
80. Fayyad U, Piatetsky-Shapiro G, Smyth P. From data mining to knowledge discovery in databases. *AI Mag.* 1996; 17(3):37.
81. Schmarzo B. *Big Data: Understanding How Data Powers Big Business.* 1st edition. Indianapolis, Ind.: Wiley; 2013.
82. Wu B, Ricchetti F, Sanguineti G, et al. Patient geometry-driven information retrieval for IMRT treatment plan quality control. *Med. Phys.* 2009; 36(12):5497-5505.
83. Wu B, Ricchetti F, Sanguineti G, et al. Data-driven approach to generating achievable dose-volume histogram objectives in intensity-modulated radiotherapy planning. *Int. J. Radiat. Oncol. Biol. Phys.* 2011; 79(4):1241-1247.
84. Ries L A G, Melbert D, Krapcho M, et al. *SEER Cancer Statistics Review,* 1975-2005. National Cancer Institute; 2008.
85. DeHart K, Holbrook J. Emergency department applications of digital dictation and natural language processing. *J. Ambulatory Care Manage.* 1992; 15(4):18-23.
86. Hazlehurst B, Frost H R, Sittig D F, Stevens V J. MediClass: A system for detecting and classifying encounter-based clinical events in any electronic medical record. *J. Am. Med. Inform. Assoc.* 2005; 12(5):517-529.
87. Das I J, Cheng C W, Chopra K L, Mitra R K, Srivastava S P, Glatstein E. Intensity-modulated radiation therapy dose prescription, recording, and delivery: patterns of variability among institutions and treatment planning systems. *J. Natl. Cancer Inst.* 2008; 100(5):300-307.
88. Mell L K, Mehrotra A K, Mundt A J. Intensity-modulated radiation therapy use in the U.S., 2004. *Cancer* 2005; 104(6):1296-1303.
89. Jalali R. Particle therapy in clinical practice: is there enough evidence to justify the current surge in interest? *J. Cancer Res. Ther.* 2008; 4(2):54-56.
90. Pijls-Johannesma M, Pommier P, Lievens Y. Cost-effectiveness of particle therapy: current evidence and future needs. *Radiother. Oncol. I Eur. Soc. Ther. Radiol. Oncol.* 2008; 89(2):127-134.
91. Jackson A. Summarizing our knowledge of normal tissue tolerances: the progress and future directions of QUANTEC. *Med. Phys.* 2008; 35:2863.
92. Marks L. A clinician's view of QUANTEC. *Med. Phys.* 2008; 35(6).
93. Potosky A L, Davis W W, Hoffman R M, et al. Five-year outcomes after prostatectomy or radiotherapy for prostate cancer: the prostate cancer outcomes study. *J. Natl. Cancer Inst.* 2004; 96(18):1358-1367.
94. McDade T P, Hill J S, Simons J P, et al. A national propensity-adjusted analysis of adjuvant radiotherapy in the treatment of resected pancreatic adenocarcinoma. *Cancer* 2010; 116(13):3257-3266.

95. Lin S H, Wang L, Myles B, et al. Propensity score-based comparison of long-term outcomes with 3-dimensional conformal radiotherapy vs intensity-modulated radiotherapy for esophageal cancer. *Int. J. Radiat. Oncol. Biol. Phys.* 2012; 84(5):1078-1085.
96. Robertson S P, Quon H, Kiess A P, et al. A data-mining algorithm for large scale analysis of dose-outcome relationships in a database of irradiated head-and-neck (HN) cancer patients. *Med. Phys.* 2014; 41(6):410.
97. Robertson S P, Quon H, Kiess A, et al. A data-mining framework for large scale analysis of dose-outcome relationships in a database of irradiated head and neck (HN) cancer patients. *Med. Phys.* (submitted).
98. Dawson L A, Biersack M, Lockwood G, Eisbruch A, Lawrence T S, Ten Haken R K. Use of principal component analysis to evaluate the partial organ tolerance of normal tissues to radiation. *Int. J. Radiat. Oncol. Biol. Phys.* 2005; 62(3):829-837.
99. El Naqa I, Bradley J, Blanco A I, et al. Multivariable modeling of radiotherapy outcomes, including dose-volume and clinical factors. *Int. J. Radiat. Oncol. Biol. Phys.* 2006; 64(4):1275-1286.
100. Söhn M, Yan D, Liang J, Meldolesi E, Vargas C, Alber M. Incidence of late rectal bleeding in high-dose conformal radiotherapy of prostate cancer using equivalent uniform dose-based and dose-volume-based normal tissue complication probability models. *Int. J. Radiat. Oncol. Biol. Phys.* 2007; 67(4):1066-1073.
101. Ebert M A, Foo K, Haworth A, et al. Derivation and representation of dose-volume response from large clinical trial data sets: an example from the RADAR prostate radiotherapy trial. *J. Phys. Conf. Ser.* 2014; 489(1):012090.
102. Deasy J O, Moiseenko V, Marks L, Chao K S C, Nam J, Eisbruch A. Radiotherapy dose-volume effects on salivary gland function. *Int. J. Radiat. Oncol. Biol. Phys.* 2010; 76:S58-S63.
103. Konings A W T, Cotteleer F, Faber H, van Luijk P, Meertens H, Coppes R P. Volume effects and region-dependent radiosensitivity of the parotid gland. *Int. J. Radiat. Oncol. Biol. Phys.* 2005; 62(4):1090-1095.
104. Buettner F, Miah A B, Gulliford S L, et al. Novel approaches to improve the therapeutic index of head and neck radiotherapy: An analysis of data from the PARSPORT randomised phase III trial. *Radiother. Oncol.* 2012; 103(1):82-87.
105. Buettner F, Gulliford S L, Webb S, Partridge M. Modeling late rectal toxicities based on a parameterized representation of the 3D dose distribution. *Phys. Med. Biol.* 2011; 56(7):2103.
106. Vinogradskiy Y, Tucker S L, Liao Z, Martel M K. A novel method to incorporate the spatial location of the lung dose distribution into predictive radiation pneumonitis modeling. *Int. J. Radiat. Oncol. Biol. Phys.* 2012; 82(4):1549-1555.
107. Marungo F, Robertson S P, Quon H, et al. Creating a data science platform for developing complication risk models for personalized treatment planning in radiation oncology. In: *Hawaii International Conference on System Sciences.* Vol 48 (in press).
108. Marungo F, Robertson S P, Quon H, Taylor R H, McNutt T R. Machine learning based risk modeling of voice dysfunction and xerostomia using spatial dose distribution in intensity-modulated radiation therapy. *J. Am. Med. Inform. Assoc.* (submitted).
109. Lyman J T. Complication probability as assessed from dose-volume histograms. *Radiat. Res.* 1985; 104:S13-S19.
110. Kutcher G J, Burman C. Calculation of complication probability factors for non-uniform normal tissue irradiation: The effective volume method. *Int. J. Radiat. Oncol. Biol. Phys.* 1989; 16(6):1623-1630.
111. Burman C, Kutcher G J, Emami B, Goitein M. Fitting of normal tissue tolerance data to an analytic function. *Int. J. Radiat. Oncol. Biol. Phys.* 1991; 21(1):123-135.
112. Emami B, Lyman J, Brown A, et al. Tolerance of normal tissue to therapeutic irradiation. *Int. J. Radiat. Oncol. Biol. Phys.* 1991; 21(1):109-122.
113. Breiman L. Random forests. *Mach. Learn.* 2001; 45(1):5-32.
114. Breiman L. Bagging predictors. *Mach. Learn.* 1996; 24(2):123-140.
115. Matsuo K, Palmer J B. Anatomy and physiology of feeding and swallowing: Normal and abnormal. *Phys. Med. Rehabil. Clin. N. Am.* 2008; 19:691-707.
116. Acosta O, Drean G, Ospina J D, et al. Voxel-based population analysis for correlating local dose and rectal toxicity in prostate cancer radiotherapy. *Phys. Med. Biol.* 2013; 58(8):2581.

What is claimed is:

1. A computer system for radiation treatment planning, the system comprising:
   a memory storing computer-executable instructions; and
   a processor that is coupled to the memory and that is configured to execute the computer-executable instructions to:
      receive, from a relational database, treatment data associated with a target volume from each of a plurality of previous patients, the treatment data comprising three-dimensional dose grid treatment plan data associated with the target volume for each of said plurality of previous patients, dose-volume histogram (DVH) data associated with the target volume for each of said plurality of previous patients, and treatment outcome data associated with each of said plurality of previous patients;
      calculate a plurality of candidate features using the treatment data;
      identify a predetermined number of candidate features based on an information gain of each of the calculated plurality of candidate features;
      select a first subset of the identified candidate features to generate a machine-learning model for determining radiation treatment-related risk based on input to the model of the plurality of candidate features;
      select a second subset of the identified candidate features to train the machine-learning model for determining radiation treatment-related risk; and
      use the trained machine-learning model for determining radiation treatment-related risk to determine a particular radiation treatment-related risk associated with a particular radiation treatment plan for a current patient,
      wherein the plurality of candidate features from the treatment plan are generated by using at least the treatment data to calculate a dose grid distribution for a band of radiation delivered to the target volume, the dose grid distribution representing a percentage of total radiation dose with the band delivered to the respective target volume, the dose grid distribution including a plurality of different dose groupings.

2. The system of claim 1, further comprising calculating for the particular radiation treatment plan at least one of a probability of toxicity and a probability of treatment failure for the target volume, wherein the generating the machine-learning model incorporates the calculated probability.

3. The system of claim 1, wherein said determined particular radiation treatment-related risk associated with the particular radiation treatment plan includes failure to cure said patient of a disease or condition due to one of an insufficient application of radiation to the at least one target volume and the application of radiation spatially missing the disease in the target volume.

4. The system of claim 1, wherein the candidate features comprise a plurality of spatial features of the target volume, wherein the plurality of spatial features comprise at least one of a dose band delivered to a sub-region of the target volume, and wherein the processor is further configured to execute the computer-executable instructions to calculate the spatial features for each patient using at least the three-dimensional dose grid treatment plan data associated with the target volume for each of said plurality of previous patients.

5. The system of claim 1, wherein the candidate features comprise a plurality of DVH-based features of the target volume, wherein the DVH-based features comprise an effective volume, a maximum dose, and a normal tissue complication probability, and wherein the processor is further configured to execute the computer-executable instructions to calculate the DVH features for each patient using at least the dose-volume histogram (DVH) data associated with the target volume for each of said plurality of previous patients.

6. The system of claim 1, wherein the processor is further configured to execute the computer-executable instructions to use the trained machine-learning model to formulate a particular radiation treatment plan that minimizes the radiation treatment related risk for another patient.

7. The system of claim 6, wherein formulating the particular radiation treatment plan is based on at least one of age, race, concurrent therapies, disease location, histology, social history, medical history of the patient, and assessing patient-specific risk tolerances as input.

8. The system of claim 1, wherein generating the machine-learning model comprises using at least one of logistic regression, and further comprising repeating the logistic regression at finer volume resolution.

9. A non-transitory computer-readable storage medium for radiation treatment planning, the computer-readable medium storing instructions that, when executed, causes a computer to:

receive, from a relational database, treatment data associated with a target volume from each of a plurality of previous patients, the treatment data comprising three-dimensional dose grid treatment plan data associated with the target volume for each of said plurality of previous patients, dose-volume histogram (DVH) data associated with the target volume for each of said plurality of previous patients, and treatment outcome data associated with each of said plurality of previous patients;

calculate a plurality of candidate features using the treatment data;

identify a predetermined number of candidate features based on an information gain of each of the calculated plurality of candidate features;

select a first subset of the identified candidate features to generate a machine-learning model for determining radiation treatment-related risk based on input to the model of the plurality of candidate features;

select a second subset of the identified candidate features to train the machine-learning model for determining radiation treatment-related risk; and use the trained machine-learning model for determining radiation treatment-related risk to determine a particular radiation treatment-related risk associated with a particular radiation treatment plan for a current patient, wherein the plurality of candidate features from the treatment plan are generated by using at least the treatment data to calculate a dose grid distribution for a band of radiation delivered to the target volume, the dose grid distribution representing a percentage of total radiation dose with the band delivered to the respective target volume, the dose grid distribution including a plurality of different dose groupings.

10. The non-transitory computer-readable storage medium of claim 9, the instructions further configuring the computer to calculate for the particular radiation treatment plan at least one of a probability of toxicity and a probability of treatment failure for the target volume, wherein the generating the machine-learning model incorporates the calculated probability.

11. The non-transitory computer-readable storage medium of claim 9, wherein said determined particular radiation treatment-related risk associated with the particular radiation treatment plan includes failure to cure said patient of a disease or condition due to one of an insufficient application of radiation to the at least one target volume and the application of radiation spatially missing the disease in the target volume.

12. The non-transitory computer-readable storage medium of claim 9, wherein the candidate features comprise a plurality of spatial features of the target volume, wherein the plurality of spatial features comprise at least one of a dose band delivered to a sub-region of the target volume, and wherein the instructions further configure the computer to calculate the spatial features for each patient using at least the three-dimensional dose grid treatment plan data associated with the target volume for each of said plurality of previous patients.

13. The non-transitory computer-readable storage medium of claim 9, wherein the candidate features comprise a plurality of DVH-based features of the target volume, wherein the DVH-based features comprise an effective volume, a maximum dose, and a normal tissue complication probability, and wherein the instructions further configure the computer to calculate the DVH features for each patient using at least the dose-volume histogram (DVH) data associated with the target volume for each of said plurality of previous patients.

14. The non-transitory computer-readable storage medium of claim 9, wherein the instructions further configure the computer to use the trained machine-learning model for determining radiation treatment related risk to formulate a particular radiation treatment plan that minimizes the radiation treatment related risk for another patient.

15. The non-transitory computer-readable storage medium of claim 14, wherein formulating the particular radiation treatment plan is based on at least one of age, race, concurrent therapies, disease location, histology, social history, medical history of the patient, and assessing patient-specific risk tolerances as input.

16. The non-transitory computer-readable storage medium of claim 9, wherein generating the machine-learning model comprises using at least one of logistic regression, and further comprising repeating the logistic regression at finer volume resolution.

\* \* \* \* \*